United States Patent
Brodie et al.

(10) Patent No.: US 10,098,896 B2
(45) Date of Patent: Oct. 16, 2018

(54) C-17-HETEROARYL STEROIDAL CYP17 INHIBITORS/ANTIANDROGENS, IN VITRO BIOLOGICAL ACTIVITIES, PHARMACOKINETICS AND ANTITUMOR ACTIVITY

(71) Applicant: The University of Maryland, Baltimore, Baltimore, MD (US)

(72) Inventors: Angela Brodie, Fulton, MD (US); Vincent C. O. Njar, Glen Burnie, MD (US)

(73) Assignee: UNIVERSITY OF MARYLAND BALTIMORE, Baltimore, MD (US)

( * ) Notice: Subject to any disclaimer, the term of this patent is extended or adjusted under 35 U.S.C. 154(b) by 0 days.

(21) Appl. No.: 15/159,117

(22) Filed: May 19, 2016

(65) Prior Publication Data

US 2018/0036320 A1    Feb. 8, 2018

Related U.S. Application Data

(60) Continuation of application No. 14/081,910, filed on Nov. 15, 2013, now abandoned, which is a continuation of application No. 12/577,090, filed on Oct. 9, 2009, now abandoned, which is a division of application No. 11/817,550, filed as application No. PCT/US2006/007143 on Mar. 2, 2006, now Pat. No. 7,875,599.

(60) Provisional application No. 60/657,390, filed on Mar. 2, 2005.

(51) Int. Cl.
*A61K 31/58*    (2006.01)
*C07J 43/00*    (2006.01)

(52) U.S. Cl.
CPC .............. *A61K 31/58* (2013.01); *C07J 43/003* (2013.01)

(58) Field of Classification Search
CPC ..................................................... A61K 31/58
USPC ........................................................ 514/176
See application file for complete search history.

(56) References Cited

U.S. PATENT DOCUMENTS

| | | |
|---|---|---|
| 2,664,423 A | 12/1953 | Rorig |
| 3,060,174 A | 10/1962 | Albert et al. |
| 3,313,809 A | 4/1967 | Clinton et al. |
| 3,317,520 A | 5/1967 | Clinton |
| 3,480,621 A | 11/1969 | Loken et al. |
| 3,539,687 A | 11/1970 | Kuhnen et al. |
| 4,000,125 A | 12/1976 | Casagrande et al. |
| 4,316,885 A | 2/1982 | Rakhit |
| 4,650,803 A | 3/1987 | Stella et al. |
| 5,023,263 A | 6/1991 | Von Burg |
| 5,023,264 A | 6/1991 | Caufield et al. |
| 5,028,726 A | 7/1991 | Farrell |
| 5,100,883 A | 3/1992 | Schiehser |
| 5,104,895 A | 4/1992 | Spinelli et al. |
| 5,118,677 A | 6/1992 | Caufield |
| 5,118,678 A | 6/1992 | Kao et al. |
| 5,120,842 A | 6/1992 | Failli et al. |
| 5,151,413 A | 9/1992 | Caufield et al. |
| 5,162,333 A | 11/1992 | Failli et al. |
| 5,177,203 A | 1/1993 | Failli et al. |
| 5,221,670 A | 6/1993 | Caufield |
| 5,232,917 A | 8/1993 | Bolger et al. |
| 5,233,036 A | 8/1993 | Hughes |
| 5,237,064 A | 8/1993 | Bakshi et al. |
| 5,256,790 A | 10/1993 | Nelson |
| 5,258,389 A | 11/1993 | Goulet et al. |
| 5,260,300 A | 11/1993 | Hu |
| 5,262,423 A | 11/1993 | Kao |
| 5,264,427 A | 11/1993 | Brodie et al. |
| 5,270,163 A | 12/1993 | Gold et al. |
| 5,300,294 A | 4/1994 | Johnson |
| 5,302,584 A | 4/1994 | Kao et al. |
| 5,362,718 A | 11/1994 | Skotnicki et al. |
| 5,373,014 A | 12/1994 | Failli et al. |
| 5,378,836 A | 1/1995 | Kao et al. |
| 5,385,908 A | 1/1995 | Nelson et al. |
| 5,385,909 A | 1/1995 | Nelson et al. |
| 5,385,910 A | 1/1995 | Ocain et al. |
| 5,385,936 A | 1/1995 | Flack et al. |
| 5,389,639 A | 2/1995 | Failli et al. |
| 5,391,730 A | 2/1995 | Skotnicki et al. |

(Continued)

FOREIGN PATENT DOCUMENTS

| | | |
|---|---|---|
| CN | 101023349 A | 8/2007 |
| CN | 101607985 A | 12/2009 |

(Continued)

OTHER PUBLICATIONS

U.S. Appl. No. 14/081,910, filed Nov. 15, 2013, Brodie et al.

(Continued)

*Primary Examiner* — Barbara P Badio

(74) *Attorney, Agent, or Firm* — Westerman, Hattori, Daniels & Adrian, LLP

(57) ABSTRACT

Described are steroidal C-17 benzoazoles, pyrimidinoazoles (azabenzoazoles) and diazines. Methods for their synthesis are also described, which include methods having a step of nucleophilic vinylic "addition-elimination" substitution reaction of 3β-acetoxy-17-chloro-16-formylandrosta-5,16-diene or analogs thereof and benzoazole or pyrimidinoazole nucleophiles and methods having a palladium catalyzed cross-coupling reaction of 17-iodoandrosta-5,16-dien-3β-ol or analogs thereof with tributylstannyl diazines. The compounds are potent inhibitors of human CYP17 enzyme as well as potent antagonists of both wild type and mutant androgen receptors (AR). The compounds are useful for the treatment of human prostate cancer.

6 Claims, 8 Drawing Sheets

(56) References Cited

U.S. PATENT DOCUMENTS

Figure 1:
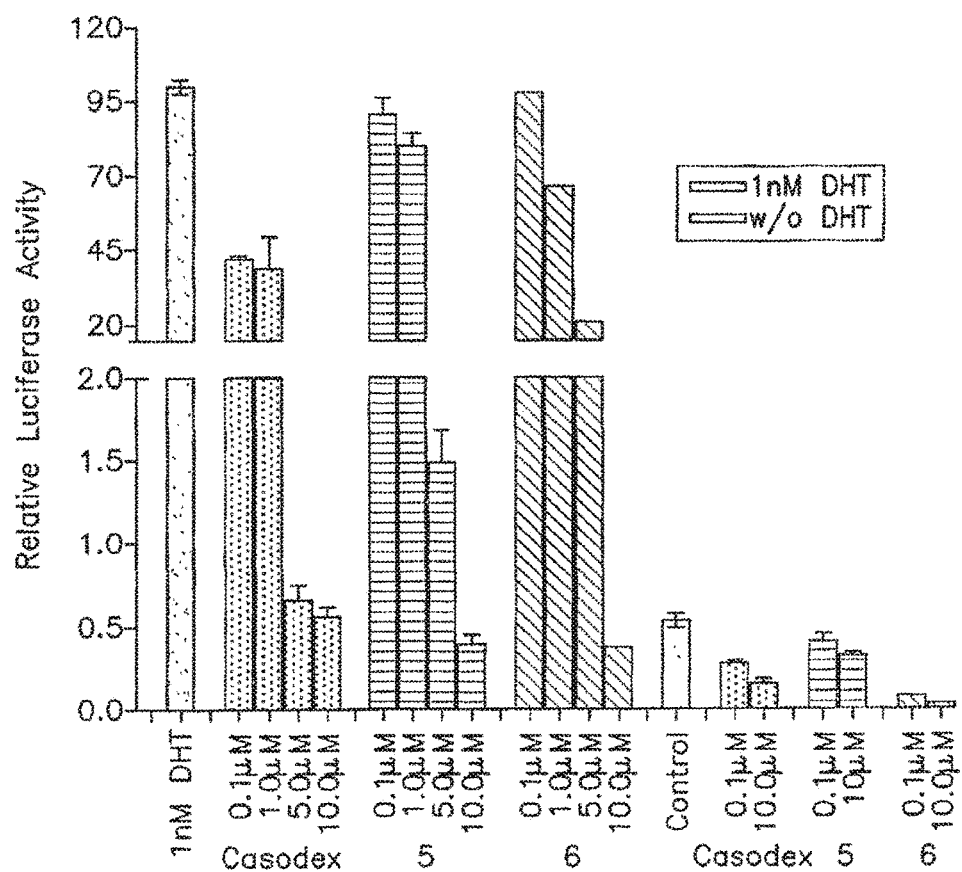

| | | |
|---|---|---|
| 5,411,967 A | 5/1995 | Kao et al. |
| 5,434,260 A | 7/1995 | Skotnicki et al. |
| 5,456,923 A | 10/1995 | Nakamichi et al. |
| 5,463,048 A | 10/1995 | Skotnicki et al. |
| 5,475,096 A | 12/1995 | Gold et al. |
| 5,480,988 A | 1/1996 | Failli et al. |
| 5,480,989 A | 1/1996 | Kao et al. |
| 5,489,680 A | 2/1996 | Failli et al. |
| 5,491,231 A | 2/1996 | Nelson et al. |
| 5,496,556 A | 3/1996 | Johnson |
| 5,504,091 A | 4/1996 | Molnar-Kimber et al. |
| 5,512,570 A | 4/1996 | Dorn et al. |
| 5,563,145 A | 10/1996 | Failli et al. |
| 5,567,588 A | 10/1996 | Gold et al. |
| 5,595,877 A | 1/1997 | Gold et al. |
| 5,601,981 A | 2/1997 | Malins |
| 5,604,213 A | 2/1997 | Barrie et al. |
| 5,620,986 A | 4/1997 | Witzel et al. |
| 5,637,310 A | 6/1997 | Johnson |
| 5,637,459 A | 6/1997 | Burke et al. |
| 5,660,985 A | 8/1997 | Pieken et al. |
| 5,665,772 A | 9/1997 | Cottens et al. |
| 5,670,637 A | 9/1997 | Gold et al. |
| 5,672,605 A | 9/1997 | Or et al. |
| 5,683,867 A | 11/1997 | Biesecker et al. |
| 5,696,249 A | 12/1997 | Gold et al. |
| 5,707,796 A | 1/1998 | Gold et al. |
| 5,721,227 A | 2/1998 | Melloni et al. |
| 5,741,795 A | 4/1998 | Aster et al. |
| 5,780,462 A | 7/1998 | Lee et al. |
| 5,994,334 A | 11/1999 | Brodie et al. |
| 5,994,335 A | 11/1999 | Brodie et al. |
| 6,011,020 A | 1/2000 | Gold et al. |
| 6,133,280 A | 10/2000 | Brodie et al. |
| 6,200,965 B1 | 3/2001 | Brodie et al. |
| 6,368,598 B1 | 4/2002 | D'Amico et al. |
| 6,444,649 B1 | 9/2002 | Inamori et al. |
| 6,444,683 B2 | 9/2002 | Brodie et al. |
| 6,546,555 B1 | 4/2003 | Curatolo et al. |
| 6,763,607 B2 | 7/2004 | Beyerinck et al. |
| 6,933,312 B2 | 8/2005 | Price et al. |
| 6,960,584 B2 | 11/2005 | Carling et al. |
| 6,973,741 B2 | 12/2005 | Beyerinck et al. |
| 6,982,258 B2 | 1/2006 | Posner et al. |
| 7,098,208 B2 | 8/2006 | Owens et al. |
| 7,192,974 B2 | 3/2007 | Gravestock et al. |
| 7,223,738 B2 | 5/2007 | Bilodeau et al. |
| 7,304,063 B2 | 12/2007 | Bilodeau et al. |
| 7,378,403 B2 | 5/2008 | Kozikowski et al. |
| 7,396,832 B2 | 7/2008 | Lindsley et al. |
| 7,399,764 B2 | 7/2008 | Duggan et al. |
| 7,414,055 B2 | 8/2008 | Duggan et al. |
| 7,544,677 B2 | 6/2009 | Bilodeau et al. |
| 7,576,209 B2 | 8/2009 | Kelly et al. |
| 7,579,355 B2 | 8/2009 | Bilodeau et al. |
| 7,589,068 B2 | 9/2009 | Cosford et al. |
| 7,604,947 B2 | 10/2009 | Gudas |
| 7,638,530 B2 | 12/2009 | Bilodeau et al. |
| 7,655,649 B2 | 2/2010 | Bilodeau et al. |
| 7,705,014 B2 | 4/2010 | Chen et al. |
| 7,750,151 B2 | 7/2010 | Bilodeau et al. |
| 7,780,988 B2 | 8/2010 | Beyerinck et al. |
| 7,807,393 B2 | 10/2010 | Thaxton et al. |
| 7,875,599 B2 | 1/2011 | Brodie et al. |
| 7,887,840 B2 | 2/2011 | Curatolo et al. |
| 7,943,732 B2 | 5/2011 | Reed |
| 7,960,435 B2 | 6/2011 | Njar et al. |
| 8,003,643 B2 | 8/2011 | Bilodeau et al. |
| 8,003,651 B2 | 8/2011 | Mitchell et al. |
| 8,008,317 B2 | 8/2011 | Armstrong et al. |
| 8,026,286 B2 | 9/2011 | Curatolo et al. |
| 8,034,381 B2 | 10/2011 | Moschwitzer |
| 8,110,550 B2 | 2/2012 | Brodie et al. |
| 8,129,184 B2 | 3/2012 | Yu |
| 8,133,724 B2 | 3/2012 | Qiu et al. |
| 8,168,652 B2 | 5/2012 | Sanderson et al. |
| 8,257,741 B2 | 9/2012 | Curatolo et al. |
| 8,263,357 B2 | 9/2012 | Reed |
| 8,273,782 B2 | 9/2012 | Seefeld et al. |
| 8,324,221 B2 | 12/2012 | Banka et al. |
| 8,785,423 B2 | 7/2014 | Njar et al. |
| 8,791,094 B2 | 7/2014 | Morrison et al. |
| 8,791,095 B2 | 7/2014 | Casebier |
| 8,822,438 B2 | 9/2014 | Auerbach et al. |
| 8,841,422 B2 | 9/2014 | Qiu et al. |
| 8,927,515 B2 | 1/2015 | Brown et al. |
| 9,018,198 B2 | 4/2015 | Njar et al. |
| 9,156,878 B2 | 10/2015 | Morrison et al. |
| 9,295,679 B2 | 3/2016 | Njar et al. |
| 9,439,912 B2 | 9/2016 | Njar et al. |
| 2001/0001099 A1 | 5/2001 | Brodie et al. |
| 2002/0009494 A1 | 1/2002 | Curatolo et al. |
| 2003/0054053 A1 | 3/2003 | Young et al. |
| 2003/0059471 A1 | 3/2003 | Compton et al. |
| 2004/0058896 A1 | 3/2004 | Dietrich et al. |
| 2006/0013873 A1 | 1/2006 | Yang et al. |
| 2006/0204568 A1 | 9/2006 | Liversidge et al. |
| 2007/0037867 A1 | 2/2007 | Santen et al. |
| 2007/0185152 A1 | 8/2007 | Yamashita et al. |
| 2007/0238647 A1 | 10/2007 | Bowen et al. |
| 2008/0058301 A1 | 3/2008 | Lardy et al. |
| 2008/0280864 A1 | 11/2008 | Brodie et al. |
| 2009/0012045 A1 | 1/2009 | Hitoshi et al. |
| 2009/0047252 A1 | 2/2009 | Cai et al. |
| 2009/0048149 A1 | 2/2009 | Ng et al. |
| 2009/0221672 A1 | 9/2009 | Zhang et al. |
| 2010/0009397 A1 | 1/2010 | Sebti et al. |
| 2010/0029667 A1 | 2/2010 | Ketner et al. |
| 2010/0047338 A1 | 2/2010 | Brodie et al. |
| 2010/0048524 A1 | 2/2010 | Brodie et al. |
| 2010/0048912 A1 | 2/2010 | Brodie et al. |
| 2010/0048913 A1 | 2/2010 | Brodie et al. |
| 2010/0048914 A1 | 2/2010 | Brodie et al. |
| 2010/0068802 A1 | 3/2010 | Qiu et al. |
| 2010/0137269 A1 | 6/2010 | Brodie et al. |
| 2010/0298383 A1 | 11/2010 | Ng et al. |
| 2011/0034428 A1 | 2/2011 | Morrison et al. |
| 2011/0105445 A1 | 5/2011 | Njar et al. |
| 2011/0110926 A1 | 5/2011 | Luo et al. |
| 2011/0118219 A1 | 5/2011 | Njar et al. |
| 2011/0160170 A1 | 6/2011 | Njar et al. |
| 2011/0178070 A1 | 7/2011 | Gong et al. |
| 2011/0195966 A1 | 8/2011 | Garcia-Echeverria et al. |
| 2011/0224223 A1 | 9/2011 | Shokat et al. |
| 2011/0312916 A1 | 12/2011 | Casebier |
| 2011/0312924 A1 | 12/2011 | Casebier |
| 2011/0313229 A1 | 12/2011 | Sugaya et al. |
| 2011/0319369 A1 | 12/2011 | Casebier et al. |
| 2012/0028972 A1 | 2/2012 | Wong et al. |
| 2012/0282331 A1 | 11/2012 | Chappel et al. |
| 2012/0292797 A1 | 11/2012 | Curatolo et al. |
| 2013/0130241 A1 | 5/2013 | Dehm |
| 2014/0288036 A1 | 9/2014 | Brodie et al. |
| 2014/0288037 A1 | 9/2014 | Casebier et al. |
| 2014/0343024 A1 | 11/2014 | Morrison et al. |
| 2014/0371181 A1 | 12/2014 | Casebier |
| 2015/0005265 A1 | 1/2015 | Stewart |
| 2015/0051179 A1 | 2/2015 | Casebier |
| 2015/0166599 A1 | 6/2015 | Morrison et al. |
| 2015/0174143 A1 | 6/2015 | Njar et al. |
| 2015/0203528 A1 | 7/2015 | Morrison et al. |
| 2015/0297615 A1 | 10/2015 | Njar et al. |
| 2015/0320770 A1 | 11/2015 | Casebier et al. |
| 2015/0361126 A1 | 12/2015 | Njar et al. |
| 2016/0000808 A1 | 1/2016 | Njar et al. |
| 2016/0002283 A1 | 1/2016 | Casebier et al. |

FOREIGN PATENT DOCUMENTS

| | | |
|---|---|---|
| EP | 0469548 A2 | 2/1992 |
| EP | 1712222 A2 | 10/2006 |
| EP | 0901786 B1 | 6/2007 |
| EP | 1530457 B1 | 9/2009 |
| GB | 972672 A | 10/1964 |

(56) References Cited

FOREIGN PATENT DOCUMENTS

| | | |
|---|---|---|
| GB | 2479337 A | 10/2011 |
| JP | 38-022578 | 10/1963 |
| JP | 56-003000 | 1/1981 |
| JP | 59-191000 A | 10/1984 |
| WO | WO-92/05179 A1 | 4/1992 |
| WO | WO-93/11130 A1 | 6/1993 |
| WO | WO-93/20097 A1 | 10/1993 |
| WO | WO-94/02136 A1 | 2/1994 |
| WO | WO-94/02485 A1 | 2/1994 |
| WO | WO-94/09010 A1 | 4/1994 |
| WO | WO-94/25626 A1 | 11/1994 |
| WO | WO-95/14023 A1 | 5/1995 |
| WO | WO-95/16691 A1 | 6/1995 |
| WO | WO-96/41807 A1 | 12/1996 |
| WO | WO-98/02441 A2 | 1/1998 |
| WO | WO-99/63974 A2 | 12/1999 |
| WO | WO-01/14387 A1 | 3/2001 |
| WO | WO-01/19828 A2 | 3/2001 |
| WO | WO-03/032950 A1 | 4/2003 |
| WO | WO-2005/009429 A1 | 2/2005 |
| WO | WO-2005/014023 A1 | 2/2005 |
| WO | WO-2005/047289 A1 | 5/2005 |
| WO | WO-2005/097107 A2 | 10/2005 |
| WO | WO-2006/093993 A1 | 9/2006 |
| WO | WO-2007/061737 A2 | 5/2007 |
| WO | WO-2007/064993 A2 | 6/2007 |
| WO | WO-2007/087395 A2 | 8/2007 |
| WO | WO-2008/027855 A2 | 3/2008 |
| WO | WO-2008/109163 A1 | 9/2008 |
| WO | WO-2008/154382 A1 | 12/2008 |
| WO | WO-2009/114658 A2 | 9/2009 |
| WO | WO-2009/120565 A2 | 10/2009 |
| WO | WO-2010/028646 A1 | 3/2010 |
| WO | WO-2010/089763 A2 | 8/2010 |
| WO | WO-2010/091299 A2 | 8/2010 |
| WO | WO-2010/091306 A1 | 8/2010 |
| WO | WO-2010/111132 A2 | 9/2010 |
| WO | WO-2011/017534 A2 | 2/2011 |
| WO | WO-2011/116344 A2 | 9/2011 |
| WO | WO-2012/129408 A2 | 9/2012 |
| WO | WO-2013/012959 A1 | 1/2013 |
| WO | WO-2013/079964 A1 | 6/2013 |
| WO | WO-2013/096907 A1 | 6/2013 |
| WO | WO-2015023710 A1 | 2/2015 |
| WO | WO-2016/172517 A1 | 10/2016 |

OTHER PUBLICATIONS

U.S. Appl. No. 14/635,415, filed Mar. 2, 2015, Morrison et al.
U.S. Appl. No. 14/635,469, filed Mar. 2, 2015, Morrison et al.
Abstract of NIH Grant Project Reference No. 2R01 CA27440-25A1, approximate submission date Feb. 18, 2004; approximate award date Sep. 23, 2004.
Abstract of NIH Grant Project Reference No. 3R01 CA27440-23S1, approximate date May 3, 2002; approximate award date Jun. 21, 2002.
Abstract of NIH Grant Project Reference No. 3R01 CA27440-24S1, approximate date Apr. 1, 2003; approximate award date Jun. 3, 2003.
Abstract of NIH Grant Project Reference No. 5R01 CA27440-23, approximate date Jan. 21, 2002; approximate award date Apr. 29, 2002.
Abstract of NIH Grant Project Reference No. 5R01 CA27440-24, approximate date Feb. 20, 2003; approximate award date Jun. 3, 2003.
Abstract of NIH Grant Project Reference No. 5R01 CA27440-26, approximate submission date Jul. 1, 2005; approximate award date Aug. 2, 2005.
Abstract of NIH Grant Project Reference No. 5R01 CA27440-27, approximate submission date Apr. 26, 2006.
Abstract of NIH Grant Project Reference No. 3R01 CA27440-22S1, approximate date Jun. 21, 2001; approximate award date Aug. 17, 2001.

Anderson, B. D. et al., Strategies in the Design of Solution-Stable, Water-Soluble Prodrugs 1: A Physical-Organic Approach to Pro-Moiety Selection for 21-Esters of Corticosteroids, Journal of Pharmaceutical Sciences, 75(4): 365-374 (1985).
Angelastro, M.R. et al., 17 beta-(cyclopropylamino)-androst-5-en-3 beta-ol, a selective mechanism-based inhibitor of cytochrome P450(17 alpha) (steroid 17 alpha-hydroxylase/C17-20 lyase), Biochemical and Biophysical Research Communications, 162(3):1571-1577 (1989).
Armstrong, A.J. et al., A pharmacodynamic study of rapamycin in men with intermediate to high risk localized prostate cancer: A Department of Defense Prosate Cancer Clinical Trials Consortium Trial, Clin. Cancer Res., 16(11):3057-66 (2010).
Auchus, R.J. et al., Use of Prednisone with Abiraterone Acetate in Metastatic Castration-Resistant Prostate Cancer, The Oncologist, 19: 1-10 (2014).
Ausubel, et al., Current Protocols in Molecular Biology (1987), Table of Content only.
Author Not Known, Definition of Poloxamer, Wikipedia.org, 3 pages, retrieved in May 1, 2014 <http://en.wikipedia.org/wiki/Poloxamer>.
Author Not Known, FDA approves Zytiga for late-stage prostate cancer, FDA News Release, U.S. Food and Drug Administration, 3 pages (Apr. 28, 2011), retrieved from the internet on Feb. 7, 2016 <http://www.fda.gov/NewsEvents/Newsroom/PressAnnouncements/ucm253055.htm>.
Author Not Known, Highlights of Prescribing Information for Lupron Depot, AbbVie Inc., Chicago, IL, Takeda Pharmaceutical Company, Japan, 26 pages, initial U.S. Approval: 1989, most recent update: 2014.
Author Not Known, Phase I Study of Palomid 529 a Dual TORC1/2 Inhibitor of the PI3K/Akt/mTOR Pathway for Advanced Neovascular Age-Related Macular Degeneration (P52901), ClinicalTrials.gov: A Service of the U.S. National Institutes of Health (2012), 3 pages, retrieved on Sep. 16, 2015 <https://clinicaltrials.gov/ct2/show/NCT01033721>.
Ayub, M. et al., Inhibition of testicular 17 alpha-hydroxylase and 17,20-lyase but not 3 beta-hydroxysteroid dehydrogenase-isomerase or 17 beta-hydroxysteroid oxidoreductase by ketoconazole and other imidazole drugs, Journal of Steroid Biochemistry, 28(5):521-531 (1987).
Baldo, P. et al., mTOR pathway and mTOR inhibitors as agents for cancer therapy, Curr. Cancer Drug Targets, 8(8):647-65 (2008). [Abstract Only].
Banks, P.K. et al., Regulation of ovarian steroid biosynthesis by estrogen during proestrus in the rat, Endocrinology, 129(3):1295-1304 (1991).
Barrie, S. E. et al., Pharmacology of novel steroidal inhibitors of cytochrome P450(17) alpha (17 alpha-hydroxylase/C17-20 lyase). J Steroid Biochem Mol Biol. 50:(5-6):267-273 (1994).
Barrie, S.E. et al., Inhibition of 17 alpha-hydroxylase/C17-C20 lyase by bifluranol and its analogues, Journal of Steroid Biochemistry, 33(6):1191-1195 (1989).
Beaumont, K. et al., Design of Ester Prodrugs to Enhance Oral Absorption of Poorly Permeable Compounds: Challenges to the Discovery Scientist, Current Drug Metabolism, 4:461-485 (2003).
Berge, et al., Pharmaceutical Salts, Journal of Pharmaceutical Sciences, 66(1): 1-17 (1977).
Brodie, A.M.H. et al., Inactivation of aromatase in vitro by 4-hydroxy-4-androstene-3,17-dione and 4-acetoxy-4-androstene-3,17-dione and sustained effects in vivo, Steroids, 38(6):693-702 (1981).
Brodie, A.M.H. et al., Studies on the mechanism of estrogen biosynthesis in the rat ovary—I, Journal of Steroid Biochemistry, 7(10):787-793 (1976).
Brodie, A.M.H. Steroidogenesis Pathway Enzymes—Section 9A Introduction, Design of Enzyme Inhibitors as Drugs vol. 2, M. Sandler and H.J. Smith, Oxford University Press, (Ch. 9):414-423 (1993).
Brodie, A.M.H., et al. Lack of evidence for aromatase in human prostatic tissues: effects of 4-hydroxyandrostenedione and other inhibitors on androgen metabolism, Cancer Research, 49(23):6551-6555 (1989).

(56) References Cited

OTHER PUBLICATIONS

Brodie, A.M.H., Inhibitors of Steroid Biosynthesis, Design of Enzyme Inhibitors as Drugs vol. 2, M. Sandler and H.J. Smith, Oxford University Press, (Ch.16):503-522 (1993).
Brodie, A.M.H., Steroidogenesis Pathway Enzymes—Aromatase Inhibitors, Design of Enzyme Inhibitors as Drugs vol. 2, M. Sandler and H.J. Smith, Oxford University Press, (Section 9B):424-436 (1993).
Bruchovsky, N. and Wilson, J., The conversion of testosterone to 5-alpha-androstan-17-beta-ol-3-one by rat prostate in vivo and in vitro. J Biol Chem. 243(8):2012-2021 (1968).
Bruno, R. D. et al., 17.alpha.-Hydroxylase/17,20 Lyase Inhibitor VN/124-1 Inhibits Growth of Androgen-independent Prostate Cancer Cells via Induction of theEndoplasmic Reticulum Stress Response, Molecular Cancer Therapeutics, 7 (9), 2828-2836 (2008).
Bruno, R.D. et al., Synthesis and biological evaluations of putative metabolically stable analogs of VN/124-1 (TOK-001): head to head anti-tumor efficacy evaluation of VN/124-1 (TOK-001) and abiraterone in LAPC-4 human prostate cancer xenograft model, Steroids, 76(12):1268-79 (2011).
Bruno, R.D. et al., Targeting cytochrome P450 enzymes: a new approach in anti-cancer drug development, Bioorganic & Medicinal Chemistry, 15(15):5047-5060 (2007).
Bulun, S.E. et al., Use of tissue-specific promoters in the regulation of aromatase cytochrome P450 gene expression in human testicular and ovarian sex cord tumors, as well as in normal fetal and adult gonads, The Journal of Clinical Endocrinology & Metabolism, 77(6):1616-1621 (1993).
Burkhart, J. P. et al., Inhibition of steroid C17(20) lyase with C-17-heteroaryl steroids. Bioorg Med Chem. 4(9):1411-1420 (1996).
Bühler, Pharmaceutical Technology of BASF Excipient, 3rd revised edition, pp. 6-164 (2008).
Carden, C.P. et al., Crossover pharmakokinetic (PK) study to assess oral administrative of abiraterone acetate capsule and tablet formulation in fasted and fed states in patients with prostate cancer, Journal of Clinical Oncology, 2008 ASCO Meeting Proceedings (Post-Meeting Edition) 26(15S):5168 (May 20 Supplement) (2008) [Abstract].
Castles, C.G. et al., Expression of a constitutively active estrogen receptor variant in the estrogen receptor-negative BT-20 human breast cancer cell line, Cancer Res., 53(24):5934-9 (1993).
Chang, S.S., Treatment options for hormone refractory prostate cancer, Rev. Urol., 9 (Suppl 2): S13-S18 (2007).
Chao, J. et al., A versatile synthesis of 17-heterosrylandrostenes via palladium-mediated Suzuki cross-coupling with heteroarylboronic acids, Steroids, 71(7):565-590 (2006).
Charvet, A-S. et al., Inhibition of Human Immunodeficiency Virus Type I Replication by Phosphonoformate- and Phosphonoacetate-2',3'-Dideoxy-3'-thiacytidine Conjugates, J. Med. Chem. 37:2216-2223 (1994).
Chaumeil, J. C., Micronization: A Method of Improving the Bioavailability of Poorly Soluble Drugs, Meth Find Exp Clin Pharmacol 20(3):211-215 (1998).
Chen, C. D. et al., Molecular determinants of resistance to antiandrogen therapy, Nat Med. 10(1):33-39 (2004).
Chengjie, R. et al., Syntheses and Pharmacological Activity of some 17-[2'substituted)-4'-pyrimidyl] androstene derivativies as inhibitors of human 17alpha-hydroxylase/C17,20-lyase., J. Chin. Pharm. Sci., 10(1): 3-8 (2001).
Chomczynski, P. and Sacchi, N., Single-step method of RNA isolation by acid guanidinium thiocyanate-phenol-chloroform extraction, Analytical Biochemistry, 162(1):156-159 (1987).
Choshi, T. et al., Total synthesis of grossularines-1 and -2. J. Org. Chem. 60:5899-5904 (1995).
Christensen, S.B. et al., Thapsigargin analogues for targeting programmed death of androgen-independent prostate cancer cells, Bioorganic & Medicinal Chemistry, 7(7):1273-1280 (1999).
Church, G.M. and Gilbert, W., Genomic sequencing, Proceedings of the National Academy of Sciences of the USA, 81(7):1991-1995 (1984).
Clement, O., et al., Three dimensional pharmacophore modeling of human CYP17 inhibitors. Potential agents for prostate cancer therapy, Journal of Medicinal Chemistry,46(12):2345-2351 (2003).
Coen, P. et al., An aromatase-producing sex-cord tumor resulting in prepubertal gynecomastia, The New England Journal of Medicine, 324(5):317-322 (1991).
Cohen, S.M. et al., Comparison of the effects of new specific azasteroid inhibitors of steroid 5 alpha-reductase on canine hyperplastic prostate: suppression of prostatic DHT correlated with prostate regression, The Prostate, 26(2):55-71 (1995).
Communication pursuant to Article 94(3) EPC for EP 10150763.0, 12 pages (Mar. 23, 2012).
Communication Pursuant to Article 94(3) EPC for EP 10704283.0, 9 pages (Nov. 6, 2012).
Coombes, R.C. et al., 4-Hydroxyandrostenedione treatment for postmenopausal patients with advanced breast cancer, Steroids, 50(1-3):245-252 (1987).
Corbishley, T.P. et al., Androgen Receptor in Human Normal and Malignant Pancreatic Tissue and Cell Lines, Cancer, 57:1992-1995 (1986).
Covey, D.F. et al., 10 beta-propynyl-substituted steroids. Mechanism-based enzyme-activated irreversible inhibitors of estrogen biosynthesis, The Journal of Biological Chemistry, 256(3):1076-1079 (1981).
Crawford, E. D. et al., A controlled trial of leuprolide with and without flutamide in prostatic carcinoma, New Eng J Med. 321:419-424 (1989).
Crawford, E.D. et al., Treatment of newly diagnosed stage D2 prostate cancer with leuprolide and flutamide or leuprolide alone, phase III: prognostic significance of minimal disease, J. Urol., Abstract from AUA Eighty-Seventh Annual Meeting, May 10-14, 1992, 147:417A (1992).
De Souza, et al. Enhancement of paclitaxel activity against hormone-refractory prostate cancer cells in vitro and in vivo by quinacrine. Br J Cancer 75 (11): 1593-600 (1997).
Declaration of Abdellah Sentissi under 37 C.F.R. 1.132 with exhibits, submitted in U.S. Appl. No. 14/233,335, 15 pages (Dec. 2, 2015).
Dehm, S.M. and Tindall, D.J., Alternatively spliced androgen receptor variants, Endocr. Relat. Cancer, 18(5):R183-96 (2011).
Dehm, S.M., et al., Splicing of a Novel Androgen Receptor Exon Generates a Constitutively Active Androgen Receptor that Mediates Prostate Cancer Therapy Resistance, Cancer Res., 68(13):5469-5477 (2008).
Denis, L., Role of maximal androgen blockade in advanced prostate cancer. The Prostate Supplement, 5:17-22 (1994).
Denmeade et al., A history of prostate cancer treatment, Nat. Rev. Cancer, 2(5):389-96 (2002).
Denmeade, S.R. and Isaacs, J.T., The SERCA pump as a therapeutic target: making a "smart bomb" for prostate cancer, Cancer Biology & Therapy, 4(1):14-22 (2005).
Di Salle, E. et al., Effects of 5 alpha-reductase inhibitors on intraprostatic androgens in the rat, The Journal of Steroid Biochemistry and Molecular Biology, 53(1-6):381-385 (1995).
Dihrendra, K. et al, Solid dispersions: a review, Pak. J. Pharm. Sci., 22(2):234-246 (2009).
Doorenbos, N. J. and Milewich, L., 17-beta-isoxazolyl and 17-beta-pyrazolyl steroids from 3-beta-hydroxy-21-formylpregn-5-en-20-one. Structural assignments, The Journal of Organic Chemistry, 31(10):3193-3199 (1966).
Dorwald, F.Z., Side Reactions in Organic Synthesis: A Guide to Successful Synthesis Design, Weinheim: WILEY-VCH Verlag GmbH and Co. KGaA, Preface, 4 pages (2005).
Duc, I. et al., In vitro and in vivo models for the evaluation of potent inhibitors of male rat 17alpha-hydroxylase/C17,20-lyase, J. Steroid. Biochem. Mol. Biol., 84(5):537-42 (2003).
Eisenhauer, et al. New response evaluation criteria in solid tumours: revises RECIST guideline (version 1.1), Eur. J. Cancer, 45(2): 228-47 (2009).
Elliott, G.B et al. Latent carcinoma of the prostate in a 24-year-old man receiving cyclophosphamide and azathioprine, Can. Med. Assoc. J., 116 (6):651-2 (1977).

(56) References Cited

OTHER PUBLICATIONS

Evans, B. E. et al., Methods for drug discovery: development of potent, selective, orally effective cholecystokinin antagonists. J Med Chem, 31(12):2235-2246 (1988).
Fedorak, et al. A novel colon-specific steroid prodrug enhances sodium chloride absorption in rat colitis. Am J Physiol. 269 (2 Pt 1): G210-218 (1995).
Feldman, B.J. et al., The development of androgen-independent prostate cancer, Nature Reviews Cancer, 1(1):34-45 (2001).
Ferraldeschi et al, Agents that Target Androgen Synthesis in Castration-Resistant Prostate Cancer., The Cancer J. 19(1) (2013).
Forti, G. et al., Three-month treatment with a long-acting gonadotropin-releasing hormone agonist of patients with benign prostatic hyperplasia: effects on tissue androgen concentration, 5 alpha-reductase activity and androgen receptor content, The Journal of Clinical Endocrinology & Metabolism, 68(2):461-468 (1989).
Frey, B.M. et al., Pharmacokinetics of 3 prednisolone prodrugs. Evidence of therapeutic inequivalence in renal transplant patients with rejection, Transplantation 39(3):270-274 (1985).
Frye, S.V. et al., 6-Azasteroids: potent dual inhibitors of human type 1 and 2 steroid 5 alpha-reductase, The Journal of Medicinal Chemistry, 36(26):4313-4315 (1993).
Frye, S.V. et al., 6-Azasteroids: structure-activity relationships for inhibition of type 1 and 2 human 5 alpha-reductase and human adrenal 3 beta-hydroxy-delta 5-steroid dehydrogenase/3-keto-delta 5-steroid isomerase, The Journal of Medicinal Chemistry, 37(15):2352-2360 (1994).
Frye, S.V. et al., Structure-activity relationships for inhibition of type 1 and 2 human 5 alpha-reductase and human adrenal 3 beta-hydroxy-delta 5-steroid dehydrogenase/3-keto-delta 5-steroid isomerase by 6-azaandrost-4-en-3-ones: optimization of the C17 substituent, The Journal of Medicinal Chemistry, 38(14):2621-2627 (1995).
Funke, R. et al., A Phase Ib/II Study Testing the Safety and Efficacy of Combined Inhibition of the PI3K/Akt and Androgen Receptor Signaling Pathways in Castration-resistant Prostate Cancer: GDC-0068 or GDC-0980 with Abiraterone Acetate Versus Abiraterone Acetate, Array Biopharma, TPS2616, 1 page (2012), retrieved on Sep. 25, 2012 <http://www.arraybiopharma.com/_documents/Publication/PubAttachment524.pdf>.
Gaddipati, J.P. et al., Frequent detection of codon 877 mutation in the androgen receptor gene in advanced prostate cancers, Cancer Research, 54(11):2861-2864 (1994).
Garde, D., Tokai Pharmaceuticals' Reformulated Galeterone Demonstrates Robust PSA Reductions in Advanced Prostate Cancer Patients, FierceBiotech, 2 pages, Jan. 2, 2014. URL: http://www.fiercebiotech.com/node/349034/print (Retrieved from the Internet Jul. 28, 2015).
Garrett, R. H. et al. [Editors]. Chapter 8: Lipids. Biochemistry (Second Edition). Saunders College Publishing. pp. 238-258 (1999).
Geller, J. et al., Comparison of prostatic cancer tissue dihydrotestosterone levels at the time of relapse following orchiectomy or estrogen therapy, The Journal of Urology, 132(4):693-696 (1984).
Gold, R. et al., Detection of DNA fragmentation in apoptosis: application of in situ nick translation to cell culture systems and tissue sections, Journal of Histochemistry & Cytochemistry, 41(7):1023-1030 (1993).
Goldman, A.S. et al., Production of male pseudohermaphroditism in rats by two new inhibitors of steroid 17alpha-hydroxylase and C 17-20 lyase, Journal of Endocrinology, 71(3):289-297 (1976).
Gomez-Orellana, I., Strategies to improve oral drug bioavailability, Expert Opinion on Drug Delivery, 2(3):419-433 (2005).
Goodin, et al. Effect of docetaxel in patients with hormone-dependent prostate-specific antigen progression after local therapy for prostate cancer, J. Clin. Oncol., 23(15):3352-7 (2005).
Gormley, G.J., Role of 5 alpha-reductase inhibitors in the treatment of advanced prostatic carcinoma, Urologic Clinics of North America, 18(1):93-98 (1991).
Goss, P.E. et al., Treatment of advanced postmenopausal breast cancer with an aromatase inhibitor, 4-hydroxyandrostenedione: phase II report, Cancer Research, 46(9):4823-4826 (1986).
Goya, S. et al., Studies on cardiotonic steroid analogs, V.: synthesis of 17β(or α)-isoxazolyl and pyrazolyl-16-methyl-14β(or α)-androst-5-enes, Yakugaku Zasshi, 90(5):537-543 (1970) [English Abstract Only].
Gravina, G.L. et al., The TORC1/TORC2 inhibitor, Palomid 529, reduces tumor growth and sensitizes to docetaxel and cisplatin in aggressive and hormone-refractory prostate cancer cells, Endocr. Relat. Cancer, 18(4):385-400 (2011).
Greene, et al., Protective Groups in Organic Synthesis, 2nd Ed. John Wiley and Sons (1991), Table of Content, 1991.
Griengl, H. et al. Phosphonoformate and phosphonoacetate derivatives of 5-substituted 2'-deoxyuridines: synthesis and antiviral activity, J. Med. Chem., 31(9):1831-1839 (1988).
Grigoryev, D. N. et al., Cytochrome P450c17-expressing *Escherichia coli* as a first-step screening system for 17alpha-hydroxylase-C17,20-lyase inhibitors, Analytical Biochem. 267(2):319-30 (1999).
Grigoryev, D. N. et al., Effects of new 17alpha-hydroxylase/C(17,20)-lyase inhibitors on LNCaP prostate cancer cell growth in vitro and in vivo. Br J Cancer. 81(4):622-630 (1999).
Guarna, A. et al., A concise route to 19-nor-10-azasteroids, a new class of steroid 5α-reductase inhibitors. 3.1 synthesis of (+)-19-nor-10-azatestosterone and (+)-17β-(acetyloxy)-(5β)-10-azaestr-1-en-3-one, The Journal of Organic Chemistry, 63(12):4111-4115 (1998).
Guo, Z. et al., A Novel Androgen Receptor Splice Variant Is Up-regulated during Prostate Cancer Progression and Promotes Androgen Depletion-Resistant Growth, Cancer Res., 69(6):2305-2313 (2009).
Gupta, E. et al., Changing Paradigms in Management of Metastatic Castration Resistant Prostate Cancer (mCRPC), Boston Medical Center Urology, 14(55):1-8 (2014).
Gülsün et al., Nanocrystal Technology for Oral Delivery of Poorly Water-Soluble Drugs, Fabad J. Pharm. Sci., 34:55-65 (2009).
Haase-Held, M. et al., The synthesis of 4-cyanoprogesterone: a potent inhibitor of the enzyme 5-α-reductase, Journal of the Chemical Society, Perkin Transactions 1, 22:2999-3000 (1992).
Habernicht, U.F. et al., Induction of estrogen-related hyperplastic changes in the prostate of the cynomolgus monkey (*Macaca fascicularis*) by androstenedione and its antagonization by the aromatase inhibitor 1-methyl-androsta-1,4-diene-3,17-dione, The Prostate, 11(4):313-326 (1987).
Haffner, C., Synthesis of 6-azacholesten-3-ones: potent inhibitors of 5alpha-reductase, Tetrahedron Letters, 36(23):4039-4042 (1995).
Haidar, S. et al. Effects of novel 17alpha-hydroxylase/C17, 20-lyase (P450 17, CYP 17) inhibitors on androgen biosynthesis in vitro and in vivo. J Steroid Biochem Mol Biol. 84(5):555-562 (2003).
Haidar, S. et al., Novel steroidal pyrimidyl inhibitors of P450 17 (17 alpha-hydroxylase/C17-20-lyase). Arch Pharm, Pharm Med. Chem 334(12):373-374 (2001).
Hakki, T. and Bernhardt, R., CYP17- and CYPIIB-dependent steroidhydroxylases as drug development targets, Pharmacology & Therapeutics, 111(1):27-52 (2006).
Hall, P. F., Cytochrome P-450 C21scc: one enzyme with two actions: hydroxylase and lyase. J Steroid Biochem Mol Biol. 40(4-6):527-532 (1991).
Hamilton, G.A., Chemical models and mechanisms for oxygenases, Molecular Mechanisms of Oxygen Activation, 1:405-451 (1974).
Hamm, R. et al., Patient self-injection: A new approach to administering luteinizing hormone-releasing hormone analogues, 86(7): 840-842 (2000).
Handratta, V. D. et al, Potent CYP17 inhibitors: improved syntheses, pharmacokinetics and anti-tumor activity in the LNCaP human prostate cancer model. J Steroid Biochem Mol Biol. 92(3):155-165 (2004).
Handratta, V. et al., Novel C-17-heteroaryl steroidal CYP17 inhibitors/antiandrogens: synthesis, in vitro biological activity, pharmacokinetics, and antitumor activity in the LAPC4 human prostate cancer xenograft model, Journal of Medicinal Chemistry, 48(8)2972-2984 (2005).

(56) References Cited

OTHER PUBLICATIONS

Harada, N., Novel properties of human placental aromatase as cytochrome P-450: purification and characterization of a unique form of aromatase, The Journal of Biochemistry, 103(1)106-113 (1988), Table of Content only.
Harlow, et al. Antibodies, a laboratory manual. 1988.
Hartley, T. et al., Endoplasmic reticulum stress response in an INS-1 pancreatic beta-cell line with inducible expression of a folding-deficient proinsulin, BMC Cell Biology, 11:59 (2010).
Hartmann, R. W. et al. Synthesis and evaluation of novel steroidal oxime inhibitors of P450 17 (17 alpha-hydroxylase/C17-20-lyase) and 5 alpha-reductase types 1 and 2. J Med Chem. 43(22):4266-4277 (2000).
Henderson, D. et al., Estrogens and benign prostatic hyperplasia: the basis for aromatase inhibitor therapy, 50(1-3):219-233 (1987).
Higuchi and Stella, V., Pro-drugs as novel drug delivery systems. American Chemical Soceity. ACS symposium series 14. (1975), Table of Content only.
Hochhaus, et al. A selective HPLC/RIA for dexamethasone and its prodrug dexamethasone-21-sulphobenzoate sodium in biological fluids, Biomed. Chromatogr., 6(6):283-6 (1992).
Hoehn, W. et al., Human prostatic adenocarcinoma: some characteristics of a serially transplantable line in nude mice (PC 82), The Prostate, 1(1):95-104 (1980).
Holt, D.A. et al., Inhibition of steroid 5 alpha-reductase by unsaturated 3-carboxysteroids, The Journal of Medicinal Chemistry, 33(3):943-950 (1990).
Hsiang, Y.H. et al., The influence of 4-hydroxy-4-androstene-3,17-dione on androgen metabolism and action in cultured human foreskin fibroblasts, Journal of Steroid Biochemistry, 26(1):131-135 (1987).
Hu, R. et al., Ligand-Independent Androgen Receptor Variants Derived from Splicing of Cryptic Exons Signify Hormone-Refractory Prostate Cancer, Cancer Res., 69(1):16-22 (2009).
Hudes, et al. Pacilitaxel plus estramustine in metastatic hormone-refractory prostate cancer. Seminars in Oncology Suppl.12, 22(5): 41-45 (1995).
Huggins, C. et al., Studies in prostate cancer: The effects of castration on advanced carcinoma of the prostate gland, Arch. Surg., 43(2):209-22 (1941), retrieved on Sep. 30, 2009 <www.archsurg.com>.
Humber, D. C. et al. Synthesis and biological activity of some cardiotonic compounds related to digitoxigenin. Steroids. 42(2):189-202 (1983).
Humez, S. et al., Role of endoplasmic reticulum calcium content in prostate cancer cell growth regulation by IGF and TNFalpha, Journal of Cellular Physiology, 201(2):201-213 (2004).
Hussain, et al. Docetaxel followed by hormone therapy after failure of definitive treatments for clinically localized/locally advanced prostate cancer; preliminary results. Seminars in Oncology, Suppl. 15, 28(4):22-31 (2001).
Hunyh, C., Fixation d'un Group Nitrile en Position 4 des Céto-3DELTA4-Stéroides, Bull. Soc. Chim. Fr., 4396 (1971), English Abstract.
Inkster, S. et al., Human testicular aromatase: immunocytochemical and biochemical studies, The Journal of Clinical Endocrinology & Metabolism, 80(6):1941-1947 (1995).
International Search Report and Written Opinion for PCT/US10/044570, 9 pages (dated Apr. 29, 2011).
International Search Report and Written Opinion for PCT/US2010/023391, 12 pages (dated Jun. 17, 2010).
International Search Report and Written Opinion for PCT/US2010/040448, 7 pages (dated Feb. 9, 2011).
International Search Report and Written Opinion for PCT/US2010/055996, 10 pages (dated Jul. 28, 2011).
International Search Report and Written Opinion for PCT/US2012/071485, 11 pages (dated Feb. 27, 2013).
International Search Report for PCT/US2006/007143, 1 page (dated Aug. 14, 2006).
International Search Report for PCT/US2009/036891, 3 pages (dated Oct. 7, 2009).
International Search Report for PCT/US2009/037610, 4 pages (dated Dec. 1, 2009).
International Search Report for PCT/US2010/023381, 7 pages (dated Sep. 6, 2010).
International Search Report for PCT/US2010/023387, 4 pages (dated May 7, 2010).
International Search Report for PCT/US2012/047253, 5 pages (dated Dec. 7, 2012).
International Search Report for PCT/US2016/028898, 3 pages (dated Jul. 12, 2016).
Ishibashi, K. et al., Synthesis of b-nor-4-aza-5α-androstane compound as 5α-reductase inhibitor, Bioorganic & Medicinal Chemistry Letters, 4(5):729-732 (1994).
Jain, et al. Food and oral antineoplastics: more than meets the eye. Clin Cancer Res. 16(17):4305-4307(2010). doi: 10.1158/1078-0432. CCR-10-1857. Epub Aug. 24. 2010.
Jarman, M. et al., Hydroxyperfluoroazobenzenes: novel inhibitors of enzymes of androgen biosynthesis, The Journal of Medicinal Chemistry, 33(9):2452-2455 (1990).
Jarman, M. et al., Inhibitors of enzymes of androgen biosynthesis: cytochrome P450(17) alpha and 5 alpha-steroid reductase. Nat Prod Rep. 15(5):495-512 (1998).
Jarman, M. et al., The 16,17-double bond is needed for irreversible inhibition of human cytochrome p45017a1pha by abiraterone (17-(3-pyridyl)androsta-5, 16-dien-3beta-ol) and related steroidal inhibitors, The Journal of Medicinal Chemistry, 41(27):5375-5381 (1998).
Jaworski, T., Degradation and beyond: control of androgen receptor activity by the proteasome system, Cell Mol. Biol. Lett., 11(1):109-31 (2006).
Jefcoate, C. R., Measurement of substrate and inhibitor binding to microsomal cytochrome P-450 by optical-difference spectroscopy. Methods Enzymol. 52:258-279 (1978).
Jemal, A. et al. Cancer statistics, 2004. CA cancer J. Clin. 54(1):8-29 (2004).
Junghanns, J.U. and Müller, R.H., Nanocrystal technology, drug delivery and clinical applications, Int. J. Nanomedicine., 3(3):295-309 (2008).
Kadar et al., Technical and safety aspects of blood and marrow transplantation using G-CSF mobilized family donors, Transfusion Science 17(4):611-618 (1996).
Kim, O. et al. Synergism of cytoplasmic kinases in IL6-induced ligand-independent activation of androgen receptor in prostate cancer cells. Oncogene. 23(10):1838-1844 (2004).
Kitz, R. and Wilson, I.B., Esters of methanesulfonic acid as irreversible inhibitors of acetylcholinesterase, The Journal of Biological Chemistry 237(10):3245-3249 (1962).
Klein, K. A. et al. Progression of metastatic human prostate cancer to androgen independence in immunodeficient SCID mice. Nat Med. 3(4):402-406 (1997).
Klus, G.T. et al., Growth inhibition of human prostate cells in vitro by novel inhibitors of androgen synthesis, Cancer Research, 56(21):4956-4964 (1996).
Kozák, I. et al., Nuclei of stroma: site of highest estrogen concentration in human benign prostatic hyperplasia, The Prostate, 3(5):433-438 (1982).
Krieg, M. et al., Stroma of human benign prostatic hyperplasia: preferential tissue for androgen metabolism and oestrogen binding, Acta Endocrinologica (Copenhagen), 96(3):422-432 (1981).
Kuppens, I.E.L.M. et al., Oral bioavailability of docetaxel in combination with OC144-093 (ONT-093), Cancer Chemother. Pharmacol., 55: 72-78 (2005).
Kwegyir-Afful, A. K. et al., Clinical canidate galeterone (VN/124-1 or TOK-001) induces the degradation of full-length and splice variant androgen receptors in human prostate cancer cell lines via PI3K-Akt-M dm2 pathway: implications for prostate cancer therapy, Cancer Research, vol. 73, No. 8, suppl. 1, pp. 4PP (2013), Abstract only.
Kyprianou, N. and Isaacs, J.T., Expression of transforming growth factor-beta in the rat ventral prostate during castration-induced programmed cell death, Molecular Endocrinology, 3(10):1515-1522 (1989).

(56) References Cited

OTHER PUBLICATIONS

Kyprianou, N. et al., Programmed cell death during regression of PC-82 human prostate cancer following androgen ablation, Cancer Research, 50(12):3748-3753 (1990).
Labrie, F. et al., Combination therapy for prostate cancer. Endocrine and biologic basis of its choice as new standard first-line therapy, Cancer Suppl. 3, 71:1059-1067 (1993).
Lai, E. et al., Endoplasmic reticulum stress: signaling the unfolded protein response, Physiology (Bethesda, Md.), 22(3):193-201 (2007).
Laneri, et al. Ionized prodrugs of dehydroepiandrosterone for transdermal iontophoretic delivery, Pharm. Res., 16(12): 1818-24 (1999).
Larsen, J.D. and Bundgaard, H., Prodrug forms for the sulfonamide group. I. Evaluation of N-acyl derivatives, N-sulfonylamidines, N-sulfonylsulfilimines and sulfonylureas as possible prodrug derivatives, Int. J. Pharmaceutics, 37:87-95 (1987).
Larsen, J.D. et al., Prodrug forms for the sulfonamide group. II. Water-soluble amino acid derivatives of N-methylsulfonamides as possible prodrugs, Int. J. Pharmaceutics, 47:103-110 (1988).
Li, J. et al., 4-pregnene-3-one-20β-carboxaldehyde: a potent inhibitor of 17α-hydroxylase/c17,20-lyase and of 5α-reductase, The Journal of Steroid Biochemistry and Molecular Biology, 42(3-4):313-320 (1992).
Li, J. et al., Inhibition of androgen synthesis by 22-hydroximino-23,24-bisnor-4-cholen-3-one, The Prostate, 26(3):140-150 (1995).
Li, J. et al., Synthesis and evaluation of pregnane derivatives as inhibitors of human testicular 17 alpha-hydroxylase/C17,20-lyase, The Journal of Medicinal Chemistry, 39(21):4335-4339 (1996).
Li, T.H. et al., A promoting role of androgen receptor in androgen-sensitive and -insensitive prostate cancer cells, Nucleic Acids Res., 35(8):2767-76 (2007).
Libertini, S.J. et al., Evidence for Calpain-Mediated Androgen Receptor Cleavage as a Mechanism for Androgen Independence, Cancer Res, 67(19):9001-9005 (2007).
Ling, Y.Z. et al., 17-Imidazolyl, pyrazolyl, and isoxazolyl androstene derivatives. Novel steroidal inhibitors of human cytochrome C17,20-lyase (P450(17 alpha), The Journal of Medicinal Chemistry, 40(20):3297-3304 (1997).
Long, B.J. et al., Antiandrogenic effects of novel androgen synthesis inhibitors on hormone-dependent prostate cancer, Cancer Research, 60(23):6630-6640 (2000).
Long, B.J. et al., In vitro and in vivo inhibition of LNCaP prostate cancer cell growth by novel inhibitors of androgen synthesis, Proceedings of the American Association for Cancer Research, 90th Annual Meeting, Apr. 10-14, 1999, vol. 40, Abstract #423 (1999).
Lu, Q. et al., Expression of aromatase protein and messenger ribonucleic acid in tumor epithelial cells and evidence of functional significance of locally produced estrogen in human breast cancers, Endocrinology, 137(7):3061-3068 (1996).
Maggiolini, et al. The mutant androgen receptor T877A mediates the proliferative but not the cytotoxic dose-dependent effects of genistein and quercetin on human LNCaP prostate cancer cells, Molecular Pharmacology, 62(5):1027-1035 (2002).
Matsunaga, N. et al. C(17,20)-lyase inhibitors. Part 2: design, synthesis and structure-activity relationships of (2-naphthylmethyl)-1H-imidazoles as novel C(17,20)-lyase inhibitors. Bioorg Med Chem. 12(16):4313-4336 (2004).
Matsunaga, N. et al. C17,20-lyase inhibitors I. Structure-based de novo design and SAR study of C17,20-lyase inhibitors. Bioorg Med. Chem. 12(9):2251-2273 (2004).
Matsunaga, N. et al. Synthetic studies on (1S)-1-(6,7-dimethoxy-2-naphthyl)-1-(1H-imidazol-4-yl)-2-methylpropan-1-o-1 as a selective C17,20-lyase inhibitor. Tetrahedron: Asymmetry. 15:2021-2028 (2004).
Mawhinney, M.G. and Belis, J.A., Androgens and estrogens in prostatic neoplasia, Advances in Sex Hormone Research, 2:141-209 (1976).
McCague, R. et al., Inhibition of enzymes of estrogen and androgen biosynthesis by esters of 4-pyridylacetic acid, The Journal of Medicinal Chemistry, 33(11):3050-3055 (1990).

McConnell, J. D., Physiologic basis of endocrine therapy for prostatic cancer. Urol Clin North Am. 18(1):1-13 (1991).
McDonald, I.A. et al., Inhibition of steroid 5-alpha-reductase by "inverted" competitive inhibitors, Bioorganic and Medicinal Chemistry Letters, 4(6):847-851 (1994).
McLeod, et al. A glucocorticoid prodrug facilitates normal mucosal function in rat colitis without adrenal suppression, Gastroenterology, 106(2):405-13 (1994).
Metcalf, B.W. et al., Substrate-induced inactivation of aromatase by allenic and acetylenic steroids, Journal of the American Chemical Society, 103(11):3221-3222 (1981).
Mohler, J. L. et al., The androgen axis in recurrent prostate cancer. Clin Cancer Res. 10(2):440-448 (2004).
Montgomery, R.B. et al., Galeterone in men with CRPC: results in four distinct patient populations from the ARMOR2 study, Abstract #5029, Poster, Presented at the 50th Annual Meeting of the American Society of Clinical Oncology (ASCO), Chicago, Illinois (May 30, 2014-Jun. 3, 2014).
Moreira, V. et al. Synthesis and evaluation of novel 17-indazole androstene derivatives designed as CYP17 inhibitors, Steroids 72(14):939-948 (2007).
Moreira, V.M. et al., CYP17 inhibitors for prostate cancer treatment—an update, Curr. Med. Chem., 15(9):868-99 (2008) [Abstract Only].
Muscato, J. J. et al., Optimal dosing of ketoconazole (KETO) and hydrocortisone (HC) leads to long responses in hormone refractory prostate cancer, Thirtieth Annual Meeting of the Americal Society of Clinical Oncology, May 14-17, 1994, vol. 13, p. 229, Abstract 701 (1994).
Nakajin, S. and Hall, P.F., Microsomal cytochrome P-450 from neonatal pig testis. Purification and properties of A C21 steroid side-chain cleavage system (17 alpha-hydroxylase-C17,20 lyase), The Journal of Biological Chemistry, 256(8):3871-3876 (1981).
Nakajin, S. et al., Inhibitory effects and spectral changes in pig testicular cytochrome P-450(17 alpha-hydroxylase/lyase) by 20 beta-hydroxy-C21-steroids, Yakugaku Zasshi (Journal of the Pharmaceutical Society of Japan), 108(12):1188-1195 (1988) [English Abstract Only].
Nakajin, S. et al., Microsomal cytochrome P-450 from neonatal pig testis: two enzymatic activities (17 alpha-hydroxylase and c17,20-lyase) associated with one protein, Biochemistry, 20(14):4037-4042 (1981).
Nawrocki, S.T. et al., Bortezomib sensitizes pancreatic cancer cells to endoplasmic reticulum stress-mediated apoptosis, Cancer Research, 65(24):11658-11666 (2005).
Nicolaou, K. C. et al., Natural Product-like Combinatorial Libraries Based on Privileged Structures. 1. General Principles and Solid-Phase Synthesis of Benzopyrans, J. Am. Chem. Soc. 122(41):9939-9953 (2000).
NIH Grant Project Reference No. 2R01 CA27440-24A1, 2R01 CA27440-25A1 Revised Grant Renewal Application, approximate submission date Feb. 18, 2004; approximate award date Sep. 23, 2004, SAI.MD04. 02 12-5610-360221, 51 pages, signed Feb. 18, 2004.
NIH Grant Project Reference No. 3R01 CA27440-22S1 Grant Application for Supplemental Funding, approximate date Jun. 21, 2001; approximate award date Aug. 17, 2001, SAI:MD01:06 20-5504-360221, 31 pages, received Jun. 21, 2001, signed Jun. 14, 2001.
NIH Grant Project Reference No. 3R01 CA27440-23S1 Grant Continuation Application and Progress Report, approximate date May 3, 2002; approximate award date Jun. 21, 2002, MD01-0220-5807-360221, 3 pages, signed May 3, 2002.
NIH Grant Project Reference No. 5R01 CA27440-23 Grant Continuation Application and Progress Report, approximate date Jan. 21, 2002; approximate award date Apr. 29, 2002, SAI.MD02 17-5787-360221, 7 pages, signed Jan. 21, 2002.
NIH Grant Project Reference No. 5R01 CA27440-24 Grant Continuation Application and Progress Report, approximate date Feb. 20, 2003; approximate award date Jun. 3, 2003. CA27440-24, signed Apr. 1, 2003.
NIH Grant Project Reference No. 5R01 CA27440-24S1 Grant Continuation Application and Progress Report, 11 pages, approximate date Apr. 1, 2003; approximate award date Jun. 3, 2003.

(56) References Cited

OTHER PUBLICATIONS

NIH Grant Project Reference No. 5R01 CA27440-25 Grant Renewal Application, 39 pages, approximate submission date Jun. 26, 2003—Unfunded.
NIH Grant Project Reference No. 5R01 CA27440-26 Grant Renewal Continuation Application and Progress Report, approximate submission date Jul. 1, 2005; approximate award date Aug. 2, 2005, CA27440-26, 7 pages, signed Jul. 1, 2005.
NIH Grant Project Reference No. 5R01 CA27440-27 ESNAP Report, 9 pages, approximate submission date May 8, 2006.
NIH Grant Project Reference No. 5R01 CA27440-27 Grant Continuation Application and Progress Report, approximate submission date Apr. 26, 2006, CA27440-27, signed Apr. 26, 2006.
Nishimura, et al. Effects of flutamide as a second-line agent for maximum androgen blockade of hormone refractory prostate cancer. Int J Urol. 14(3):264-267 (2007).
Njar, V. and Brodie, A., Inhibitors of 17alpha-hydroxylase/17,20-lyase (CYP17): potential agents for the treatment of prostate cancer, Curr Pharm Des. 5(3):163-180 (1999).
Njar, V. et al., Novel 17-azolyl steroids, potent inhibitors of human cytochrome 17 alpha-hydroxylase-C17,20-lyase (P450(17) alpha): potential agents for the treatment of prostate cancer, J Med Chem. 41(6):902-912 (1998).
Njar, V. et al., Nucleophilic vinylic "addition-elimination" substitution reaction of 3.beta.-acetoxy-17-chloro-16-formylandrosta-5,16-diene: A novel and general route to 17-substituted steroids. Part 1—synthesis of novel 17-azolyl-.DELTA..sup.16steroids; inhibitors of 17.alpha.-hydroxylase/17,20-lyase (17.alpha.-lyase), Bioorganic & Medicinal Chemistry Letters, 6(22): 2777-2782 (1996).
Njar, V.C. and Brodie, A.M., Discovery and development of Galeterone (TOK-001 or VN/124-1) for the treatment of all stages of prostate cancer, J. Med. Chem., 58(5):2077-87 (2015).
Njar, V.C. et al., Synthesis of novel 21-trifluoropregnane steroids: inhibitors of 17 alpha-hydroxylase/17,20-lyase (17 alpha-lyase), Steroids, 62(6):468-473 (1997).
Njar, V.C.O. et al., Novel 10β-aziridinyl steroids; inhibitors of aromatase, Journal of the Chemical Society, Perkin Transactions 1, 10:1161-1168 (1993).
Nnane, I. P. et al., Effects of novel 17-azolyl compounds on androgen synthesis in vitro and in vivo. J Steroid Biochem Mol Biol. 71(3-4):145-152 (1999).
Nnane, I.P. et al., Effects of some novel inhibitors of C17,20-lyase and 5alpha-reductase in vitro and in vivo and their potential role in the treatment of prostate cancer, Cancer Res., 58(17):3826-32 (1998).
O'Donnell, A. et al. Hormonal impact of the 17alpha-hydroxylase/C(17,20)-lyase inhibitor abiraterone acetate (CB7630) in patients with prostate cancer. Br J Cancer. 90(12):2317-2325 (2004).
Ojida et al., Stereocontrolled synthesis of (1S)-1-(1H-imidazol-4-yl)-1-(6-methoxy-2-naphthyl)-2-methylpropan-1-ol as a potent C.sub.17,20-lyase inhibitor, Tetrahedron: Asymmetry, 15: 1555-1559 (2004).
Okudaira, N. et al., A study of the intestinal absorption of an ester-type prodrug, ME3229, in rats: active efflux transport as a cause of poor bioavailability of the active drug, J. Pharmacol. Exp. Ther., 294(2):580-7 (2000).
Onoda, M. et al., Affinity alkylation of the active site of C21 steroid side-chain cleavage cytochrome P-450 from neonatal porcine testis: a unique cysteine residue alkylated by 17-(bromoacetoxy)progesterone, Biochemistry, 26(2):657-662 (1987).
Pappo, R. and Chorvat, R.J., The synthesis of 2-azasteroids, Tetrahedron Letters, 13(31):3237-3240 (1972).
Partial European Search Report for EP 10150763.0, 6 pages (dated Jul. 16, 2010).
Pataki, J. and Jensen, E.V., Synthesis of fluorinated 3beta-hydroxypregn-5-en-20-one derivatives, Steroids, 28(4):437-447 (1976).
Pelc, B. and Hodková, J., Androstane derivatives substituted by pyrazole ring in position 17, Collection of Czechoslovak Chemical Communications, 34(2):442-450 (1969).
Petrow, V. and Lack, L., Studies on a 5-alpha-Reductase Inhibitor and Their Therapeutic Implications, The Prostate Cell: Structure and Function, Part B, pp. 283-297 (1981).
Picard, F. et al., Synthesis and evaluation of 2'-substituted 4-(4'-carboxy- or 4'-carboxymethylbenzylidene)-N-acylpiperidines: highly potent and in vivo active steroid 5alpha-reductase type 2 inhibitors. J Med Chem. 45(16):3406-3417 (2002).
Potter, G. A. et al., A convenient, large-scale synthesis of abiraterone acetate [3B-acetoxy-17-(3-pryidyl)androsta-5,16-diene], a potential new drug for the treatment of prostate cancer. Organic Preparations and Procedures Int. 29(1):123-134 (1997).
Potter, G.A. et al., Novel Steroidal Inhibitors of Human Cytochrome P450.sub.17.alpha.(17.alpha.-Hydroxylase-C.sub.17,20-lyase): Potential Agents for the Treatment of Prostatic Cancer, J. Med. Chem., 38(13): 2463-2471 (1995).
Purushottamachar Puranik et al., Systematic Structure Modifications of Multitarget Prostate Cancer Drug Candidate Galeterone to Produce Novel Androgen Receptor Down-Regulating Agents- as an Approach to Treatment of Advanced Prostate Cancer, Journal of Medicinal Chemistry, vol. 56, No. 12, 4880-4898 (2013).
Purushottamachar, P. et al., Exploitation of Multi-target Prostate Cancer Clinical Candidate VN/124-1 (TOK-001) to Develop a Novel Class of Androgen Receptor Down Regulating Agents for Prostate Cancer Therapy, Poster, 242nd ACS National Meeting, Aug. 28-Sep. 1, 2011, Paper ID: 11268, 1 page (Aug. 28, 2011).
Purushottamachar, P. et al., Systematic Structure Modifcations of Multi-target Prostate Cancer Drug Candidate Galeterone to Produce Novel Androgen Receptor Donw-regulating Agents as an Approach to Treatment of Advanced Prostate Cancer, Journal of Medicinal Chemistry, 19 pages (2013).
Rahmani, M. et al. The kinase inhibitor sorafenib induces cell death through a process involving induction of endoplasmic reticulum stress, Molecular and Cellular Biology, 27(15):5499-5513 (2007).
Randimbivololona, F. and Lesne, M., Metabolism and excretion in bile of SC4453, a new semi-synthetic derivative of digoxin following an i.v. bolus injection in the guinea-pig. J. Pharmacol. 15(1):53-64 (1984).
Rasmusson, G.H. and Toney, J.H., Therapeutic Control of Androgen Action, Annual Reports in Medicinal Chemistry, 29(23):225-232 (1994).
Rasmusson, G.H. et al., Azasteroids as inhibitors of rat prostatic 5 alpha-reductase, The Journal of Medicinal Chemistry, 27(12):1690-1701 (1984).
Rasmusson, G.H. et al., Azasteroids: structure-activity relationships for inhibition of 5 alpha-reductase and of androgen receptor binding, The Journal of Medicinal Chemistry, 29(11):2298-2315 (1986).
Recanatini, M. et al., A new class of nonsteroidal aromatase inhibitors: design and synthesis of chromone and xanthone derivatives and inhibition of the P450 enzymes aromatase and 17 alpha-hydroxylase/C17,20-lyase. Med Chem. 44(5):672-680 (2001).
Reid, et al. CYP17 inhibition as a hormonal strategy for prostate cancer. Nat Clin Pract Urol. 5(11): 610-20 (2008).
Remington: The Science and Practice of Pharmacy, Nineteenth Ed., Mack Publishing Co., Easton, Pennsylvania, (1995), Table of Content only.
Rittmaster, R.S. et al., Differential effect of 5 alpha-reductase inhibition and castration on androgen-regulated gene expression in rat prostate, Molecular Endocrinology, 5(7):1023-1029 (1991).
Roche. Bioreversible Carriers in Drug Design, American Pharmaceutical Association and Pergamon Press, 1987, Table of Content.
Ron, D. and Walter, P., Signal integration in the endoplasmic reticulum unfolded protein response, Nature Reviews Molecular Cell Biology, 8(7):519-529 (2007).
Russell, D.W. and Wilson, J.D., Steroid 5 alpha-reductase: two genes/two enzymes, Annual Review of Biochemistry, 63:25-61 (1994).
Ryan, C.J. et al., Phase I clinical trial of the CYP17 inhibitor abiraterone acetate demonstrating clinical activity in patients with castration-resistant prostate cancer who received prior ketoconazole therapy, J. Clin. Oncol., 28(9):1481-8 (2010).
Saad, et al. The Canadian Uro-Oncology Group multicentre phase II study of docetaxel administered every 3 weeks with prednisone in men with metastatic hormone-refractory prostate cancer progress-

(56) References Cited

OTHER PUBLICATIONS ing after mitoxantrone/prednisone. BJU Int. Aug. 5, 2008; 102 (5); 551-5, doi: 10.1111/j.1464-410X.2008.07733.x Epub May 28.
Saulnier, et al. An efficient method for the synthesis of guanidino prodrugs. Bioorganic and Medicinal Chemistry Letters, 4(16):1985-1990 (1994).
Schayowtz, A. et al., Prolonging hormone sensitivity in prostate cancer xenografts through dual inhibition of AR and mTOR, Br. J. Cancer, 103(7):1001-7 (2010).
Schayowitz, et al. Synergistic effect of a novel antiandrogen, VN/124-1, and signal transduction inhibitors in prostate cancer progression of hormone independence in vitro. Mol. Cancer Ther., 7(1):121-132 (2008).
Schayowitz. Synergistic effect of anti-androgens and signal transduction inhibitors in prostate cancer progression, University of Maryland Baltimore Thesis, 186 pages (2008).
Schieweck, K. et al., Anti-tumor and endocrine effects of non-steroidal aromatase inhibitors on estrogen-dependent rat mammary tumors, The Journal of Steroid Biochemistry and Molecular Biology, 44(4-6):633-636 (1993).
Schwarzel, W.C. et al., Studies on the mechanism of estrogen biosynthesis. 8. The development of inhibitors of the enzyme system in human placenta, Endocrinology, 92(3):866-880 (1972).
Shao, T.C. et al., Effects of finasteride on the rat ventral prostate, Journal of Andrology, 14(2):79-86 (1993).
Shearer, R. and Davies, J.H., Studies in Prostatic Cancer with 4-Hydroxyandrostenedione, 4-hydroxyandrostenedione—A new approach to hormone-dependent cancer, Royal Society of Medicine Services, Limited, Ed. Coombes, R.C. and Dowsett, M., Royal Society of Medicine Services International Congress and Symposium Series No. 180, pp. 41-44 (1991).
Simmons, et al. Combined androgen blockade revisited: emerging options for the treatment of castration-resistant prostate cancer. Urology, 73(4): 697-705 (2009).
Sinkula, J.A. and Yalkowsky, S.H., Rationale for design of biologically reversible drug derivatives: prodrugs, J. Pharm. Sci., 64(2):181-210 (1975).
Sjoerdsma, A., Suicide enzyme inhibitors as potential drugs, Clinical Pharmacology & Therapeutics, 30(1):3-22 (1981).
Skryma, R. et al., Store depletion and store-operated Ca2+ current in human prostate cancer LNCaP cells: involvement in apoptosis, The Journal of Physiology, 527(Pt 1):71-83 (2000).
Small, E. J. et al. Ketoconazole retains activity in advanced prostate cancer patients with progression despite flutamide withdrawal. J Urol. 157(4):1204-1207 (1997).
Snider, C.E. and Brueggemeier, R.W., Covalent modification of aromatase by a radiolabeled irreversible inhibitor, Journal of Steroid Biochemistry, 22(3):325-330 (1985).
Souillac et al., Characterization of Delivery Systems, Differential Scanning Calorimetry in Encyclopedia of Controlled Drug Delivery, John Wiley & Sons, 212-227 (1999).
Stanbrough, M. et al., Increased expression of genes converting adrenal androgens to testosterone in androgen-independent prostate cancer, Cancer Res., 66(5):2815-25 (2006).
Stangelberger, et al. The combination of antagonists of LHRH with antagonists of GHRH improves inhibition of androgen sensitive MDA-PCa-2b and LuCaP-35 prostate cancers. Prostate, 67(12):1339-1353 (2007).
STN Registry No. 851983-85-2, CAS Registry, 1 page, entered STN Jun. 9, 2005.
Stoner, E., The clinical development of a 5 alpha-reductase inhibitor, finasteride, The Journal of Steroid Biochemistry and Molecular Biology 37(3):375-378 (1990).
Szendi, Z. et al., Steroids, LIII: new routes of aminosteroids[1], Monatshefte für Chemie Chemical Monthly, 127(11):1189-1196 (1996).
Tepper, C.G. et al., Characterization of a Novel Androgen Receptor Mutation in a Relapsed CWR22 Prostate Cancer Xenograft and Cell Line, Cancer Research, 62:6606-6614 (2002).

Thompson T. A. and Wilding, G., Androgen antagonist activity by the antioxidant moiety of vitamin E, 2,2,5,7,8-pentamethyl-6-chromanol in human prostate carcinoma cells. Mol Cancer Ther. 2(8):797-803 (2003).
Tindall, D. et al., Symposium on androgen action in prostate cancer. Cancer Res. 64(19):7178-7180 (2004).
Trachtenberg, J. et al. Ketoconazole: a novel and rapid treatment for advanced prostatic cancer. J Urol. 130(1):152-153 (1983).
Trachtenberg, J., Ketoconazole therapy in advanced prostatic cancer, The Journal of Urology, 132(1):61-63 (1984).
Tran, C. et al., Development of a second-generation antiandrogen for treatment of advanced prostate cancer, Science, 324(5928):787-90 (2009).
Tunn, U.W. et al., Comparison of LH-RH analogue 1-month depot and 3-month depot by their hormone levels and pharmacokinetic profile in patients with advanced prostate cancer, 60(Suppl. 1): 9-17 (1998).
Vakatkar, V.V. et al., Cleavage of steriodal oximes, semicarbazones and thiosemicarbazones with titanous chloride under mild conditions, Abstract, Chemistry and Industry, Society of Chemical Industry, London,17: 742 (1977).
Van Steenbrugge, G.J. et al., Transplantable human prostatic carcinoma (PC-82) in athymic nude mice. III. Effects of estrogens on the growth of the tumor tissue, The Prostate, 12(2):157-171 (1988).
Vasaitis T. S. et al., Novel, potent anti-androgens of therapeutic potential: recent advances and promising developments, Future Medicinal Chemistry, Future Science Ltd., GB, VI. 2, No. 3, 667-680 (2010).
Vasaitis, T. et al., Androgen receptor inactivation contributes to antitumor efficacy of CYP17 inhibitor VN/124-1 in prostate cancer, Molecular Cancer Therapeutics,7(8): 2348-2357 (2008).
Vasaitis, T. et al., The Effects of Novel Anti-Androgens on Androgen Receptor Action and Expression, Proceedings of the American Association for Cancer Research 47, Abstract 5340 (2006)http://aacrmeetingabstracts.org/cgi/content/abstract/2006/1/252-d.
Vasaitis, T.S. et al., CYP17 inhibitors for prostate cancer therapy, J. Steroid Biochem. Mol. Biol., 125(1-2):23-31 (2011).
Vehring. Pharmaceutical particle engineering via spray drying. Pharm Res. May 2008;25(5):999-1022. Epub Nov. 28, 2007.
Veldscholte, J. et al., Anti-androgens and the mutated androgen receptor of LNCaP cells: differential effects on binding affinity, heat-shock protein interaction, and transcription activation, Biochemistry, 31(8):2393-2399 (1992).
Veldscholte, J. et al., The androgen receptor in LNCaP cells contains a mutation in the ligand binding domain which affects steroid binding characteristics and response to antiandrogens, J. Steroid. Biochem. Mol. Biol., 41(3-8):665-9 (1992).
Vescio, R.A. et al., Cancer biology for individualized therapy: correlation of growth fraction index in native-state histoculture with tumor grade and stage, Proceedings of the National Academy of Sciences of the USA, 87(2):691-695 (1990).
Vippagunta, S. R. et al., Crystalline solids. Adv Drug Deliv Rev. 48(1):3-26 (2001).
Visakorpi, T. et al., In vivo amplification of the androgen receptor gene and progression of human prostate cancer, Nature Genetics 9(4):401-406 (1995).
Voets, M. et al., Heteroaryl-substituted naphthalenes and structurally modified derivatives: selective inhibitors of CYP11B2 for the treatment of congestive heart failure and myocardial fibrosis. J Med Chem. 48(21):6632-6642 (2005).
Wainstein M.A. et al., CWR22: androgen-dependent xenograft model derived from a primary human prostatic carcinoma, Cancer Research, 54(23):6049-6052 (1994).
Weintraub, P.M. et al., Chemical Abstract No. 116:214776V for EP 0469547, Chemical Abstracts Service, American Chemical Society, Columbus, OH, 116(22):778 (1992).
Weintraub, P.M. et al., Chemical Abstract No. 117 for EP0469-548 A2, Steroids, 117:985 (1992).
Wicha, J. and Masnyk, M., Cardiotonic Steroids, Part 8., Synthesis of 17beta-(3'-Pyridyl)-14beta-androst-4-ene-3beta, 14-diol from 17-Oxandrostane Derivatives, Bulletin of the Polish Academy of Sciences, Chemistry, 33(1-2):19-27 (1985).

(56) References Cited

OTHER PUBLICATIONS

Wilkinson, G.R., Chapter One: Pharmacokinetics, The Dynamics of Drug Absorption, Distribution, and Elimination, Goodman and Gilman's The Pharmaological Basis of Therapeutics, 10th Supp. Edition, 2 pages (2001).

Williams, G. et al., Objective responses to ketoconazole therapy in patients with relapsed progressive prostatic cancer, British Journal of Urology, 58(1):45-51 (1986).

Written Opinion for PCT/US2006/007143, 4 pages (dated Aug. 14, 2006).

Written Opinion for PCT/US2009/037610, 5 pages (dated Dec. 1, 2009).

Written Opinion for PCT/US2012/047253, 9 pages (dated Dec. 7, 2012).

Written Opinion for PCT/US2016/028898, 5 pages (dated Jul. 12, 2016).

Wu, J. and Kaufman, R.J., From acute ER stress to physiological roles of the Unfolded Protein Response, Cell Death & Differentiation, 13(3):374-384 (2006).

Yen, W.C. et al., Differential effect of taxol in rat primary and metastatic prostate tumors: site-dependent pharmacodynamics, Pharmaceutical Research, 13(9):1305-1312 (1996).

Yue, W. et al., A new nude mouse model for postmenopausal breast cancer using MCF-7 cells transfected with the human aromatase gene, Cancer Research, 54(19):5092-5095 (1994).

Yue, W., et al. Effect of aromatase inhibitors on growth of mammary tumors in a nude mouse model, Cancer Research, 55(14):3073-3077 (1995).

Zenger, M. et al., Structure-Activity Relationship and Drug Design, Remington's Pharmaceutical Sciences (Sixteenth Edition), Mack Publishing, Chapter 27: 420-425 (1980).

Zhang, J. et al. A small composite probasin promoter confers high levels of prostate-specific gene expression through regulation by androgens and glucocorticoids in vitro and in vivo. Endocrinology. 141(12):4698-4710 (2000).

Zhao, Z. et al., Modified Taxols, 6. Preparation of Water-Soluble Prodrugs of Taxol, Journal of Natural Products, 54(6): 1607-1611 (1991).

Zheng, J.Y. and Fulu, M., Decrease of genital organ weights and plasma testosterone levels in rats following oral administration of leurpolide microemulsion, International Journal of Pharmaceutics, 307: 209-215 (2006).

Zhou, J.L. and Brodie, A., The effect of aromatase inhibitor 4-hydroxyandrostenedione on steroid receptors in hormone-dependent tissues of the rat, The Journal of Steroid Biochemistry and Molecular Biology, 52(1):71-76 (1995).

Zhou, Z.X. et al., The androgen receptor: an overview, Recent Prog. Horm. Res., 49:249-74 (1994).

Zhuang, Q.Y. et al., [Effects of rapamycin on prostate cancer PC-3 cells], Ai Zheng, 28(8):851-5 (2009) [English Abstract Only].

C-17-HETEROARYL STEROIDAL CYP17 INHIBITORS/ANTIANDROGENS, IN VITRO BIOLOGICAL ACTIVITIES, PHARMACOKINETICS AND ANTITUMOR ACTIVITY

This application is a continuation of U.S. patent application Ser. No. 14/081,910, filed Nov. 15, 2013, which is a continuation of U.S. patent application Ser. No. 12/577,090, filed Oct. 9, 2009, which is a divisional application of U.S. patent application Ser. No. 11/817,550, filed Mar. 14, 2008, which is the national stage entry of PCT Application No. PCT/US2006/007143, filed Mar. 2, 2006, which claims the benefit of the filing date of U.S. Provisional Application Ser. No. 60/657,390 filed Mar. 2, 2005, which is incorporated by reference herein.

The U.S. Government has a paid-up license in this invention and the right in limited circumstances to require the patent owner to license others on reasonable terms as provided for by the terms of Grant No. CA027440 awarded by the National Institutes of Health (NIH).

The present invention provides new chemical entities, particularly steroidal C-17 benzoazoles, pyrimidinoazoles (azabenzoazoles) and diazines. It is also provides methods for the synthesis of the benzoazoles, pyrimidinoazoles and diazines. In one embodiment, the methods for synthesizing benzoazoles or pyrimidinoazoles comprise a step of nucleophilic vinylic "addition-elimination" substitution reaction of 3β-acetoxy-17-chloro-16-formylandrosta-5,16-diene or analogs thereof and benzoazole or pyrimidinoazole nucleophiles. In another embodiment, the methods for synthesizing diazines comprise a palladium catalyzed cross-coupling reaction of 17-iodoandrosta-5,16-dien-3β-ol or analogs thereof with tributylstannyl diazines.

Compounds of the present invention are potent inhibitors of human CYP17 enzyme as well as potent antagonists of both wild type and mutant androgen receptors (AR). The most potent CYP17 inhibitors were: 3β-hydroxy-17-(1H-benzimidazole-1-yl)androsta-5,16-diene (5, code named VN/124-1), 3β-hydroxy-17-($5^1$-pyrimidyl)androsta-5,16-diene (15) and 17-(1H-benzimidazole-1-yl)androsta-4,16-diene-3-one (6), with $IC_{50}$ values of 300, 500 and 915 nM, respectively. Compounds 5, 6, 14 and 15 were effective at preventing binding of $^3$H-R1881 (methyltrienolone, a stable synthetic androgen) to both the mutant and LNCaP AR and the wild-type AR, but with a 2.2 to 5-fold higher binding efficiency to the latter. Compounds 5 and 6 were also shown to be potent pure AR antagonists. The cell growth studies showed that 5 and 6 inhibit the growth of DHT-stimulated LNCaP and LAPC4 prostate cancer cell with $IC_{50}$ values in the low micromolar range (i.e., <10 μM). Their inhibitory potencies were comparable to that of CASODEX® (bicalutamide) but remarkably superior to that of flutamide. The pharmacokinetics of compounds 5 and 6 in mice was investigated. Following s.c. administration of 50 mg/kg of 5 and 6, peak plasma levels of 16.82 and 5.15 ng/mL, respectively occurred after 30 to 60 min, both compounds were cleared rapidly from plasma (terminal half-lives of 44.17 and 39.93 min, respectively) and neither was detectable at 8 h. Remarkably, compound 5 was rapidly converted into a metabolite tentatively identified as 17-(1H-benzimidazol-1-yl)androsta-3-one. When tested in vivo, 5 proved to be very effective at inhibiting the growth of androgen-dependent LAPC4 human prostate tumor xenograft, while 6 was ineffective. Compound 5 (50 mg/kg/twice daily) resulted in a 93.8% reduction (P=0.00065) in the mean final tumor volume compared with controls, and it was also significantly more effective than castration. To our knowledge, this is the first example of an anti-hormonal agent (an inhibitor of androgen synthesis (CYP17 inhibitor)/antiandrogen) that is significantly more effective than castration in suppression of androgen-dependent prostate tumor growth. In view of these impressive anti-cancer properties, compound 5 and others can be used for the treatment of human prostate cancer.

Prostate cancer (PCA) is the most common malignancy and age-related cause of cancer death worldwide. Apart from lung cancer, PCA is the most common form of cancer in men and the second leading cause of death in American men. In the United States this year (2004), an estimated 230,000 new case of prostate cancer will be diagnosed and about 23,000 men will die of this disease (Jemal et al., Cancer Statistics, 2004. *CA Cancer J. Clin.*, 2004, 54, 8-29). During the period of 1992 to 1999, the average annual incidence of PCA among African American men was 59% higher than among Caucasian men, and the average annual death rate was more than twice that of Caucasian men (American Cancer Society—Cancer Facts and Figures 2003). Androgens play an important role in the development, growth, and progression of PCA (McConnell, J. D., "Physiological basis of endocrine therapy for prostatic cancer", *Urol. Clin. North Am.*, 1991, 18: 1-3). The two most important androgens in this regard are testosterone (T) and dihydrotestosterone (DHT). The testes synthesize about 90% of T and the rest (10%) is synthesized by the adrenal glands. T is further converted to the more potent androgen DHT by the enzyme steroid 5α-reductase that is localized primarily in the prostate (Bruchovsky et al., "The conversion of testosterone to 5α-androstan-17β-ol-3-one by rat prostate in vivo and in vitro", *J. Biol. Chem.*, 1968, 243, 2012-2021). Huggins et al. introduced androgen deprivation as therapy for advanced and metastatic PCA in 1941 (Huggins et al. "Studies on prostatic cancer: 2. The effects of castration on advanced carcinoma of the prostate gland.", *Arch. Surg.*, 1941, 43, 209-212). Thereafter, androgen ablation therapy has been shown to produce the most beneficial responses in multiple settings in PCA patients (Denmeade et al. "A history of prostate cancer treatment." *Nature Rev. Cancer*, 2002, 2: 389-396). Orchidectomy (either surgical or medical with a GnRH agonist) remains the standard treatment option for most prostate cancer patients. Medical and surgical orchidectomy reduces or eliminates androgen production by the testes but does not affect androgen synthesis in the adrenal glands. Several studies have reported that a combination therapy of orchidectomy with antiandrogens, to inhibit the action of adrenal androgens, significantly prolongs the survival of PCA patients (Crawford, et al., "A controlled trial of leuprolide with and without flutamide in prostatic carcinoma", *N. Engl. J Med*, 1989, 321, 419-424; Crawford, et al., "Treatment of newly diagnosed state D2 prostate cancer with leuprolide and flutamide or leuprolide alone, Phase III: intergroup study 0036", *J. Urol.*, 1992, 147: 417A; and Denis, L., "Role of maximal androgen blockade in advanced prostate cancer", *Prostate*, 1994, 5 (Suppl.), 17s-22s). In a recent featured article by Mohler and colleagues (Mohler et al., "The androgen axis in recurrent prostate cancer", *Clin. Cancer Res.*, 2004, 10, 440-448) it was clearly demonstrated that T and DHT occur in recurrent PCA tissues at levels sufficient to activate androgen receptor. In addition, using microarray-based profiling of isogenic PCA xenograft models, Sawyer and colleagues (Chen et al., "Molecular determinants of resistance to antiandrogen therapy." *Nat. Med.*, 2004, 10, 33-39) found that a modest increase in androgen receptor mRNA was the only change consistently associated with the development of resistance to antiandrogen therapy.

Potent and specific compounds that inhibit androgen synthesis in the testes, adrenals, and other tissue may be more effective for the treatment of PCA (Njar, V. C. O.; Brodie, A. M. H., "Inhibitors of 17α-hydroxylase-$C_{17,20}$-lyase (CYP17): Potential agents for the treatment of prostate cancer", *Current Pharm. Design*, 1999, 5: 163-180).

In the testes and adrenal glands, the last step in the biosynthesis of T involves two key reactions, which act sequentially and they are both catalyzed by a single enzyme, the cytochrome P450 monooxygenase 17α-hydroxylase/17, 20-lyase (CYP17) (Hall, P. F., "Cytochrome P-450 $C_{21\ scc}$: one enzyme with two actions: Hydroxylase and lyase", *J. Steroid Biochem. Molec. Biol.*, 1991, 40, 527-532). Ketoconazole, as an antifungal agent and by virtue of inhibiting P450 enzymes, is also a modest CYP17 inhibitor and has been used clinically for the treatment of PCA (Trachtenberg et al., "Ketoconazole: A novel and rapid treatment for advanced prostatic cancer", *J. Urol.* 1983, 130, 152-153). It is reported that careful scheduling of treatment can produce prolonged responses in otherwise hormone-refractory prostate cancer patients (Muscato et al., "Optimal dosing of ketoconazole and hydrocortisone leads to long responses in hormone refractory prostate cancer", *Proc. Am. Assoc. Cancer Res.*, 1994, 13: 22 (Abstract)). Furthermore, ketoconazole was found to retain activity in advanced PCA patients with progression despite flutamide withdrawal (Small et al., "Ketoconazole retains activity in advanced prostate cancer patients with progression despite flutamide withdrawal", *J. Urol.*, 1997, 157, 1204-1207). Although, ketoconazole has now been withdrawn from use because of liver toxicity and other side effects this suggests that more potent and selective inhibitors of CYP17 could provide useful agents for treating this disease, even in advanced stages and in some patients who may appear to be hormone refractory.

A variety of potent steroidal and non-steroidal inhibitors of CYP17 have been reported and some have been shown to be potent inhibitors of testosterone production in rodent models (Njar and Brodie, above). Recently, Jarman and colleagues have described the hormonal impact of their most potent CYP17 inhibitor, abiraterone in patients with prostate cancer (O'Donnell et al., "Hormonal impact of the 17α-hydroxylase/C17,20-lyase inhibitors abiraterone acetate (CB7630) in patients with prostate cancer", *Br. J. Cancer*, 2004, 90: 2317-2325). Some of our potent CYP17 inhibitors have been shown to also inhibit 5α-reductase and/or are potent antiandrogens with potent antitumor activity (Njar and Brodie, above, and Long et al., "Antiandrogenic effects of novel androgen synthesis inhibitors on hormone-dependent prostate cancer." *Cancer Res.*, 2000, 60, 6630-6640). Further illustrative of the background of the invention are U.S. Pat. Nos. 5,994,335; 6,200,965; and, 6,444,683.

We have discovered a series of potent CYP17 inhibitors/antiandrogens, the 17-benzoazoles, 17-pyrimidinoazoles and 17-diazines (see, e.g., Schemes 1 and 2, for examples of preparation of compounds which can be analogously applied to other structures, as described below). The stimulus for preparing these C-17 heteroaryl steroids was based on our desire to incorporate benzimidazole, benzotriazole, pyrimidinoazole and diazine moieties, so-called "privileged substructures" (Nicolaou et al., "Natural product-like combinatorial libraries based on privileged structures. 1. General principles and solid-phase synthesis of benzopyrans", *J. Am. Chem. Soc.*, 2000, 122, 9939-9953. "Privileged structures", a term originally introduced by Evans et al. (*J. Med. Chem.*, 1988, 31, 2235-2246) to describe structural motifs capable of interacting with a variety of unrelated molecular targets) in the new molecules. These scaffolds, especially the benzimidazole scaffold, continue to receive extensive attention in medicinal chemistry because of their diverse portfolio of biological activities and also as entities of a variety of useful drugs (Nicolaou et al., above).

The C-17 heteroaryl steroid compounds of the invention are of the following general formula I:

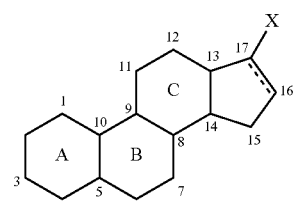

wherein:
the ABC ring structure is the A, B and C ring portions of a steroid or analog thereof, which are optionally substituted;
the === bond at the 16, 17 position is a double bond or, when the compound is 17-(1H-benzimidiazol-1-yl)androst-3-one, a single bond; and
X is an optionally substituted benzimidazole, benzotriazole, pyrimidinoimidazole (purine), pyrimidinotriazole or diazine; the benzimidazole, benzotriazole, and pyrimidinoimidazole groups being bonded to the steroid residue through a nitrogen atom on the 5-membered ring; and, the diazine groups being bonded to the steroid residue through a carbon atom on the diazine ring.

Pharmaceutically acceptable salts of these compounds are also included in the invention.

The optional substitution for the ABC ring structure includes one or more of: alkyl and halogenated alkyl (preferably $C_{1-6}$); alkenyl and halogenated alkenyl (preferably $C_{1-6}$) including where the double bond is directly attached to the ring structure; halogen; amino; aminoalkylene; hydroxyimino; and hydroxy. Further optionally, hydrogen substituents on adjacent carbon atoms of the ABC ring structure may be removed and replaced by an additional bond between the adjacent carbon atoms to result in a double bond between these carbons in the ring structure. Preferred optional substitutions on the ABC ring structure are methyl groups at the 10 and/or 13 positions of the ring structure.

The optional substitution for the benzimidazole, benzotriazole, pyrimidinoimidazole, pyrimidinotriazole or diazine structures include halogen, amino, aminoalkylene, hydroxy, —SH, —S-alkyl, alkyl and halogenated alkyl (preferably $C_{1-6}$). These optional substituents will be on ring carbon atoms of the benzimidazole, benzotriazole, pyrimidinoimidazole, pyrimidinotriazole or diazine structures.

The benzimidazole, benzotriazole, pyrimidinoimidazole, pyrimidinotriazole or diazine structures are of the following formulae, respectively:

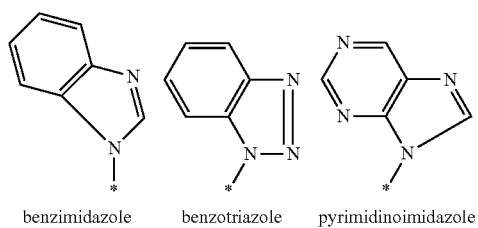

benzimidazole     benzotriazole     pyrimidinoimidazole

-continued

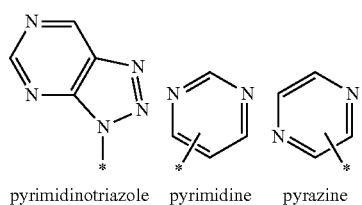

pyrimidinotriazole  pyrimidine  pyrazine wherein the * indicates the point of attachment to the steroid residue.

In one preferred embodiment, the ABC ring structure has a C ring which has no substitution except for preferably alkyl, particularly methyl, substitution at the carbon shared with the D ring which is adjacent the attachment to the C-17 heteroaryl substitution, i.e., the 13-position.

In another preferred embodiment, the A, B and C rings of the ABC ring structure have a conventional structure based on 3β-hydroxy-androsta-5,16-diene or 3-oxo-androsta-5,16-diene. But in another embodiment the A and B rings have one of the following structures 1-25:

1
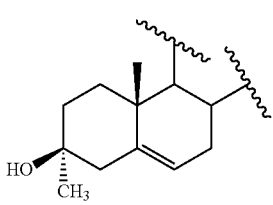

2
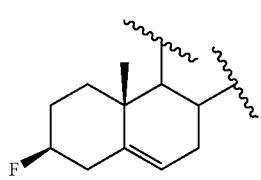

3
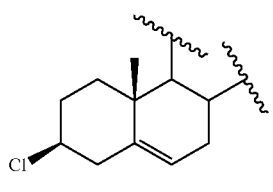

4
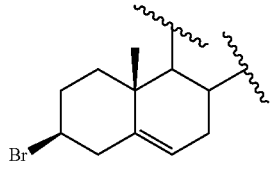

5
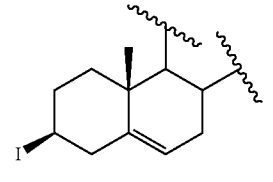

-continued

6
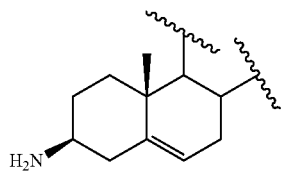

7
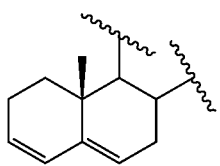

8
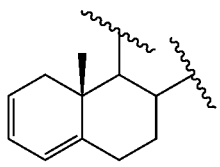

9
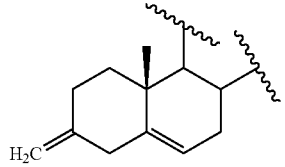

10
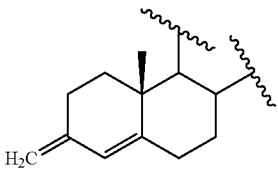

11
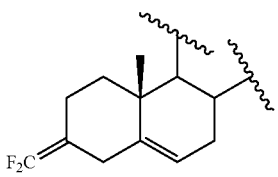

12
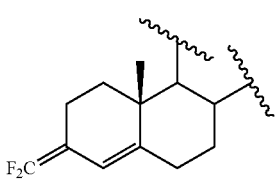

13
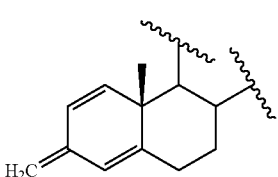

14
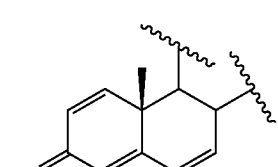

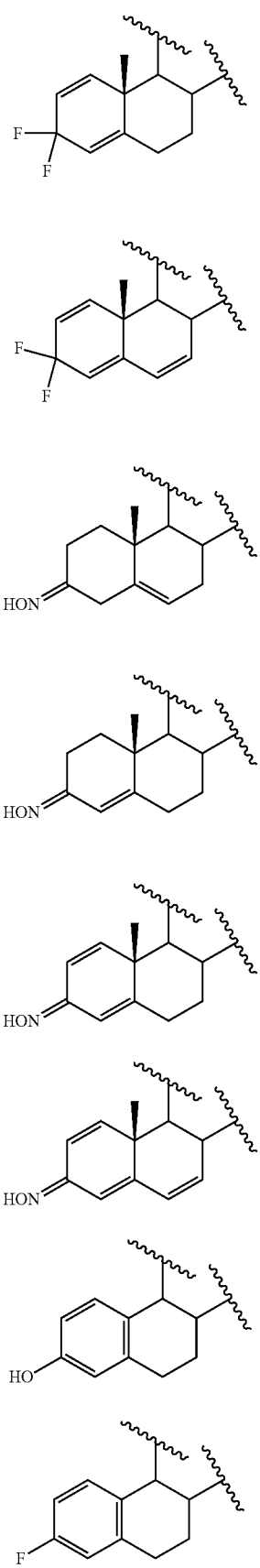
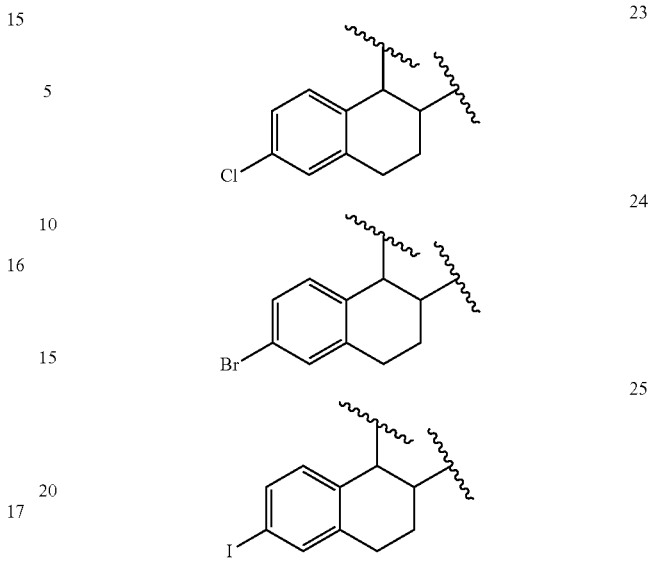

The following lists the chemical names of compounds having the AB rings as in 1-25, and the C and D rings conventional, wherein X is benzimidazole. Analogous compounds wherein X is benzotriazole, pyrimidinoimidazole, pyrimidinotriazole, pyrazine or pyrimidine are also contemplated.

Compound 1: 3β-Hydroxy-3α-methyl-17-(1H-benzimidazol-1-yl)-androsta-5,16-diene

Compound 2: 3β-Fluoro-17-(1H-benzimidazol-1-yl)-androsta-5,16-diene

Compound 3: 3β-Chloro-17-(1H-benzimidazol-1-yl)-androsta-5,16-diene

Compound 4: 3β-Bromo-17-(1H-benzimidazol-1-yl)-androsta-5,16-diene

Compound 5: 3β-Iodo-17-(1H-benzimidazol-1-yl)-androsta-5,16-diene

Compound 6: 3β-Amino-17-(1H-benzimidazol-1-yl)-androsta-5,16-diene

Compound 7: 17-(1H-benzimidazol-1-yl)-androsta-3,5,16-triene

Compound 8: 17-(1H-benzimidazol-1-yl)-androsta-2,4,16-triene

Compound 9: 17-(1H-benzimidazol-1-yl)-3-methyleneandrosta-5,16-triene

Compound 10: 17-(1H-benzimidazol-1-yl)-3-methyleneandrosta-4,16-triene

Compound 11: 3,3-Difluoro-17-(1H-benzimidazol-1-yl)-androsta-5,16-diene

Compound 12: 3,3-Difluoro-17-(1H-benzimidazol-1-yl)-androsta-4,16-diene

Compound 13: 17-(1H-benzimidazol-1-yl)-3-methyleneandrosta-2,4,16-triene

Compound 14: 17-(1H-benzimidazol-1-yl)-3-methyleneandrosta-2,4,6,16-tetraene

Compound 15: 3,3-Difluoro-17-(1H-benzimidazol-1-yl)-androsta-2,4,16-triene

Compound 16: 3,3-Difluoro-17-(1H-benzimidazol-1-yl)-androsta-2,4,6,16-tetraene

Compound 17: 3-Hydroxyimino-17-(1H-benzimidazol-1-yl)-androsta-5,16-diene

Compound 18: 3-Hydroxyimino-17-(1H-benzimidazol-1-yl)-androsta-4,16-diene

Compound 19: 3-Hydroxyimino-17-(1H-benzimidazol-1-yl)-androsta-2,4,16-triene

Compound 20: 3-Hydroxyimino-17-(1H-benzimidazol-1-yl)-androsta-2,4,6,16-diene

Compound 21: 3-Hydoxy-17-(1H-benzimidazol-1-yl)-estra-1,3,5(10),16-tetraene

Compound 22: 3-Fluoro-17-(1H-benzimidazol-1-yl)-estra-1,3,5(10),16-tetraene

Compound 23: 3-Chloro-17-(1H-benzimidazol-1-yl)-estra-1,3,5(10),16-tetraene

Compound 24: 3-Bromo-17-(1H-benzimidazol-1-yl)-estra-1,3,5(10),16-tetraene

Compound 25: 3-Iodo-17-(1H-benzimidazol-1-yl)-estra-1,3,5(10),16-tetraene

Examples of optional substituents for the heteroaryl ring, X, are shown by the following structures 26-40 wherein X is benzimidazole. Analogous compounds wherein X is substituted benzotriazole, pyrimidinoimidazole, pyrimidinotriazole, pyrazine or pyrimidine are also contemplated.

26
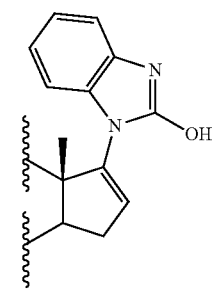

27
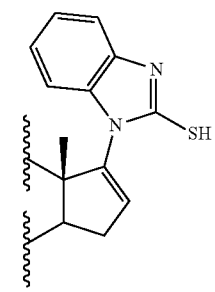

28
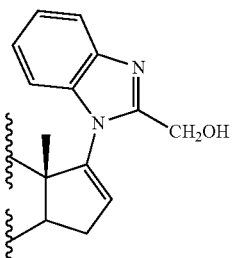

29
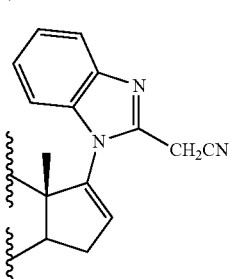

30
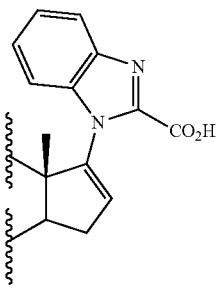

31
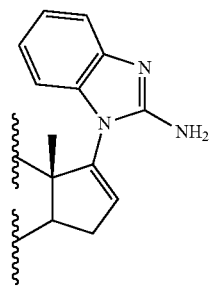

32
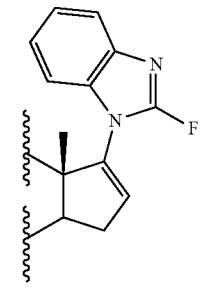

33
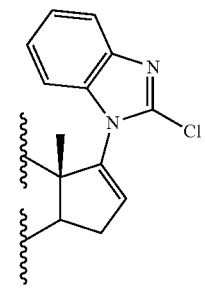

34
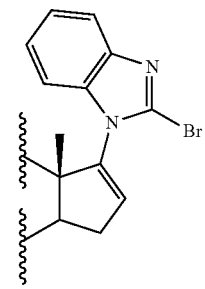

35 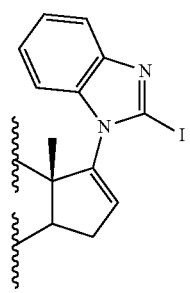
36 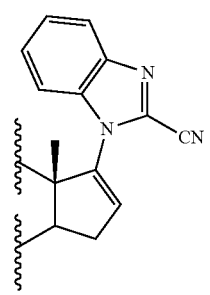
37 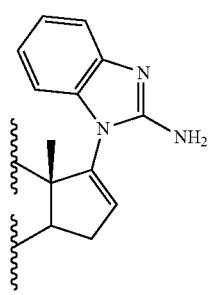
38 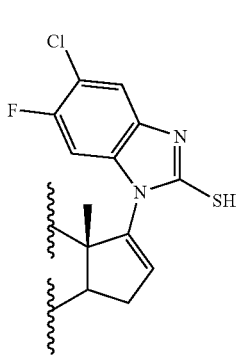
39 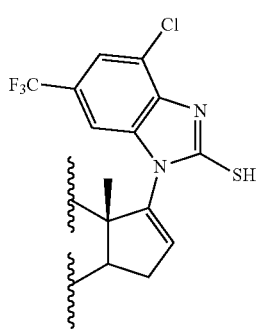
40 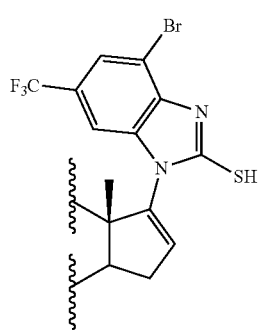
Other examples of optional substituents for the heteroaryl ring, X, are shown by the following structures 41-46 wherein X is substituted C-17-azabenzimidazole (i.e., pyrimidinoimidazole or purine). Analogous compounds wherein X is substituted benzimidazole, benzotriazole, pyrimidinotriazole, pyrazine or pyrimidine are also contemplated.
41 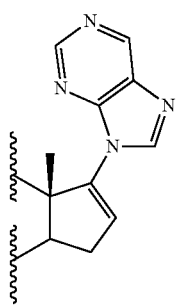
42 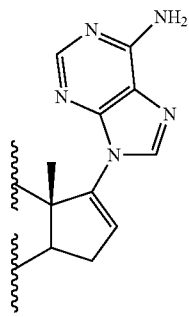
43 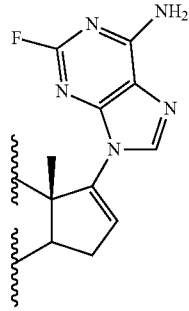

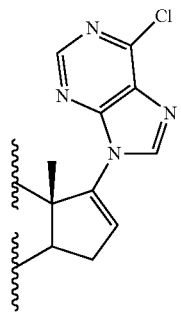

44

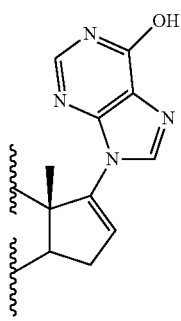

45

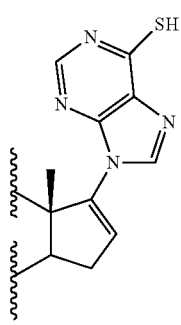

46

Particularly preferred compounds are those of the following structures M5, M6, M9 and M10.

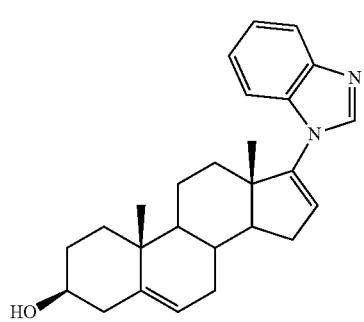

M5

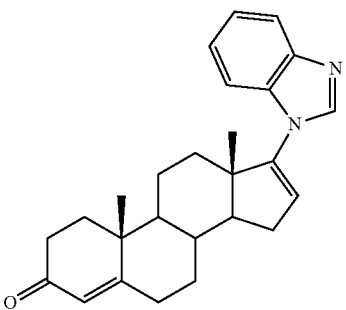

M6

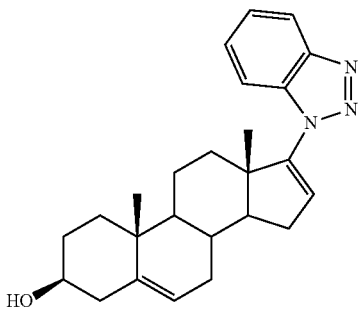

M9

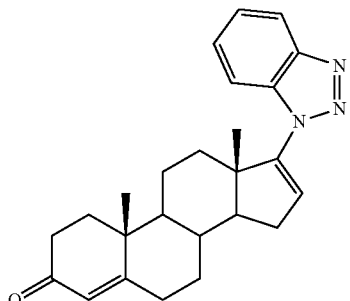

M10

The inhibitory activities of these compounds compared to CYP17 and steroid 5α-reductases, the binding to and transactivation of androgen receptors, and their antiproliferative effects against two human prostate cancer cell lines, LNCaP and LAPC-4 were studied. The pharmacokinetics of compounds 5 and 6 were evaluated in mice and the in vivo antitumor activities against human LAPC-4 prostate carcinoma were also evaluated in mice. To our knowledge, all the compounds described here, with the exception of compound 15 represent novel entities (Haidar et al., "Novel steroidal pyrimidyl inhibitors of P450 17 (17α-hydroxylase/C17-20-lyase)", *Arch. Pharm. Med. Chem.*, 2001, 334, 373-374; and Haidar et al., "Effects of novel 17α-hydroxylase/C17,20-lyase (P45017, CYP17) inhibitors on androgen biosynthesis in vitro and in vivo", *Steroid Biochem, Molec. Biol.*, 2003, 84, 555-562).

The preparation of the new 17-benzoazoles and 17-diazines is outlined in Schemes 1 and 2, respectively. These methods can be applied analogously to other analogs described herein.

The key intermediate in our synthesis of the 17-benzazoles, 3β-acetoxy-17-chloro-16-formylandtrosta-5,16-dine (2) was obtained from (1) by our routine procedure as previously described (Njar et al., "Nucleophilic vinylic "addition-elimination" substitution reaction of 3β-acetoaxy-17-chloro-16-formylandrosta-5,16-diene: A novel and general route to 17-substituted-Δ$^{16}$-steroids. Part 1. Synthesis of novel 17-azolyl-$\Delta^{16}$ steroids; inhibitors of 17α-hydroxylase/ 17,20-lyase (P450$_{17\alpha}$)", *Bioorg. Med. Chem. Lett.,* 1996, 6, 2777-2782; and "Novel 17-azolyl steroids; potent inhibitors of cytochrome P450 17α-hydroxylase/17,20-lyase (P450$_{17\alpha}$): Potential agents for the treatment of prostate cancer", *J. Med. Chem.,* 1998, 41, 902-912). Treatment of 2 with benzimidazole in the presence of K$_2$CO$_3$ in DMF at approximately 80° C. gave the desired 3β-acetoxy-17-1H-benzimidazole 3 in near quantitative yield. Compound 3 was smoothly deformylated with 10% palladium on activated charcoal in refluxing benzonitrile to give compound 4 in 93% yield, from which hydrolysis gave the required 3β-hydroxy 17-benzimidazole 5. Modified Oppenauer oxidation of 5 afforded the corresponding $\Delta^4$-3-oxo analog, 6.

The reaction of 2 with benzotriazole in the presence of K$_2$CO$_3$ in DMF at approximately 80° C. gave the desired 3β-acetoxy-17-benzo-1H-1,2,3-triazole 7b in excellent yield, together with the 2H-1,2,3-triazole regioisomer 7a in approx. 5% yield. These two regioisomers were readily separated by flash column chromatography (FCC) on silica gel and were also easily identified by their respective proton NMR spectra. Thus, the four aromatic protons of the symmetrical 2H-1,2,3-triazole 7a appeared as two pairs of doublets at δ 7.43, 7.45, 7.88 and 7.90 while the four aromatic protons of the unsymmetrical 1H-1,2,3-triazole 7b appear as multiplet at δ 7.46 (2H) and doublets at δ 7.57 (1H) and 8.15 (1H), respectively. In addition, the 16-CHO proton in 7a was significantly shifted downfield to δ 10.66 compared to that in 7b at δ 9.59. Deformylation of 7b with in situ generation of Rh(1,3-bis(diphenylphosphino)propane)$_2$$^+$Cl$^-$ catalyst [Rh(dppp)$_2$$^+$Cl$^-$] in refluxing xylenes gave compound 8, and following hydrolysis of the 3β-acetoxy group, we obtained the target 3β-hydroxy-17-(benzo-1H-1,2,3-triazol-1-yl)androsta-5,16-diene (9) in 90% yield. Oxidation of 9 afforded 10 in good yield.

Synthesis of the 17-diazines, (17-diazine 14 and 17-pyrimidine 15) commenced from the readily available dehydroepiandrosterone (11, Scheme 2), which was converted to the corresponding 17 hydrazone 12 by treatment with hydrazine hydrate and hydrazine sulfate as previously described in Potter et al., A convenient, large-scale synthesis of abiraterone acetate [3β-acetoxy-17(3-pyridyl)androsta-5,16-diene], a potential new drug for the treatment of prostate cancer. *Org. Prep. Proc. Int.,* 1997, 29, 123-128. Treatment of 12 with iodine in the presence of 1,1,3,3-tetramethylguanidine gave the vinyl 17-iodide 13 in excellent yield. The palladium catalyzed cross-coupling reactions (Choshi et al., "Total synthesis of Grossularines-1, and -2." J. Org. Chem., 1995, 60, 5899-5904) of 13 with (2-tributylstannyl)pyrazine or (5-tributylstannyl)pyrimidine proceeded to gave 3β-hydroxy-17-(2-pyrazyl)-androsta-5,16-diene (14, 15%), and 3β-hydroxy-17-(5-pyrimidyl)-androsta-5,16-diene (15, 10%), respectively. The low yields of these two cross-coupling reactions may be due to instability of the stannyldiazine reagents under the reaction conditions employed. The structures of the target compounds, 14 and 15 were readily identified by their proton NMR spectra: The three nonequivalent protons of the 17-pyrazine moiety in 14 appeared as three singlets at δ 8.35, 8.48 and 8.70, while for the three protons of the 17-pyrimidine moiety in 15, two equivalent protons appear as a singlet at δ 8.73 and one proton appeared at δ 9.07. Furthermore, the 17-diazine groups of 14 and 15 exhibit different influences on the chemical shifts of their respective 16-olefinic protons with respect to the 16-proton of the precursor $\Delta^{16}$-17-iodide 13: the 16-H in 14 appeared as a singlet at δ 6.77, being significantly deshielded compared to the 16-H in 13 (δ 6.14); the 16-H in 15 appeared at δ 6.11, similar to 13. As indicated above, compound 15 was previously reported Haidar et al., however, it was synthesized by a procedure that is different from the one described herein.

A representative sample of the novel compounds were then subjected to extensive in vitro and in vivo studies as described in detail in the following sections.

The present invention also relates to method of treating prostate cancer or prostate hyperplasia comprising administering to a subject in need thereof an effective amount of a compound in accordance with the present invention. The term "treating" is used conventionally, e.g., the management or care of a subject for the purpose of combating, alleviating, reducing, relieving, improving, etc., one or snore of the symptoms associated with the prostate disease. Examples of prostate diseases that can be treated include, e.g., prostatic hyperplasia (BPH), and prostate cancer (e.g., prostatic adenocarcinoma).

The specific dose level and frequency of dosage may vary, depending upon a variety of factors, including the activity of the specific active compound, its metabolic stability and length of action, rate of excretion, mode and time of administration, the age, body weight, health condition, gender, diet, etc., of the subject, and the severity of the prostate cancer or hyperplasia. Any effective amount of the compound can be administered, e.g., from about 1 mg to about 500 mg per day, more specifically about 50 mg to about 150 mg per day. The compounds can be administered in any form by any effective route, including, e.g., oral, parenteral, enteral, intraperitoneal, topical, transdermal (e.g., using any standard patch), ophthalmic, nasally, local, non-oral, such as aerosol, spray, inhalation, subcutaneous, intravenous, intramuscular, buccal, sublingual, rectal, vaginal, intra-arterial, and intrathecal, etc. A compound of the present invention can be administered alone, or in combination with any other ingredient(s), active or inactive, for example, with physiologically acceptable vehicles to make suitable pharmaceutical compositions.

The entire disclosure of all applications, patents and publications, cited herein and of U.S. Provisional Application No. 60/657,390, filed Mar. 2, 2005, is incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLES

Biological Studies

CYP17 Inhibition Studies:

A CYP17 inhibition assay is performed according to our previously reported procedure, in which intact cytochrome P450c17-expressing *E. coli* is used as the enzyme source (Grigoryev et al., "Cytochrome P450c17-expressing *Escherichia coli* as a first-step screening system for 17α-hydroxylase-C17,20-lyase inhibitors", *Anal. Biochem.;* 1999, 267, 319-330; and "Effects of new 17α-hydroxylase/ C17,20-lyase inhibitors on LNCaP prostate cancer cell growth in vitro and in vivo", *Br. J Cancer,* 1999, 81, 622-630. IC$_{50}$ values of the compounds are determined from dose-response curves and are listed in Table 1. The IC$_{50}$ values for ketoconazole, abiraterone (a CYP17 inhibitor in clinical trials (O'Donnell, above), Chart 1) and 3β-hydroxy-17-(1H-imidazole-1-yl)androsta-5,16-diene (VN/85-1, compound 16, Chart 1, believed to be the most potent CYP17 inhibitors (Njar et al., *Current Pharm. Design,* 1999, 5: 163-180; and J. Med. Chem., 1998, 41, 902-912, above) are also determined in the same assay system for comparison. Some of the new 17-heterocycles exhibit potent inhibition of CYP17 with IC$_{50}$ values of 300-915 nM. The benzimidazoles, 5 and 6 are 4- to 6-fold more potent than the benzotriazoles 9 and 10. This result suggests that the electronic nature of the 17-heterocycle influence inhibitory activity. Furthermore, compounds with the Δ$^5$-3β-ol functionality, 5 and 9 are at least 3-fold more potent than the corresponding analogs with Δ$^4$-3-one functionality, 6 and 10, respectively. These results are in contrast to our previous results for the simple 17-azole CYP17 inhibitors. In that series of inhibitors, there is no marked difference in the inhibitory potencies between the Δ$^5$-3β-ol azoles and the corresponding Δ$^4$-3-one analogs (Njar et al., *J. Med. Chem.,* 1998, 41, 902-912, above). A possible explanation is that the bulkier benzoazoles bind differently at the active site of the enzyme such that the interaction(s) of the moiety at the 3-position is important for binding.

The binding of the substrate or inhibitory ligands to the home component of some P450 cytochromes is investigated using UV-vis difference spectroscopy (Jefcoat C. R., "Measurement of substrate and inhibitor binding to microsomal cytochrome P450 by optical difference spectroscopy", *Methods Enzymol.,* 1978, 52, 258-279). This approach is extended following standard procedure previously reported by us (Njar et al., *Bioorg. Med. Chem, Lett.,* 1996, 6, 2777-2782; and *J. Med. Chem.,* 1998, 41, 902-912). Compounds 5 and 9 each induce a type II difference spectrum, indicating coordination of steroidal nitrogen (N-3 of benzimidazole or benzotriazole ring) to the heme iron of CYP17, with formation of low-spin iron. The peak positions for the Soret maximum for the enzyme complex with 5 and 9 (426 nM) is in agreement with available data for the binding of nitrogen ligands to CYP systems, and is also in agreement with our results with other 17-azolyl CYP17 inhibitors (Njar et al., *Bioorg. Med. Chem. Lett.,* 1996, 6, 2777-2782; and *J. Med. Chem.,* 1998, 41, 902-912). The interaction of the benzoazole nitrogen with the heme iron of CYP17 suggests bulk tolerance at the 17-position, because the binding affinities of 5 and 9 are identical to that of the less sterically demanding 16, with a 17-imidazole group.

Of the two 17-diazines tested, the 17-pyrimidine 15 with an IC$_{50}$ value of 500 nM is about 8-fold more potent than the 17-pyrazine 14 (IC$_{50}$=3810 nM). As with the benzoazoles, this result suggests that the electronic nature of the 17-heterocycle influence inhibitory activity. Finally, IC$_{50}$ values in the same assay system for ketoconazole, and abiraterone are evaluated (Table 1). The most potent compound in this series, 17-benzimidazole 5, exhibits about 4 and about 3-fold improvements in CYP17 inhibition over these compounds, respectively, although it is less potent than 16.

Inhibition of Human 5α-reductase Isozymes Type 1 and 2 In Vitro:

On the basis of previous findings that some CYP17 inhibitors are able to inhibit human 5α-reductase enzymes, we briefly evaluated this new series of CYP17 inhibitors. The inhibitory activities of compounds 5, 6, 9, 10 and finasteride as a reference are determined using the DU-145 cell line (human type 1enzyme) and human homogenates of BPH tissue (human type 2 enzyme) as described by Hartmann et al., "Synthesis and evaluation of 2'-substituted 4-(4'-carboxy- or 4'-carboxymethylbenzylidene)-N-acylpiperidines: Highly potent and in vivo active steroid 5α-reductase type 2 inhibitors", *J. Med. Chem.,* 2002, 45, 3406-3417. The IC$_{50}$ values or the percent inhibition values at a concentration of 10 μM for some compound are presented in Table 1. Only compound 6 exhibits potent inhibition of both type 1 and 2 enzymes (IC$_{50}$=770 and 480 nM, respectively), although it is several fold less potent than finasteride (IC$_{50}$=60 and 2 nM, respectively).

LNCaP and PC-3AR Androgen Receptor Binding Assays:

Because we had previously demonstrated that some of our CYP17 inhibitors are potent antiandrogens for both the mutant and wild-type AR (Long et al., Gregoriyev et al. and Njar et al., *J. Med. Chem.,* 1998, 41, 902-912, above) it was of interest to assess the ability of this series of CYP17 inhibitors to bind to these receptors. AR competition is determined using labeled R1881 ([$^3$H]-R1881) in the androgen-sensitive LNCaP cells, that express mutant AR, and the androgen-independent PC-3 cells stably transfected with the wild-type AR (designated PC-3AR). Compounds 5, 6, 14 and 15, in the nanomolar concentration range, compete effectively with labeled R1881 for binding to both types of ARs in a dose-dependent manner (Figure not shown). Compounds 5, 6, 14 and 15, with IC$_{50}$ values of 384, 242, 336 and 374 nM, respectively (Table 1), versus the wild type AR are 29 to 45-fold more potent than with the clinically used antiandrogen, flutamide (IC$_{50}$=10,985 nM). As shown in Table 1, the binding affinities for the mutant AR of 5 and 6 are comparable to that of CASODEX® (bicalutamide), a currently used antiandrogen, but again superior to that of flutamide. However, the biological activity of flutamide is derived mainly from a metabolite, hydroxyflutamide, which is a much more potent AR antagonist.

Effects of Agents on LNCaP Mutant AR-mediated Transcription:

Next, we asked whether compounds 5 and 6 are acting as AR agonists or antagonists. A study on androgen-regulated transcriptional activation is performed in LNCaP cells transiently transfected with a probasin luciferase reporter construct AARZ-Luc (luciferase activity assay) (Kim et al., "Synergism of cytoplasmic kinases in IL6-induced ligand-independent activation of androgen receptor in prostate cancer cells", *Oncogene,* 2004, 23: 1838-1844; and Zhang et al., "A Small composite probasin promoter confers high levels of prostate-specific gene expression through regulation by androgens and glucocorticoids in Vitro and in Vivo", *Endocrinology,* 2000, 141: 4698-4710). Compounds 5, 6 or CASODEX® (bicalutamide) each at 0.1 and 10.0 μM have no effect on luciferase activity, whereas luciferase expression is increased approximately 99.6-fold after treatment 1.0 nM DHT for 18 h (FIG. 1). Furthermore, luciferase expression induced by exposure to 1.0 nM DHT is decreased in a concentration-dependent manner by 5, 6, and CASODEX® (bicalutamide) and in a similar fashion (FIG. 1). Together, these results suggest that compounds 5 and 6 like CASODEX® (bicalutamide) do not possess AR agonistic or partial agonistic activity and may be considered as strong, pure androgen antagonists. Although we did not test the compounds with PC-3AR/LU cells, which express wild-type AR, it is likely that they may also behave in a similar fashion. We has previously shown that some of our CYP17 inhibitors were more comparable to CASODEX® (bicalutamide) than to flutamide (Long et al., above), and this appears to be the case with these new compounds. In general, our novel compounds interact strongly with both AR types, an indication that the compounds may be useful for the treatment of patients with tumors expressing either wild-type or mutated AR, or for patients with amplified AR expression.

Figure 2A:
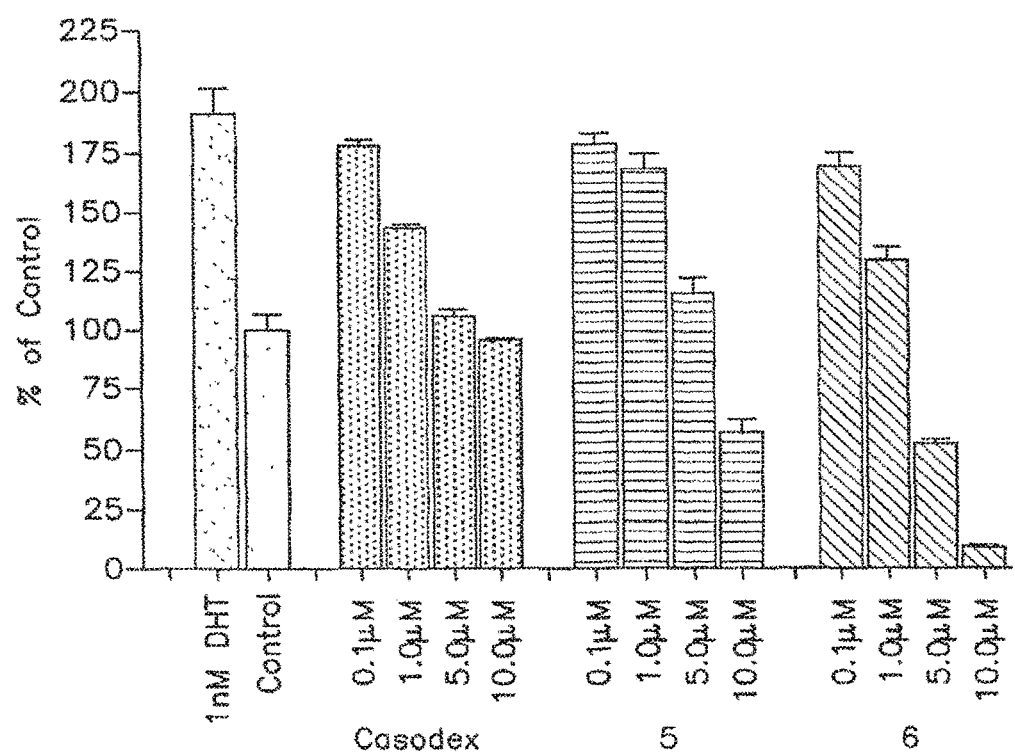
Figure 2B:
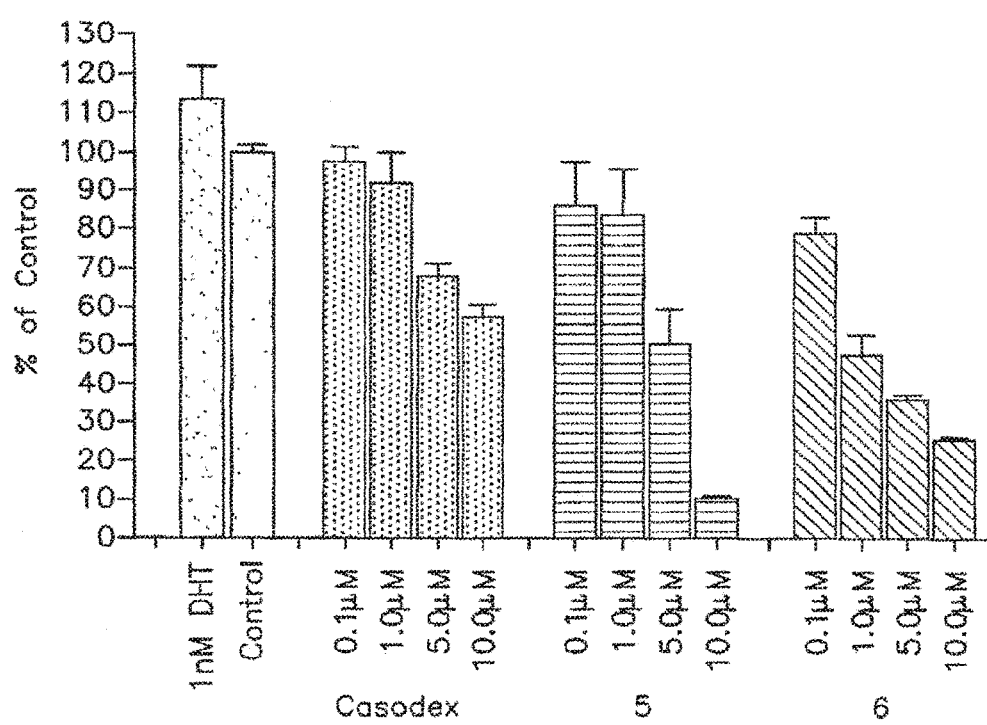

Effects of Benzoazoles on the Growth of LNCaP and LAPC-4 Prostate Cancer Cells In Vitro:

The abilities of compounds 5 and 6 to inhibit proliferation in mutant LNCaP cells stimulated by 1 nM DHT is examined. This concentration of DHT stimulated LNCaP cell proliferation by about 2-fold compared to vehicle-treated cells (FIG. 2A). As shown in FIG. 2A, compounds 5 and 6 each inhibit the DHT-induced LNCaP cell proliferation in a dose-dependent fashion, with IC50 values of 6.0 and 1.8 μM, respectively. Casodex is used as a positive control, and it exhibits similar inhibition of DHT-induced LNCaP cell proliferation (FIG. 2A, $IC_{50}$=8.6 μM). Treating the androgen-sensitive LAPC4 prostate cell line with 10 nM DHT, surprisingly, does not significantly induce cell proliferation (FIG. 2B). Other investigators have also reported that the response of LAPC4 cells to androgens is not as pronounced as that observed in LNCaP cells (Thompson et al., "Androgen antagonist activity by the antioxidant moiety of vitamin E, 2,2,5,7,8-pentamethyl-6-chromanol in human prostate carcinoma cells", *Molec. Caner Thera.*, 2003, 2, 797-803). However, compounds 5, 6 and CASODEX® (bicalutamide) each exhibit a dose-dependent inhibition of this cell line (FIG. 2B) as with the LNCaP cells. The order of inhibitory potency of LAPC4 cell proliferation is 6>5>CASODEX® (bicalutamide), with $IC_{50}$ values of 1.0, 3.2 and 10 μM, respectively. Together, these results suggest that 5 and 6 may be acting to block the action of DHT in stimulating cell proliferation, in correlation with their androgen receptor binding and activation properties described above. Compounds 5 and 6 are amongst the most potent antiandrogens described to date.

Pharmacokinetics of 5 and 6 and Metabolism of 5:

The pharmacokinetic properties in male SCID mouse for the two lead compounds, 5 and 6 are studied following our recently described procedure for other CYP17 inhibitors (Nnane et al., "Pharmacokinetic profile of 3β-hydroxy-17-(1H-123-triazol-1-yl)androsta-5,16-diene (VN/87-1), a potent androgen synthesis inhibitor in mice", *J. Steroid Biochem. Molec. Biol.*, 2001, 71, 145-152; and Handratta et al., "Potent CYP17 inhibitors: improved syntheses, pharmacokinetics and anti-tumor activity in the LNCaP human prostate cancer model", *J. Steroid Biochem. Molec. Biol.*, 2004, 92, 155-165. The results are summarized in Table 2 and FIGS. 3-5.

Figure 3:
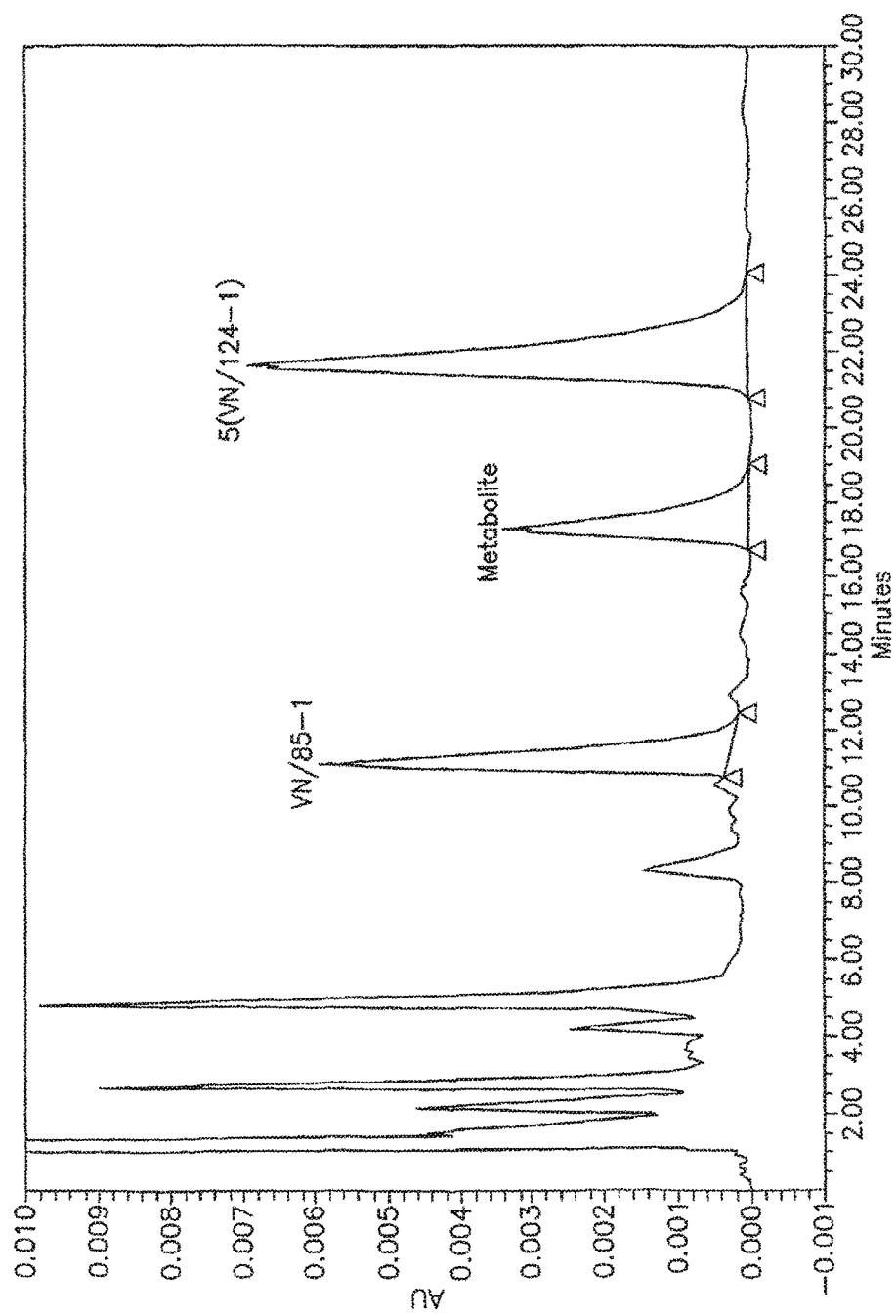

On reverse phase HPLC, 5 [retention time (rt)=21.6 min] is well resolved from the internal standard (16, rt=11.5 min), a metabolite (rt=17.3 min) and other endogenous compounds in mouse plasma (FIG. 3). The calibration curves derived for 5 are linear and reproducible (data not shown), the inter- and intra-assay variability is less than 10% and its limit of detection is 100 ng/ml. The HPLC assay is validated and used to monitor 5 in mice plasma.

Figure 4:
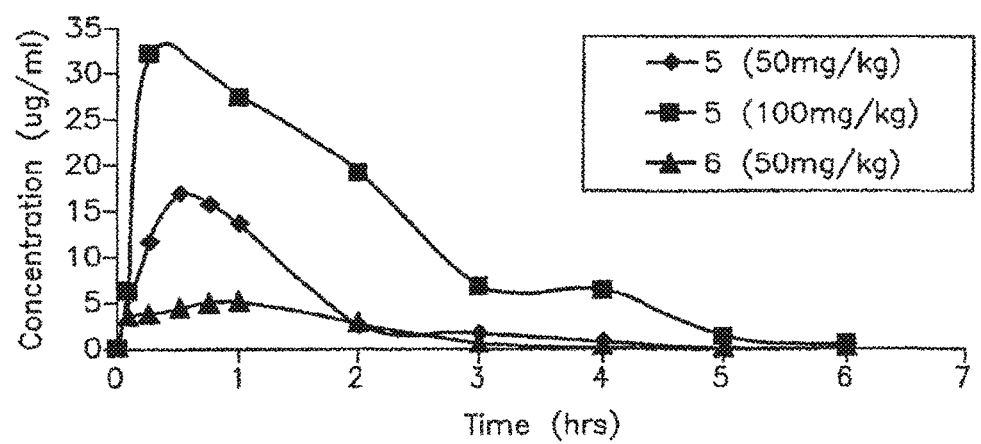

Following subcutaneous administration, the plasma concentration of 5 declines exponentially with a mean half-life of about 44.17 min and elimination rate constant of 56.5 $min^{-1}$. Compound 5 is cleared at a rate of 1986.14 ml/h/kg from the systemic circulation and was not detected 6 h after administration. The calculated non-compartmental pharmacokinetic parameters based on the plasma concentration profile following subcutaneous administration of 5 are shown in Table 2. The plasma concentration-time curves after s.c. administration of 5 (50 and 100 mg/kg) to male SCID mice are also shown in FIG. 4. After s.c. administration of 5, the observed plasma concentration in mice reach peak levels 30.0 min post dose. Compound 5 is well absorbed from the subcutaneous site and the area under the curve for the plasma concentration versus time profiles after s.c. administration increases proportionately to dose as the administration dose is changed from 50 to 100 mg/kg. Furthermore, the elimination half-life, and mean residence time are relatively constant as the dose of 5 increases from 50 to 100 mg/kg (Table 1). These results indicate that the pharmacokinetic profile of 5 is dose independent.

Figure 5:
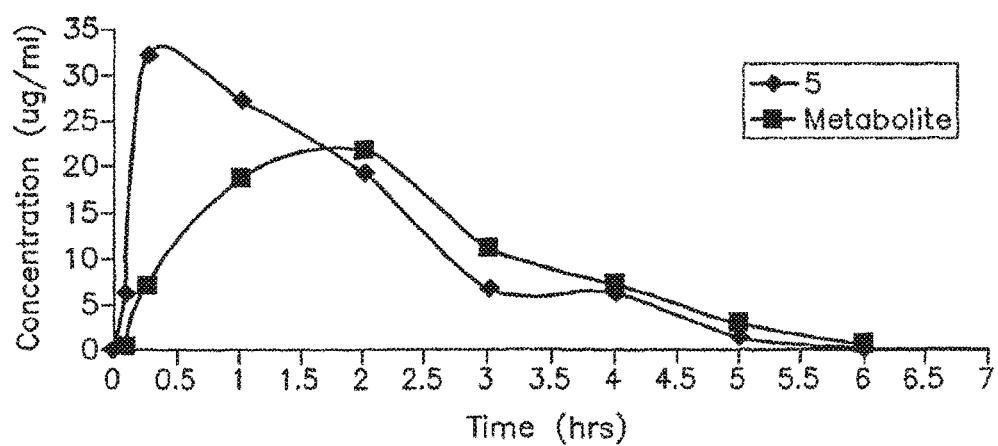

FIG. 5 shows that a significant amount of a polar metabolite [retention time, 17.3 min, see FIG. 3)] is formed from 5 and present in the plasma during the in vivo pharmacokinetic studies. The maximum amount of the metabolite is 67.72%, attained about 2 h post dose. This metabolite shows identical retention time as compound 6. This metabolite is tentatively identified by LC-MS; its molecular mass (m/z 391=M+H⁺) is consistent with the structure of 3-oxo-$\Delta^{5,16}$-tetrahydro compound 5 (i.e., 17-(1H-benzimidazol-1-yl)androst-3-one). The metabolite may have been formed from 5 via oxidation of the 3β—OH→3-oxo, followed by reduction (reductases) of both $\Delta^5$ and $\Delta^{16}$ double bonds. A similar metabolite was previously identified (formed as a result of oxidation of a 3β—OH→3-oxo, followed by isomerization of $\Delta^5$ double bond) in male mice of a closely related steroidal 17-imidazole (Handratta et al., above)

A major metabolite of 5, i.e., 17-(1H-benzimidiazol-1-yl) androst-3-one, may be synthesized from trans-androsterone; see Scheme 3. It is also expected to have analogous activity.

The in vivo pharmacokinetics of 6 in mice is unlike that of compound 5 due to the relatively low $C_{max}$ and significantly higher elimination rate (FIG. 4 and Table 2). In addition, we did not detect any metabolism(s) of compound 6 in the plasma, in contrast to our observation with compound 5.

Effects of 5 and 6 on LAPC4 Xenografts Grown in SCID Mice:

On the basis of impressive multiple in vitro biological activities, i.e., potent inhibition of CYP17, strong antiproliferative prostate cancer cell activity and antiandrogenic activities, 5 and 6 are selected for in vivo antitumor efficacy studies in androgen-depended LAPC4 human prostate cancer xenograft model.

In the first experiment, the effect of compounds 5 and 6 on the growth of well-established LAPC4 prostate cancer tumors in SCID mice is determined, and castration is used as the reference treatment. Tumor-bearing mice are assigned (n=5/group) to receive one of two doses of 5 or 6 (0.15 mmol/kg once-daily or 0.15 mmol/kg twice-daily). Tumor volumes are measured weekly and compared with controls receiving vehicle or castrated mice.

Figure 6:
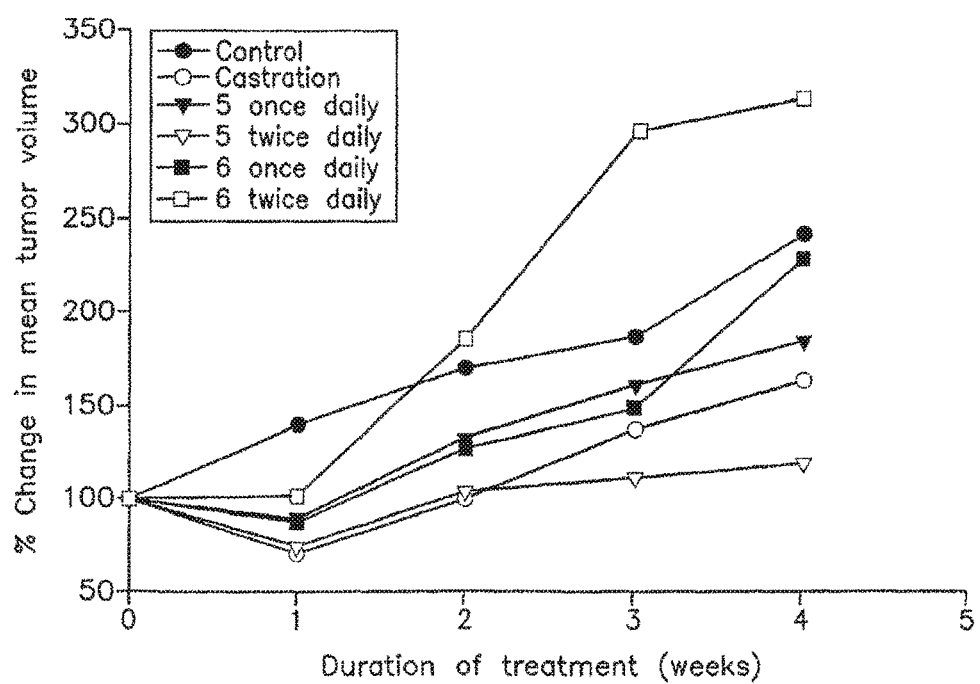

Castration leads to a 55% reduction of final tumor volume, as compared to the control (FIG. 6). Administration of 0.15 mmol/kg once daily and 0.15 mmol/kg twice daily of 5 results in reduction of average final tumor volumes of 41% and 86.5%, respectively, compared to tumors in vehicle-treated control animals (FIG. 6). In contrast to the excellent tumor growth inhibition for 5 treated mice, mice treated with compound 6 are either ineffective at the low dose or even show stimulation of tumor growth compared to control (FIG. 6). The inability of 6 to inhibit LAPC4 tumor growth in vivo is especially disappointing because the compound is very effective at inhibiting PCA cell growth in vitro, and is a highly potent pure antiandrogen (see FIG. 1). The highly significant disparity in the in vivo antitumor efficacy of 5 and 6 cannot easily be attributable to differences in the pharmacokinetic properties of the two compounds. The underlying reason(s) for the dramatic differences in in vivo antitumor efficacy of these two closely related compounds is unknown at this time. However, it may be attributable to 6 being converted in the animals to metabolite(s) that may be a strong agonist of androgen receptor thus causing tumor growth stimulation. During the study, all mice were weighed once per week. The body weights of all treated groups increased slightly and were similar to the increase observed with the control group. All mice appeared healthy and no adverse effects were observed suggesting that the compounds were without significant toxicity.

Figure 7:
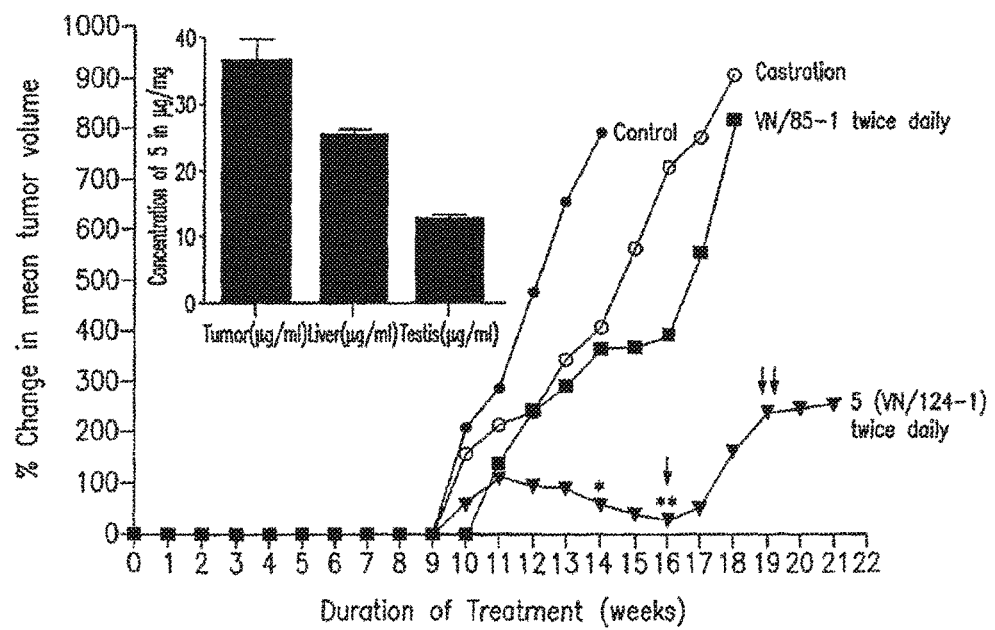

The second in vivo experiment tests the ability of 5 to inhibit the growth of LAPC4 prostate cancer cells growing in SCID mice, and 16 (Chart 1), a previously identified potent CYP17 inhibitor/antiandrogen (Gregoriyev et al. and Njar et al., *J. Med. Chem.*, 1998, 41, 902-912, above) and castration are used as reference treatments. In this experiment, treatment begins on the day that mice were inoculated subcutaneously with hormone-dependent LAPC4 cells and are castrated or injected sc twice daily with 5 or 16. FIG. 7 shows the effects of the various treatments on the emergence and on the size of tumors during the 21 weeks of therapy.

All other groups develop palpable and measurable tumor at week 10 of therapy except for the group treated with 16 (0.15 mmol/kg twice-daily) that develop palpable and measurable tumors at week 11. Total tumor volume in the control mice increases by 8-fold over 14 weeks of treatment when mice are sacrificed because of the large tumors. Thus, the tumor volumes for the other groups are compared to those of the control group at week 14 of treatment. Tumor volume in the castrated mice increases by only 4.1 fold (about 50% reduction compared to control), and is similar to the 3.7 fold increase (53.8% reduction compared to control) observed in mice treated with 16. In the mice treated with 5 (0.15 mmol/kg twice-daily), tumor volume increases by only 0.5 fold, which represents a 93.8% reduction versus control mice (P=0.00065). At week 16, the mean tumor volume in the compound 5-treated animals is found to be lower (almost negligible and dormant) than their mean tumor volume at week 10 when measurable tumors emerge. Furthermore, 5 causes a significant inhibitory effect on tumors, compared to 16 or castration, P=0.005 and 0.05, respectively. In general, tumors in the control, castration and compound 16 treated mice grow rapidly, while the tumor of the 5 treated mice grows very slowly and in a biphasic manner (FIG. 7). Compound 5 is the most effective agent, and significantly is much more effective than castration at inhibition of tumor growth. It is interesting to note that although 16 is 6 times more potent than 5 in CYP17 inhibition, the latter exhibits a superior in vivo antitumor activity. The reason(s) responsible for this phenomenon is unknown at this time, but may be in part due to better pharmacokinetic and or pharmacodynamic properties of 5.

To determine whether the "dormant" compound 5-treated prostate tumors (see FIG. 7, week 16) are able to grow on a lower dose of 5, its dose was reduced to 0.15 mmol/kg thrice a week (a 78.6% reduction in dosage) from weeks 16-19, and the tumor volumes measured weekly. During this period of treatment with reduced dose of the compound, tumors resume growth (FIG. 7). After this 3-week interval, drug treatment with the usual dose is resumed, and the tumor growth slows and reaches a plateau. These data suggest a cytostatic nature of this treatment and infer the need for continuous administration to achieve the antitumor effect.

At the end of the experiment, the levels of 5 in the tumors and organs of the 5-treated mice are determined. The 5 levels by HPLC in the tumors, testis and liver 1 h after administration of the final dose (insert of FIG. 7) are measured. Interestingly, a small (~15% relative to 5) amount of metabolite is detected only in the liver tissues. This metabolite has the same retention time as the metabolite observed in the plasma (vide supra). The highest concentration of 39.0±8.4 μm/mg tissue of 5 is measured in the s.c. tumors. The concentrations in the liver and testis are lower but detectable. The level of 5 in tumors is significantly higher that the levels measured in the plasma, which may be a result of accumulation of the compound through the period of the experiment. Thus, inhibition of tumor growth by 5 can be explained in part higher concentrations in tumor xenografts, which may exert direct cytotoxic/cytotastic effect on the prostate cancer cells. It should be stated that there is evidence to suggest a possible direct cytotoxic effect of ketoconazole (a modest CYP17 inhibitor) on prostate cancer cells.[33] In addition; the accumulation of 5 in the testes would enable inhibition of testosterone synthesis in the animals.

Although it is well established that LAPC4 are androgen-dependent, these cells can become androgen-independent, and as such represent a suitable model that mimics prostate cancer development in patients (Chen et al., above, and Kline et al., "Progression of metastatic human prostate cancer to androgen independence in immunodeficient SCID mice." *Nat. Med,* 1997, 3, 402-408). As shown in FIG. 7, we are able to replicate this phenomenon. Furthermore, our results show that treatment with 16 or castration effectively suppresses tumor growth for a certain period (androgen-dependent phase), but was ineffective thereafter (possibly as a result of an androgen-independent phase) since the tumors grow rapidly just as in intact control mice. Tumor growth in the mice treated with 5 is strongly suppressed throughout the treatment period. This suggests that 5 may have effects on androgen-independent prostate cancer. However, it is also plausible that treatment with this compound enables LAPC4 tumors to remain androgen dependent for a longer period and therefore responsive to antiandrogen therapy.

Recent studies that clearly demonstrate the up-regulation and involvement of AR in advanced and recurrent PCA (Mohler et al., and Chen et al., above) have renewed interest in the androgen receptor as a target for development of drugs to treat PCA (Tindall et al., "Symposium on androgen action in prostate cancer", *Cancer Res.*, 2004, 64, 7178-7180). Because of its potent properties, 5 may be an excellent candidate.

Conclusions:

The data reinforce our earlier concept of modification of the C17 substituent of $\Delta^{16}$ steroids to produce potent inhibitors of CYP17 as well as potent AR antagonists. The 17-benzimidazoles 5 and 6 are shown to coordinate the heme iron of CYP17, a property that may in part be responsible for their enzyme inhibitory activity. Compounds 5 and 6 exhibit almost equipotent in vitro activities for CYP17 inhibition, AR antagonism, and inhibition of prostate cancer cell growth. Surprisingly, the compounds are very different in their antitumor activities, as 5 causes marked suppression of LAPC4 tumor xenograft growth, and in contrast, 6 (0.15 mmol/kg twice daily) enhances tumor growth. The present study provides compelling evidence that 5 is a potent inhibitor of human prostate tumor growth and is remarkably more effective than castration. This is the first example of a CYP17 inhibitor/antiandrogen demonstrating in vivo antitumor activity against a prostate cancer tumor to an extent that is superbly more effective than castration. These impressive biological activities, makes 5 a strong candidate for further development as a potential drug for the treatment of prostate cancer in humans. The excellent antitumor activity of compound 5, containing a benzimidazole group makes the benzimidazoles a preferred group. However, analogs of 5 as discussed above are expected to have related activity and are included in the invention.

Experimental Section

Chemistry:

General procedures and techniques were identical with those previously reported (Njar et al., *J. Med. Chem.*, 1998, 41, 902-912). Infra red spectra are recorded on a PERKI-NELMER® 1600 FTIR spectrometer using solutions in $CHCl_3$. High-resolution mass spectra (HRMS) are determined on a 3-Tesla Finnigan FTMS-2000 FT mass spectrometer, ESI mode (Ohio State University, Department of Chemistry). As a criterion of purity for key target compounds, we provided high resolution mass spectral data with HPLC chromatographic data indicating compound homogeneity. Low-resolution mass spectra (LRMS) are determined on a Finnigan LCR-MS. Melting points (mp) are determined with a Fisher-Johns melting point apparatus and are uncorrected. Dehydroepiandrosterone and dehydroepiandrosterone acetate were purchased from Aldrich, Milwaukee, Wis. 5-Tributylstannylpyrimidine and 2-tributylstannylpyrazine were purchased from Frontier Scientific, Inc., Logan, Utah.

3β-Acetoxy-17-chloro-16-formylandrosta-5,16-diene (2):

This compound prepared from 3β-acetoxyandrost-5-en-17-one (1) as previously described, provided spectral and analytical data as described (Njar et al., *J. Med Chem.*, 1998, 41, 902-912).

3β-Acetoxy-17-(1H-benzimidazol-1-yl)-16-formylandrosta-5,16-diene (3):

A mixture of 3β-Acetoxy-17-chloro-16-formylandrosta-5,16-diene (2, 2.5 g, 6.65 mmol), benzimidazole (2.35 g, 19.9 mmol), and $K_2CO_3$ (2.76 g, 23.9 mmol) in dry DMF (20 mL) is stirred at ca. 80° C. under Ar for 1.5 h. After cooling to room temperature, the reaction mixture is poured onto ice-cold water (250 mL) and the resulting precipitate is filtered, washed with water, and dried to give a crude dirty white solid (ca 2.9 g). Purification by FCC [petroleum ether/EtOAc/$Et_3N$ (6:4:0.3)] gives 2.7 g (88.7%) of pure compound 3: mp 227-230° C.; IR ($CHCl_3$) 3691, 3024, 2951, 2359, 1725, 1670, 1604, 1491, 1452, 1375, 1253, 1032, 897, 852, 818, 700, 657, 618, 576, 565, 550, 529, 511, 476 $cm^{-1}$; $^1H$ NMR (300 MHz, $CDCl_3$) δ 1.07 (s, 6H, 18- and 19-$CH_3$), 2.04 (s, 3H, 3β-$OCH_3$), 4.60 (m, 1H, 3α-H), 5.43 (br s, 1H, 6-H), 7.35 (br. s, 2H, aromatic-Hs), 7.85 (s, 1H, aromatic-H), 7.98 (s, 1H, aromatic-H), 7.98 (s, 1H, $2^1$-H) and 9.59 (s, 1H, 16-CHO). HRMS calcd 481.2462 ($C_{29}H_{34}O_3N_2.Na^+$), found 481.2454.

3β-Acetoxy-17-(1H-benzimidazol-1-yl)androsta-5,16-diene (4):

A solution of 3β-Acetoxy-17-(1H-benzimidazol-1-yl)-16-formylandrosta-5,16-diene (3, 2.04 g, 4.45 mmol) in dry benzonitrile (10 mL) was refluxed in the presence of 10% palladium on activated charcoal (1.02 g, i.e., 50% weight of 3) for 5 h. After cooling to room temperature, the catalyst was removed by filtration through a CELITE® pad. The filtrate was evaporated, and the residue was purified by FCC [petroleum ether/EtOAc/$Et_3N$ (7.5:3:0.5)] gave 1.41 g (73.8%) of pure compound 4: mp 159-160° C.; IR ($CHCl_3$) 3687, 2947, 2854, 2358, 2340, 1725, 1633, 1609, 1557, 1489, 1454, 1373, 1291, 1253, 1195, 1136, 1031, 985 1031, 985, 910, 839, 735, 665, 590, 544, 533, 513, 502, 488 $cm^{-1}$; $^1H$ NMR (300 MHz, $CDCl_3$) δ 1.02 (s, 3H, 18-$CH_3$), 1.07 (s, 3H, 19-$CH_3$), 2.04 (s, 3H, 3β-$OCH_3$), 4.62 (m, 1H, 3α-H), 5.43 (br s, 1H, 6-H), 5.98 (s, 1H, 16-H), 7.30 (m, 2H, aromatic-Hs), 7.49 (s, 1H, aromatic-H), 7.81 (s, 1H, aromatic-H), and 7.95 (s, 1H, $2^1$-H). HRMS calcd 453.2512 ($C_{28}H_{34}O_2N_2.Na^{30}$), found 453.2511.

3β3-Hyroxy-17-(1H-benzimidazol-1-yl)androsta-5,16-diene (5):

The acetate 4 (1.3 g 3.02 mmol) was dissolved in methanol (20 mL) under an inert Ar atmosphere, and the resulting solution treated with 10% methanolic KOH (8 mL). The mixture was stirred at room temperature for 1.5 h, and then concentrated under reduced pressure at approx. 40° C. to a volume of 10 mL. This solution was poured into ice water (300 mL), and the resulting white precipitate was filtered, washed with water and dried. Crystallization from EtOAc/MeOH gave 5 (1.10 g, 94%), mp 189-190° C.; IR ($CHCl_3$) 2934, 2339, 1609, 1490, 1453, 1291, 1040, 837, 808, 705, 663, 608, 578, 550, 517 $cm^{-1}$; $^1H$ NMR (300 MHz, $CDCl_3$) δ 1.02 (s, 3H, 18-$CH_3$), 1.07 (s, 3H, 19-$CH_3$), 3.55 (m, 1H, 3α-H), 5.41 (br s, 1H, 6-H), 5.99 (s, 1H, 16-H), 7.30 (m, 2H, aromatic-Hs), 7.54 (s, 1H, aromatic-H), 7.80 (s, 1H, aromatic-H), and 7.96 (s, 1H, $2^1$-H). HRMS calcd 411.2407 ($C_{26}H_{32}ON_2.Na^+$), found 411.2396.

17-(1H-benzimidazol-1-yl)androsta-4,16-diene-3-one (6):

From a mixture of compound 5 (660 mg, 1.70 mmol), 1-methly-4-piperidone (2.5 mL), and toluene (40 mL) was distilled off ca. 10 mL. Aluminum isopropoxide (521 mg, 2.55 mmol) was then added, and the mixture was refluxed under Ar for 4 h. After cooling, the mixture was diluted with EtOAc (50 mL), washed successively with 5% aqueous $NaHCO_3$ (×3) and brine (×2), and then dried ($Na_2SO_4$). The solvent was evaporated, and the crude product was purified by FCC [$CH_2Cl_2$/EtOH (25:1)] to give the title compound 6 (544 mg, 82%): mp 201-204° C.; IR ($CHCl_3$) 2946, 3858, 1622, 1611, 1490, 1453, 1376, 1291, 1270, 1228, 1189, 893, 850, 837, 722, 662, 615, 568, 553, 537, 519 $cm^{-1}$; $^1H$ NMR (300 MHz, $CDCl_3$) δ 1.04 (s, 3H, 18-$CH_3$), 1.24 (s, 3H, 19-$CH_3$), 5.78 (s, 1H, 4-H), 5.99 (s, 1H, 16-H), 7.31 (m, 2H, aromatic-Hs), 7.48 (m, 1H, aromatic-H), 7.81 (s, 1H, aromatic-H), and 7.95 (s, 1H, $2^1$-H). HRMS calcd 409.2250 ($C_{26}H_{30}ON_2.Na^+$), found 409.2250.

Reaction of 3β-acetoxy-17-chloro-16-formylandrosta-5,16-diene (2) with benzo-1H-1,2,3-triazole and $K_2CO_3$: 3β-Acetoxy-17-(benzo-2H-1,2,3-triazol-2-yl)-16-formylandrosta-5,16-diene (7a) and 3β-Acetoxy-17-(benzo-1H-1,2, 3-triazol-1-yl)-16-formylandrosta-5,16-diene (7b):

A mixture of compound 2 (2.5 g, 6.65 mmol), benzotriazole (2.35 g, 19.9 mmol), and $K_2CO_3$ (2.76 g, 23.9 mmol) in dry DMF (20 mL) was stirred at ca. 80° C. under Ar for 45 min. After cooling to room temperature, the reaction mixture was poured onto ice-cold water (250 mL) and the resulting precipitate was filtered, washed with water, and dried to give a crude dirty white solid. Purification by FCC [pet.Ether/EtOAc, (4:1)] first gave 3β-acetoxy-17-(benzo-2H-1,2,3-triazol-2-yl)-16-formylandrosta-5,16-diene (7a, 0.3 g, 9.8%) as minor product; mp 248-250° C.; IR ($CHCl_3$) 3023, 2945, 2358, 1725, 1657, 1600, 1375, 1257 1032, 728, 656, 584, 564, 540, 526, 506, 498 $cm^{-1}$; $^1H$ NMR (300 MHz, $CDCl_3$) δ 1.11 (s, 3H, 18-$CH_3$), 1.37 (s, 3H, 19-$CH_3$), 2.04 (s, 3H, 3β-$OCH_3$), 4.62 (m, 1H, 3α-H), 5.43 (br s, 1H, 6-H), 7.43 (d, 1H, J=2.4 Hz, aromatic-Hs), 7.45 (d, 1H, J=2.7 Hz, aromatic-H), 7.88 (d, 1H, J=2.7 Hz, aromatic-H), 7.90 (d, 1H, J=2.4 Hz, aromatic-H) and 10.66 (s, 1H, 16-CHO). HRMS; calcd 482.2414 ($C_{28}H_{33}O_3N_3.Na^+$), found 482.2413. Further elution with the same solvent system afforded the major product, 3β-acetoxy-17-(benzo-1H-1,2,3-triazol-1-yl)-16-fomylandrosta-5,16-diene (7b, 2.3 g, 75.4%); mp: 186-188° C.; IR ($CHCl_3$) 3023, 2948, 1725, 1670, 1604, 1488, 1450, 1374, 1253, 1196, 1032, 846, 824, 720, 658, 619, 548, 527, 504, 497 cm$^{-1}$; $^1$H NMR (300 MHz, CDCl$_3$) δ 1.07 (s, 6H, 18- and 19-CH$_3$), 2.04 (s, 3H, 3β-OCH$_3$), 4.60 (m, 1H, 3α-H), 5.43 (br s, 1H, 6-H), 7.46 (m, 2H, aromatic-Hs), 7.57 (d, 1H, J=6.9 Hz, aromatic-H), 8.15 (d, 1H, J=8.4 Hz), aromatic-H), and 9.59 (s, 1H, 16-CHO). HRMS calcd. 482.2414 (C$_{28}$H$_{33}$O$_3$N$_3$.Na$^+$), found 482.2416.

3β-Acetoxy-17-(benzo-1H-1,2,3-triazol-1-yl)androsta-5,16-diene (8):

A mixture of bis(triphenyphosphine)rhodium(I) carbonyl chloride (303 mg, 0.438 mmol) and 1,3-bis-(dipbenylphosphino)propane (394 mg, 0.954 mmol) in dry xylene (40 mL) was stirred at 80° C. under Ar for 15 min when fine yellow precipitate formed. Compound 7b (1.71 g, 3.72 mmol) was added, and the mixture was refluxed under Ar for 18 h, and then concentrated under reduced pressure. The crude product was purified by FCC [pet ether/EtOAc/Et$_3$N, (8.9:1:0.1)] to give 1.2 g (74.7%) of pure compound 8; mp 184-186° C. IR (CHCl$_3$) 3063, 2918, 2389, 2358, 1725, 1458, 1373, 1254, 1069, 1031, 843, 809, 786, 692, 646, 560, 535, 528, 512, 494 cm$^{-1}$; $^1$H NMR (300 MHz, CDCl$_3$) δ 1.10 (s, 3H, 18-CH$_3$), 1.25 (s, 3H, 19-CH$_3$), 2.04 (s, 3H, 3β-OCH$_3$), 4.64 (m, 1H, 3α-H), 5.43 (br s, 1H, 6-H), 6.01 (s, 1H, 16-H), 7.40 (t, 1H, J=7.8 Hz, aromatic-H), 7.51 (t, 1H, J=7.8 Hz, aromatic-H), 7.67 (d, 1H, J=8.1 Hz, aromatic-H), and 8.10 (d, 1H, J=8.1 Hz, aromatic-H). HRMS calcd 454.2465 (C$_{27}$H$_{33}$O$_2$N$_3$.Na$^{30}$), found 454.2469.

3β-Hydroxy-17-(benzo-1H-1,2,3-triazol-1-yl)androsta-5,16-diene (9):

The method followed that described for compound 5 but using 3β-acetoxy-17-(benzo-1H-1,2,3-triazol-1-yl)androsta-5,16-diene (8; 700 mg, 1.62 mmol). Recrystallization from EtOAc/MeOH give the title compound 9 (600 mg, 95%); mp 241-244° C.; IR (CHCl$_3$) 3603, 2937, 2859, 1609, 1488, 1451, 1373, 1287, 1243, 1069, 1040, 1007, 953, 845, 805, 715, 665, 618, 570, 553, 517 cm$^{-1}$; $^1$H NMR (300 MHz, CDCl$_3$) δ 1.09 (s, 3H, 18-CH$_3$), 1.24 (s, 3H, 19-CH$_3$), 3.55 (m, 1H, 3α-H), 5.41 (br s, 1H, 6-H), 6.06 (s, 1H, 16-H), 7.40 (t, 1H, J=7.8 Hz, aromatic-H), 7.52 (t, 1H, J=7.8 Hz, aromatic-H), 7.67 (d, 1H, J=8.1 Hz, aromatic-H), and 8.10 (d, 1H, J=8.1 Hz, aromatic-H). HRMS calcd 412.2359 (C$_{25}$H$_{31}$ON$_3$.Na$^+$), found 412.2365.

17-(benzo-1H-1,2,3-triazol-1-yl)androsta-4,16-diene-3-one (10):

The method followed that described for compound 6 but using β-hydroxy-17-(benzo-1H-1,2,3-triazol-1-yl)androsta-5,16-diene (9; 500 mg, 1.28 mmol). Purification of the crude product by FCC [CH$_2$Cl$_2$/EtOH, (50:1)] afforded the titled compound 10 (420 mg, 84.4%); mp: 280-283° C.; IR (CHCl$_3$) 2944, 1658, 1450, 1070, 8444, 825, 721, 624, 589, 564, 554, 541, 521 cm$^{-1}$; $^1$H NMR (300 MHz, CDCl$_3$) δ 1.26 (s, 3H, 18-CH$_3$), 1.27 (s, 3H, 19-CH$_3$), 5.77 (s, 1H, 4-H), 6.01 (s, 1H, 16-H), 7.40 (t, 1H, J=7.8 Hz, aromatic-H), 7.52 (t, 1H, J=7.8 Hz, aromatic-H), 7.67 (d, 1H, J=7.8 Hz, aromatic-H), and 8.10 (d, 1H, J=8.1 Hz, aromatic-H). HRMS calcd 410.2203 (C$_{25}$H$_{29}$ON$_3$.Na$^+$), found 410.2185.

Dehydroepiandrosterone-17 hydrozone (12):

Dehydroepiandrosterone (11, 3.5 g, 12.2 mmol) was dissolved in ethanol (60 mL) and the resulting solution was treated with hydrazine hydrate (2.37 mL, 0.049 mol) followed by a solution of hydrazine sulfate (7.9 mg, 0.061 mmol) in 0.25 mL of water. The mixture was stirred at room temperature for 12 h and then poured into ice water. The resulting precipitate was filtered, washed with water, and dried to give white crystals of the titled compound 12; mp: 242-244° C. (lit. 204-206° C.);[22] $^1$H NMR (300 MHz, CDCl$_3$): δ 0.76 (s, 3H, 18-CH$_3$), 1.05 (s, 3H, 19-CH$_3$), 3.74 (br s, 1H, 3-H) and 5.35 (s, 1H, 6-H).

17-Iodoandrosta-5,16-diene-3β-ol (13):

A stirred solution of iodine (12;16 g, 0.0203 mol) in dry of THF (144 mL) and dry of Et$_2$O (72 mL) was cooled in an ice bath to 0° C. and the solution was treated with 1,1,3,3 tetramethylguanidine (6.72 mL, 6.24 g, 0.054 mole). A solution of compound 12 (3.0 g, 9.9 mmol) in THF (81 mL) was added dropwise to the iodine solution over 2 h maintaining the reaction temperature at 0° C. The reaction mixture was then concentrated under vacuum, cooled in an ice-bath, and then dried to under vacuum at room temperature to afford a yellow solid (13, 3.65 g, 92.4%). mp: 169-171° C. (lit. 175-176° C.);[22]IR (CHCl$_3$) 2935, 1371, 1039, 862, 843, 799, 715, 665, 582, and 566 cm$^{-1}$; $^1$H NMR (300 MHz, CDCl$_3$): δ 0.76 (s, 3H, 18-CH$_3$), 1.05 (s, 3H, 19-CH$_3$), 3.50 (br s, 1H, 3αH), 5.35 (s, 1H, 6-H) and 6.14 (s, 1H, 16-H).

3β-Hydroxy-17-(2-pyrazyl)-androsta-5,16-diene (14):

A mixture of 17-iodoandrosta-5,16-diene-3β-ol (13; 0.5 g, 1.257 mmol) in solution with dry dimethylformamide (DMF, 10 mL) along with tetrakis(triphenylphosphate) palladium (Pd(PPh$_3$)$_4$) (71.6 mg, 0.062 mmol) and (2-tributylstannyl) pyrazine (774.6 mg, 2.099 mmol) was heated at 120° C. for 20 h. After cooling, the mixture was diluted with cold water (50 mL), and extracted with EtOAc (30 mL×3). The combined EtOAc extract was washed with brine and water, dried over Na$_2$SO$_4$ and then concentrated to give a brownish solid. This crude product was purified by flash column chromatography [FCC, pet.ether/EtOAc/Et$_3$N (3:2: 0.15)] to give 14 (66 mg, 15%); mp: 199-201° C. $^1$H NMR (300 MHz, CDCl$_3$): δ 0.94 (s, 3H, 18-CH$_3$), 1.08 (s, 3H, 19-CH$_3$), 3.52 (br s, 1H, 3α-H), 5.40 (s, 1H, 6-H), 6.77 (s, 1H, 16-H), 8.35 (s, 1H, pyrazine-H), 8.48 (s, 1H, pyrazine-H), 8.70 (s, 1H, pyrazine-H). HRMS calcd 350.2358 (C$_{23}$H$_{30}$ON$_2$), found 350.2354.

3β-Hydroxy-17-(5-pyrimidyl)-androsta-5,16-diene (15):

Reaction of 13 (0.645 g, 1.623 mmol) as described above for 14, but using (5-tributylstannyl) pyrimidine (1.0 g, 2.710 mmol) dissolved in 10 mL of dry DMF along with (Pd(PPh$_3$)$_4$) (92.88 mg, 0.0804 mmol) and (5-tributylstannyl) pyrimidine (1.0 g, 2.710 mmol) and following purification by [FCC, pet.ether/EtOAc/Et$_3$N (3:2:0.15)] gave 3β-hydroxy-17-(5-pyrimidyl)-androsta-5,16-diene 15 (44 mg, 10%); mp: 231-233° C. (lit. 240-242° C.);[19] 1H NMR (300 MHz, CDCl$_3$): δ 1.05 (s, 3H, 18-CH$_3$), 1.08 (s, 3H, 19-CH$_3$), 3.83 (br s, 1H, 3α-H), 5.39 (s, 1H, 6-H), 7.26 (s, 1H, 16-H), 8.73 (s, 2H, 4$^1$-H and 6$^1$-H) and 9.07 (s, 1H, 2$^1$-H). HRMS calcd 350.2358 (C$_{23}$H$_{30}$ON$_2$), found 350.2348.

In Vitro Assay of CYP17:

The in vitro CYP17 inhibitory activities of the compounds are evaluated using our rapid acetic acid releasing assay (AARA), utilizing intact P450c17-expressing E. coli as the enzyme source (Grigoryev, above). It involves the use of [21-$^3$H]-17α-hydroxypregnenolone as the substrate and CYP17 activity is measured by the amount of tritiated acetic acid formed during the cleavage of the C-21 side chain of the substrate. This establishes that the method is comparable in terms of accuracy and reliability to the HPLC analysis procedure used by researchers in the field (Grigoryev, above). IC$_{50}$ values are obtained directly from plots relating percentage inhibition versus inhibitor concentration over appropriate ranges. Each compound is tested at a minimum of five different concentrations. The assays are performed in triplicate, and the IC$_{50}$ values reported are the mean of triplicate experiments. The standard deviations were ±5% of the mean values.

Human 5α-Reductase Type 1 and 2 Assay:

The inhibitory activities of compounds and finasteride as reference are determined using the DU145 cell line (for human type 1 enzyme) and human prostate homogenate (BPH tissue for type 2 enzyme) according to the procedure described by Hartmann and colleagues (Picard et al., "Synthesis and evaluation of 2'-substituted 4-(4'-carboxy- or 4'-carboxymethylbenzylidene)-N-acylpiperidines: Highly potent and in vivo active steroid 5α-reductase type 2 inhibitors", *J. Med Chem.*, 2002, 45,3406-3417). The percent inhibition values at a concentration of 10 μM or, in case of more potent compounds, the $IC_{50}$ values are determined.

Competitive Androgen receptor (AR) Binding and Luciferase Assays:

AR Binding/Competition Assay:

Wells in 24-well multiwell dishes are coated with poly-1-lysine (0.05 mg/ml) for 5 minutes, dried, rinsed with sterilized, distilled water and dried for 2 hours. To determine the kinetics of R1881 binding to the LNCaP AR and the wild-type AR, LNCaP and PC3AR cells are plated ($2-3\times10^5$) in 24 well multiwell dishes in steroid-free medium and allowed to attach. The following day the medium is replaced with serum-free, steroid free RPMI supplemented with 0.1% BSA and containing [$^3$H]R1881 (0.01-10 nM) in the presence or absence of a 200 fold excess of cold DHT, to determine nonspecific binding, and 1 μM triamcinolone acetonide to saturate progesterone and glucocorticoid receptors. Following a 2-hour incubation period at 37° C., cells are washed twice with ice-cold DPBS and solubilized in DPBS containing 0.5% SDS and 20% glycerol. Extracts are removed and cell associated radioactivity counted in a scintillation counter. The data is analyzed, including Kd and Bmax determination, by nonlinear regression using GRAPHPAD PRISM software. When the concentration required to almost saturate AR in both cell lines is established, the ability of the test compounds (0.1 nM-10 μM) to displace [$^3$H]R1881 (5.0 nM) from the receptors is determined as described above. The $IC_{50}$ of each compound is determined by nonlinear regression with GRAPHPAD PRISM software (GraphPad Software, Inc, San Diego, Calif.).

Luciferase Transactivation Assay:

Transcriptional activation assay is carried out as described previously by Kim et al., above, with minor modifications. The probasin luciferase reporter construct ARR2-Luc is generated by insertion of the minimal probasin promoter ARR2, kindly provided by Dr R Matusik of Vanderbilt University Medical Center (*Endocrinology* 2000, 141: 4698-4710) into the polyclonal linker region of PGL3-enhancer vector (PROMEGA®). The pRL-null (PROMEGA®) is used as the internal control. Briefly, LNCaP cells grown in 24-well plates coated with poly-L-lysine were transfected with ARR2-Luc in the phenol-red free RPMI 1640 medium containing 5% charcoal-stripped FBS (HYCLONE®). 24 h post-transfection, the cells are incubated with fresh phenol-red free serum-free RPMI 1640 medium with or without DHT and inhibitors for 18 h. Luciferase activities are measured in triplicates by using dual luciferase assay system according to the manufacturer's instruction (PROMEGA®). The results are presented as the fold induction, that is, the relative luciferase activity of the treated cells divided by that of the control.

Cell Culture and Viability Assay:

LNCaP cells are grown in RPMI 1640 medium supplemented with 10% FBS and 1% penicillin/streptomycin solution. To determine the effect of novel compounds on cell proliferation, cells are transferred into steroid-free medium three days prior to the start of the experiments. Steroid-free medium consisted of phenol red free RPMI supplemented with 5% dextran-coated, charcoal treated serum, and 1% penicillin/streptomycin solution. Growth studies are then performed by plating cells ($3\times10^4$) in 24-well multi-well dishes (Corning, Inc. Corning, N.Y.). After a 24 hours attachment period, the medium is aspirated and replaced with steroid-free medium containing vehicle or the indicated concentration of DHT (1 nM) and compounds (0.1 μM-10 μM). Control wells are treated with vehicle (ethanol). This medium is changed every three days and the number of viable cells is compared by WST-1 [4-[3-(4-iodophenyl)-2-(4-nitrophenyl)-2H-5-tetrazolio]-1,3-benzene disulfonate] assay on the seventh day. Following incubation of cells for the above-mentioned time, 10% WST-1 solution is added to each well and incubated at 37° C. for three hours. Following incubation, plates are slightly shaken and immediately read at 450 nm with a scanning multi-well spectrophotometer. All results represent the average of a minimum of three wells. Additional control consists of medium alone with no cells.

Pharmacokinetic Studies:

All animal studies are performed according to the guidelines and approval of the Animal Care Committee of the University of Maryland School of Medicine, Baltimore. Male SCID mice weighing 20-22 gm (8-10 weeks old) obtained from NCI, Frederick, Md., USA are maintained in a controlled environment of about 25° C., 50% relative humidity and 12 h of light and 12 h of dark cycles and allowed free access to food and water. Compounds 5 and 6 are formulated in 40% β-cyclodextrin in water and a single subcutaneous dose is given to mice. The animals are sacrificed at various times up to 6 h after drug administration and blood was obtained by cardiac puncture under light halothane (Ayerst, New York, N.Y., USA) anesthesia.

HPLC Analysis: Chromatographic separations and quantification of the steroids and the appropriate internal standards are achieved by a reverse phase HPLC method on a WATER® NOVAPAK® 08 column (3.9×150 rom) protected by WATER® guard cartridge packed with pellicle C18 as previously described. Briefly, the HPLC system used in this study consisted of WATER® solvent delivery system, WATER® controller (Milford, Mass.), coupled to a WATER® 717$^{plus}$ autosampler and a WATER® 996 photodiode array detector operated at 242.7 nm. The mobile phase composition is water/MeOH/CH$_3$CN (35:35:30, v/v/v+200 μL of Et$_3$N and 0.77 g of NH$_4$OAc per 1000 mL of mobile phase) at a flow rate of 1.0 mL/min. The HPLC analysis is performed at ambient temperature and data acquisition and management is achieved with a WATER® millennium chromatography manager.

Sample Preparation:

Test tubes containing mouse plasma (200 μL), 5 or 6 and VN/85-1 (internal standard, 10 μL of 100 μg/mL), are extracted with diethyl ether (2×2 mL) using a vortex mixer for 3 minutes and centrifuged at 3000 g for 5 min. The organic layers are evaporated to dryness under a gentle stream of air. The residue is reconstituted in an aliquot of the mobile phase (100 μL) and filtered using 0.2 μm Teflon filters before HPLC analysis.

Calibration Curve and HPLC Assay Validation:

The calibration curves for 5 in plasma and tissue and for 6 in plasma are constructed by spiking varying amounts of the compounds into extraction tubes (duplicate) containing plasma (200 μL) and tissue preparations (200 μL) from untreated animals to give final concentrations of 0.1-100.0 μg/mL. Appropriate blank extraction tubes are also prepared and an aliquot of the internal standard is added into each extraction tube to give a final concentration of 5 µg/ml. The calibration samples are taken through the sample preparation procedure as described above. An aliquot of the reconstituted extract (50 µl) is injected into the HPLC system and the ratio of the peak areas for each analyte to that of the internal standard are plotted against concentrations of 5 or 6. The precision and accuracy of the assays are determined from a range of known concentrations of the inhibitors in blank plasma and taken through the HPLC procedure. The study is repeated on three separate occasions.

Data Analysis:

Pharmacokinetic calculations are performed as previously described. The non-compartmental pharmacokinetic calculations are performed using WINNOLIN® (Scientific Consulting Inc.). One-way analysis of variance (ANOVA) on SIGMASTAT® for WINDOWS® version 1.0 is used to compare different treatment groups at the 95% confidence level. The Bonferroni post-hoc test is used for determination of significance. A P-value of less than 0.05 is considered as statistically significant.

In Vivo Antitumor Studies (LAPC-4 Prostate Cancer Xenografts):

All animal studies are performed according to the guidelines and approval of the Animal Care Committee of the University of Maryland School of Medicine, Baltimore. Male severe combined immunodeficient (SCID) mice 4-6 weeks of age purchased from the National Cancer Institute-Frederick Cancer Research and Development Center (Fredrick, Md.) are housed in a pathogen-free environment under controlled conditions of light and humidity and allowed free access to food and water. Tumors are developed from LAPC4 cells inoculated subcutaneously (s.c.) in the mice essentially as previously described (21). LAPC4 cells are grown in IMEM with 15% FBS plus 1% PS and 10 nm DHT until 80% confluent. Cells are scraped into DPBS, collected by centrifugation, and resuspended in Matrigel (10 mg/ml) at $3 \times 10^7$ cells/ml. Mice are injected s.c. with 100 µl of the cell suspension at one site on each flank. Tumors are measured weekly with calipers, and tumor volumes are calculated by the formula: $4/3 \pi \times r_1^2 \times r_2 (r_1 < r_2)$.

In the first experiment, LAPC4 tumors are allowed to grow for 8-10 weeks following inoculation. Groups of 5 mice with comparable total tumor volumes are either castrated or treated with 5 and 6 (0.15 mmol/kg once-daily and 0.15 mmol/kg twice-daily, 9 a.m. and 5 p.m.). Mice are castrated under methoxyfluorane anesthesia. Compounds 5 and 6 were prepared at 17.2 mg/ml in a 0.3% solution of hydroxypropyl cellulose in saline, and mice receive s.c. injections daily. Control and castrated mice are treated with vehicle only. Tumors are measured weekly for the 4 weeks of treatment and tumor volumes are calculated. At the end of the treatment period, the animals are sacrificed under halothane anesthesia; tumors are excised, weighed and stored at −80° C. Animals are also weighed weekly and monitored for general health status and signs of possible toxicity due to treatment.

In the second experiment, mice are inoculated with LAPC4 cells and are divided into four groups of 5 mice each. The control and castrated group receive vehicle, while the other two groups receive either VN/85-1 (0.15 mmol/kg twice-daily, 9 a.m. and 5 p.m.) or 5 (0.15 mmol/kg twice-daily, 9 a.m. and 5 p.m.). These treatments are initiated one day after LAPC4 cell inoculation; continued for 14 weeks for control group, 19 weeks (for VN/85-1 and castration groups) and for 21 weeks for 5 treated group and tumors are measured and processed as described above.

Measurement of 5 (VN/124-1) Levels in Tumor, Liver and Testes:

The animals in the VN/124-1-treated group are sacrificed 1 h after the last VN/124-1 administration, and tumor, liver and testis are harvested and snap frozen in liquid nitrogen. Tissue samples are homogenized in phosphate buffer (pH=7.4, 0.5 ml/mg of tissue). Homogenized tissue (200 µl) is spiked with the internal standard, VN/85-1 (10 µL from 100 µg/mL stock solution), and then extracted with $Et_2O$ (2×2 mL) by vortexing for 3 min followed by centrifugation at 3000 g for 5 min. The $Et_2O$ extract is separated and evaporated to dryness under a gentle stream of air. The residue is reconstituted in 100 µL of the HPLC mobile phase, filtered through 0.2 µm Teflon filters and then analyzed by HPLC as described above.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

TABLE 1

CYP17 and 5α-reductase actvities and androgen receptor binding of novel 17-heteroaryl compounds.

| | | 5α-Reductase % inhibition at 10 µM [$IC_{50}$ (nM)][b] | | AR Binding IC50 (nM)[c] | |
|---|---|---|---|---|---|
| Compound [a] | CYP17 $IC_{50}$ (nM)[b] | type 1[d] | type 2[e] | LNCaP | PC3-AR |
| 5 | 300.0 | 4 | 53 | 845 | 384 |
| 6 | 915.0 | [770] | [480] | 1200 | 242 |
| 9 | 1250.0 | ni[f] | 17 | — | — |
| 10 | 5817.4 | 21 | 56 | — | — |
| 14 | 3810.0 | — | — | — | 366 |
| 15 | 500.0 | — | — | — | 374 |
| For comparison | | | | | |
| VN/85-1 | 50.0 | — | — | — | — |
| Abiraterone | 800.0 | — | — | — | — |
| Ketoconazole | 1100.0 | — | — | — | — |
| Finasteride | — | [60.0] | [2.0] | — | — |
| Casodex | — | — | — | 940 | — |
| Flutamide | — | — | — | 11600 | 10985 |

[a] We have previously reported the synthesis of VN/85-1 (Njar et. al., above) Abiraterone was synthesized as described by Potter et al (A convenient, large-scale synthesis of abiraterone acetate [3β-acetoxy-17(3-pyridyl)androsta-5,16-dien], a potential new drug for the treatment of prostate cancer. Org. Prep. Proc. Int. 1977, 29, 123-128).

[b] $IC_{50}$ is the concentration of inhibitor required to inhibit the enzyme activity by 50%, each in duplicate for CYP17, triplicate for 5α-reductase and AR binding.

[c] $IC_{50}$ is the concentration of compound required for a 50% displacement of [$^3$H]R1881 from the androgen receptor.

[d] Prostatic tumor cell line (DU-145) expressing type 1 enzyme; substrate: 5 nM [1β-$^3$H]androstenedione.

[e] Enzyme from BPH tissue (type 2 enzyme), 125 µg of protein, substrate: 210 nM [1β,2β-$^3$H]testosterone.

[f] ni = no inhibition up to 10 µM.

— = not determined.

TABLE 2

Pharmacokinetic parameters for 5 (50 and 100 mg/kg) and 6 (50 mg/kg) after s.c. administration.

| Parameter [a] | 5 | | 6 |
|---|---|---|---|
| | 50 mg/kg | 100 mg/kg | 50 mg/kg |
| $t_{1/2}$ (min) | 44.17 ± 1.15 | 36.6 ± 1.6 | 37.93 ± 1.15 |
| $K_{el}$ (min$^{-1}$) | 56.5 ± 0.94 | 68.49 ± 1.26 | 0.0183 ± 0.004 |
| AUC (min · µg/mL) | 1440.00 ± 60.23 | 1813.94 ± 10.94 | 647.10 ± 20.23 |
| $T_{max}$ (min) | 30.00 ± 0.0 | 30.00 ± 0.0 | 60.00 ± 0.00 |
| $C_{max}$ (µg/mL) | 16.82 ± 0.37 | 32.23 ± 0.34 | 5.15 ± 0.09 |
| MRT (min) | 65.40 ± 0.60 | 60.46 ± 1.54 | 79.95 ± 0.01 |
| $V_d$ (mL/kg) | 2098.99 ± 4.11 | 3276.39 ± 26.71 | 4207.24 ± 6.25 |

[a] Values are expressed as mean ± S.E., n = 5,

BRIEF DESCRIPTION OF SCHEMES AND FIGURES

Chart 1: Structures of abirateron3 and VN/85-1 (16)

Scheme 1: Synthesis of 17-benzoazole compounds (5, 6, 9 and 10).

Scheme 2: Synthesis of 17-diazine compounds (14 and 15).

Scheme 3: Synthesis of metabolites of trans-androsterone, including VNLG/81.

FIG. 1: The effects of 5, 6 and CASODEX® (bicalutamide) on transcriptional activity of luciferase mediate through LNCaP-AR in LNCaP-ARR2-1u prostate cancer cells. Cells in steroid-free medium were treated with vehicle, or increasing concentrations of either 5 or CASODEX® (bicalutamide) with and without 1 nM DHT for 18 h. Cells were then assayed for luciferase activity as described in "Materials and Methods". The bars represent the mea light units [counts per second (cps)/unit protein, i.e., relative luciferase activity] in triplicate wells from three separate experiments. FIGS. 2a and 2b: The effects of 5, 6 and CASODEX® (bicalutamide) on (FIG. 2a) LNCaP and (FIG. 2b) LAPC4 prostate cancer cell growth. Cells were grown in steroid-free medium before plating. Triplicate wells were then co-treated with increasing concentrations of 5,6 or CASODEX® (bicalutamide) and DHT as described in "Materials and Methods." The percentage (compared to control) of growth inhibition after 7 days of treatment was determined using WST-1 assay. The results represent the average and standard deviation of three experiments performed in triplicate.

FIG. 3: Typical HPLC chromatogram of 5, 16 (internal standard) and metabolite extracted from mouse plasma. The retention times for 16, metabolite, and 5 were 11.5, 17.3 and 21.6 min, respectively.

FIG. 4: Pharmacokinetic profiles of 5 and 6 following administration of a single subcutaneous bolus dose to male SCID mice. Each data point represents the mean plasma concentrations obtained from three mice. The standard deviations (not shown) were±5-8% of the mean values.

FIG. 5 Pharmacokinetic profiles of 5 and metabolite following a single subcutaneous bolus dose (100 mg/kg·bw) of 5 to male mice.

FIG. 6: In vivo antitumor activity of 5, 6 and orchidectomy on the growth of LAPC4 prostate tumors in male SCID mice. Groups of five mice with LAPC-4 tumors were treated with 5 (0.15 mmol/kg/day or 0.30 mmol/kg/day). Tumors volumes were measured weekly, and the percentage of change in tumor volume was determined after 28 days of treatment. The standard deviations of tumor volumes (not shown) were±10-12% of the mean values.

FIG. 7: The effects of 5, 16, and orchidectomy on the formation and growth of LAPC4 prostate tumors in male SCID mice. 3×107 LAPC-4 cells were injected s.c. into the dorsal flank of the SCID mice. One group of mice was castrated. The other groups of mice received either vehicle or 5 (0.15 mmol/kg twice-daily) or 16 (0.15 mmol/kg twice-daily). Daily treatment with 5 or 16 was initiated 1 day after cell inoculation. Tumors volumes were measured weekly, and the percentage of change in tumor volume was determined after 16 weeks of treatment. * Indicates significant difference of 5 versus control, castration and 16 at week 14 (P=0.00065, 0.05 and 0.0097, respectively). ** Indicates significant differences of 5 versus castration and 16 at week 16 (P=0.047 and 0.0047, respectively). ↓-↓↓: Period of reduced administered dose of 5.

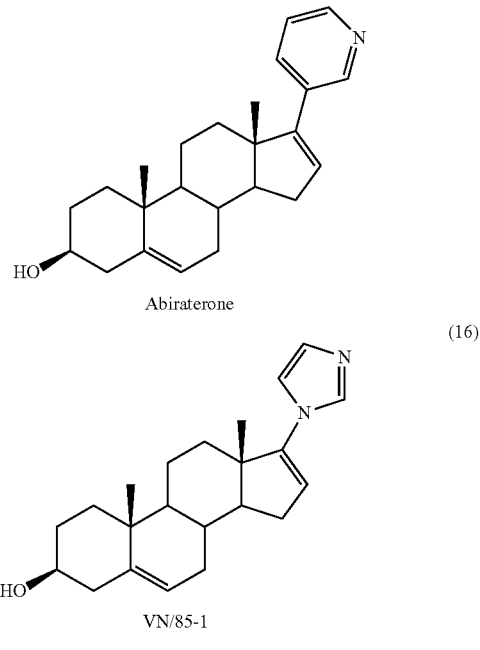

Chart 1. Structure of Abiraterone and VN/85-1

Abiraterone (16)

VN/85-1

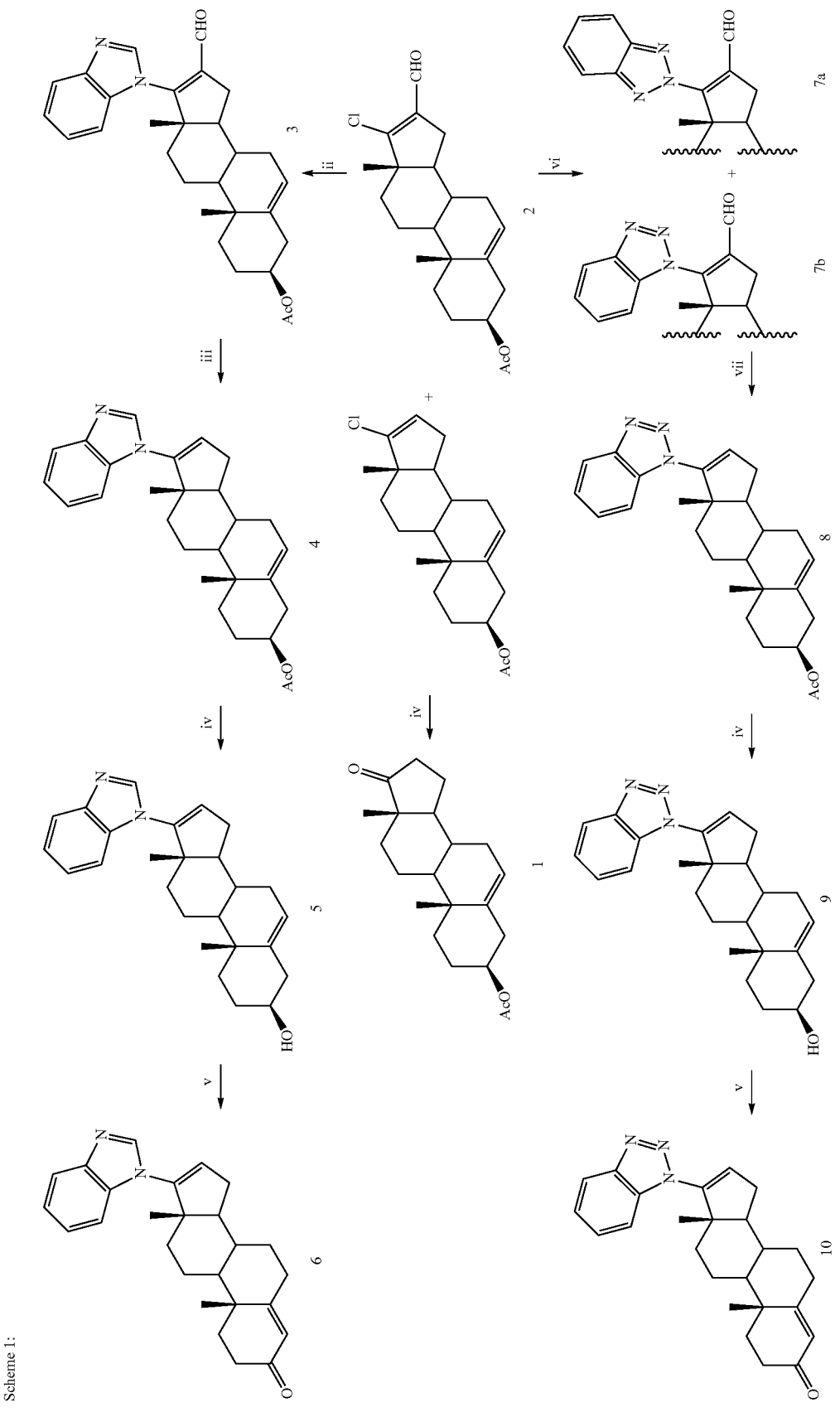
Scheme 1: (i) POCl₃, DMF, CHCl₃, Ar, reflux; (ii) benzimidazole, K₂CO₃, DMF, Ar, 80° C.; (iii) 10% Pd on activated charcoal, PhCN, reflux; (iv) 10% Methanolic KOH, Ar, rt.; (v) Al(i-PrO)₃, 1-methyl-4-piperidone, toluene, reflux; (vi) benzo-1H-1,2,3-triazole, K₂CO₃, DMF, Ar, 80° C.; (vii) (PPh₃)₂RhCOCl—Ph₂(CH₂)₃PPh₂, xylene, Ar, reflux.

Scheme 2:
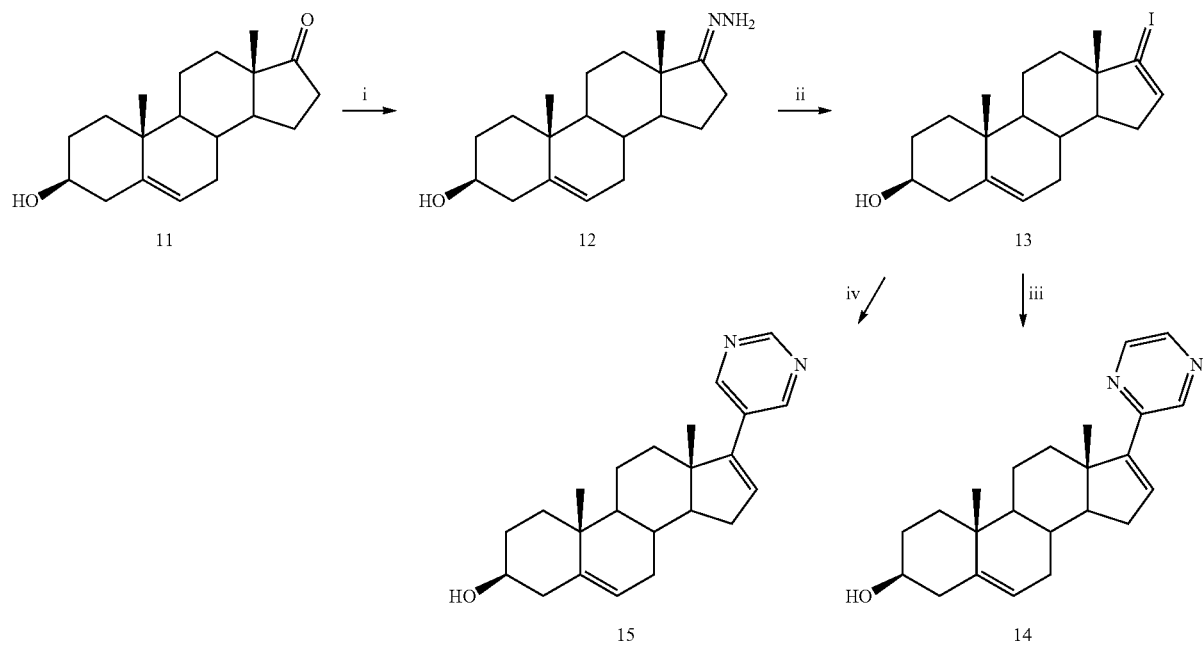
i) N₂H₄·H₂O, N₂H₄·H₂SO₄, EtOH, ii) I₂/THF, TG; iii) (2-tributylstannyl pyrazine/Pd(PPh₃)₄; iv) (5-tributylstannyl)pyrimidine/Pd(PPh₃)₄

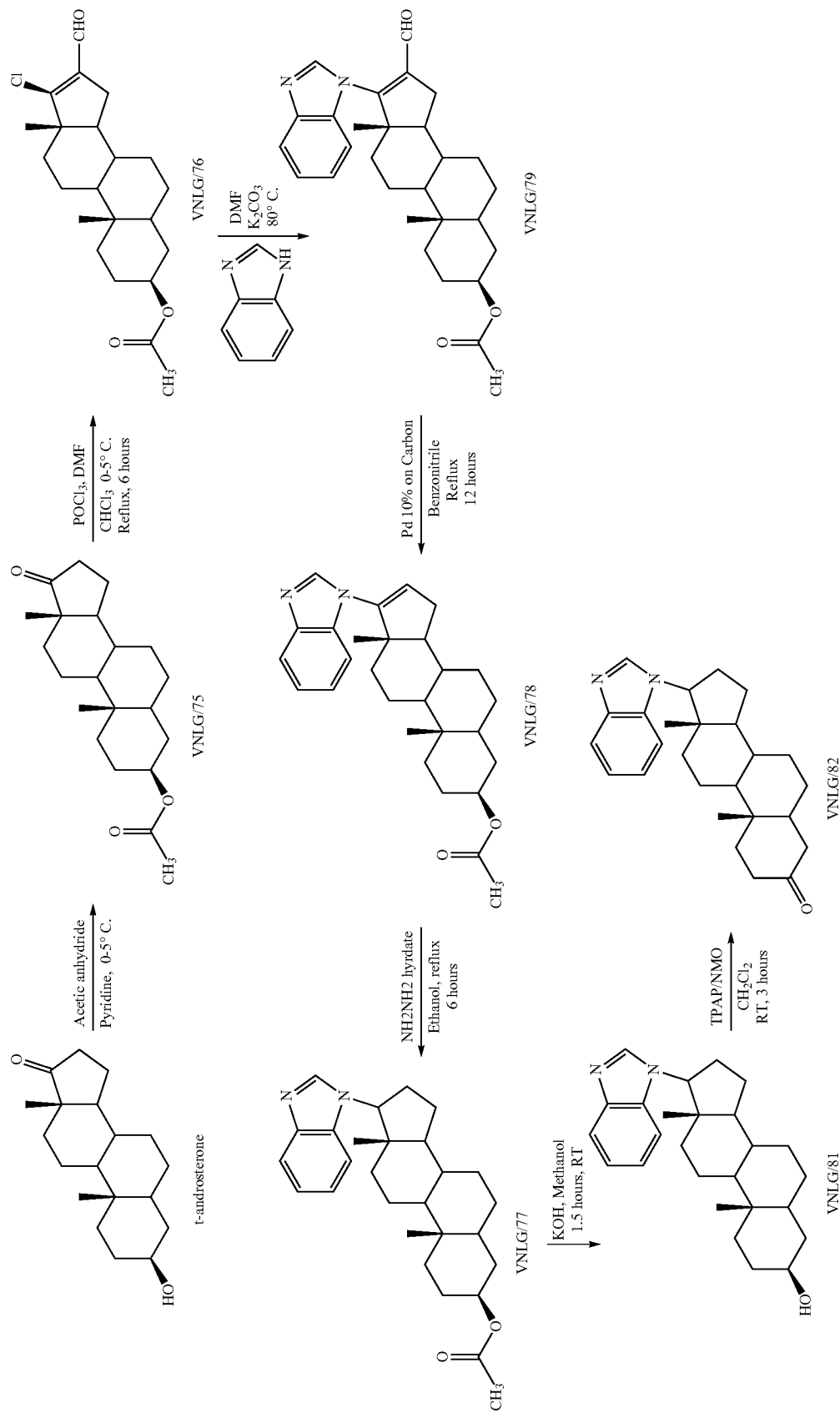

We claim:
1. A pharmaceutical composition comprising a compound of formula:

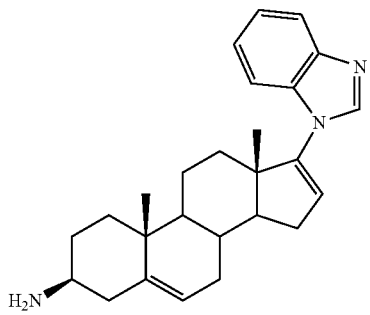 [SMILES: C[C@]12CC[C@H](N)CC1=CCC1C2CC[C@]2(C)C(n3cnc4ccccc43)=CCC12]

or a pharmaceutically acceptable salt thereof.

2. The pharmaceutical composition of claim 1, wherein the pharmaceutical composition is formulated for oral, parenteral, enteral, intraperitoneal, topical, transdermal, ophthalmic, nasal, subcutaneous, intravenous, intramuscular, buccal, sublingual, rectal, vaginal, intra-arterial, or intrathecal administration.

3. A method of treating prostate cancer comprising administering to a patient in need thereof the pharmaceutical composition of claim 1.

4. A method of treating prostate cancer comprising administering to a patient in need thereof a compound of formula:

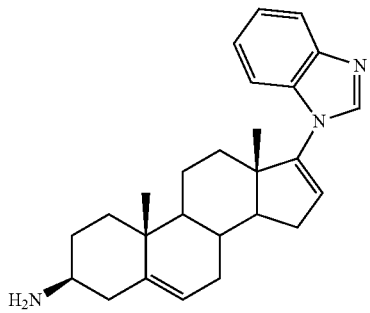 [SMILES: C[C@]12CC[C@H](N)CC1=CCC1C2CC[C@]2(C)C(n3cnc4ccccc43)=CCC12]

or a pharmaceutically acceptable salt thereof.

5. A method of reducing androgen receptor activity in a human or non-human subject, the method comprising administering to a human or non-human subject in need thereof a compound of formula:

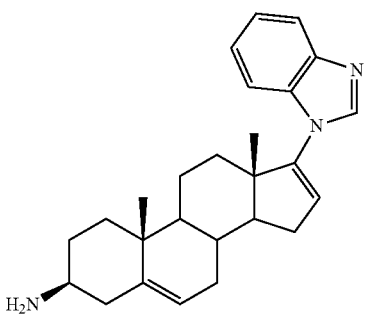 [SMILES: C[C@]12CC[C@H](N)CC1=CCC1C2CC[C@]2(C)C(n3cnc4ccccc43)=CCC12]

or a pharmaceutically acceptable salt thereof,
so as to reduce androgen receptor activity in the human or non-human subject.

6. A method of inhibiting CYP17 activity in a human or non-human subject, the method comprising administering to a human or non-human subject in need thereof a compound of formula:

or a pharmaceutically acceptable salt thereof,
so as to inhibit CYP17 activity in the human or non-human subject.

* * * * *